US012152028B2

(12) United States Patent
Dener et al.

(10) Patent No.: US 12,152,028 B2
(45) Date of Patent: Nov. 26, 2024

(54) METHODS OF PREPARING HETEROARYL-KETONE FUSED AZADECALIN GLUCOCORTICOID RECEPTOR MODULATORS

(71) Applicant: Corcept Therapeutics Incorporated, Menlo Park, CA (US)

(72) Inventors: Jeffrey Mark Dener, Menlo Park, CA (US); Hazel Joan Hunt, Menlo Park, CA (US); Travis Lemons, Menlo Park, CA (US); Gary Reid, Menlo Park, CA (US); Kilian Garrec, Menlo Park, CA (US); Thomas C. Stephens, Menlo Park, CA (US); Adam Daisuke Gammack Yamagata, Menlo Park, CA (US); Yunguo Lu, Menlo Park, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 0 days.

(21) Appl. No.: 17/560,048

(22) Filed: Dec. 22, 2021

(65) Prior Publication Data

US 2022/0227753 A1   Jul. 21, 2022

(30) Foreign Application Priority Data

Dec. 25, 2020   (WO) ................ PCT/CN2020/139524

(51) Int. Cl.
| | | |
|---|---|---|
| C07D 471/04 | (2006.01) | |
| A61K 31/4745 | (2006.01) | |
| A61K 45/06 | (2006.01) | |
| A61P 1/16 | (2006.01) | |

(52) U.S. Cl.
CPC ........ *C07D 471/04* (2013.01); *A61K 31/4745* (2013.01); *A61K 45/06* (2013.01); *A61P 1/16* (2018.01); *C07B 2200/13* (2013.01)

(58) Field of Classification Search
CPC .......................... C07B 2200/13; C07D 471/04
See application file for complete search history.

(56) References Cited

U.S. PATENT DOCUMENTS

| | | | |
|---|---|---|---|
| 4,963,558 A | 10/1990 | Hotten et al. | |
| 5,696,127 A | 12/1997 | Jones et al. | |
| 6,166,013 A | 12/2000 | Coghlan et al. | |
| 6,583,180 B2 | 6/2003 | Link et al. | |
| 6,680,310 B2 | 1/2004 | Belanoff et al. | |
| 7,576,076 B2 | 8/2009 | Clark et al. | |
| 7,678,813 B2 | 3/2010 | Clark et al. | |
| 7,790,745 B2 | 9/2010 | Yang et al. | |
| 7,799,782 B2 | 9/2010 | Munson et al. | |
| 7,928,237 B2 | 4/2011 | Clark et al. | |
| 8,003,689 B2 | 8/2011 | Veverka | |
| 8,173,674 B2 | 5/2012 | Keil et al. | |
| 8,324,203 B2 | 12/2012 | Clark et al. | |
| 8,461,172 B2 | 6/2013 | Clark et al. | |
| 8,598,154 B2 | 12/2013 | Clark et al. | |
| 8,658,128 B2 | 2/2014 | Altschul et al. | |
| 8,685,973 B2 | 4/2014 | Clark et al. | |
| 8,710,035 B2 | 4/2014 | Pan et al. | |
| 8,859,774 B2 | 10/2014 | Hunt et al. | |
| 8,889,867 B2 | 11/2014 | Clark et al. | |
| 8,969,557 B2 | 3/2015 | Harriman et al. | |
| 9,114,147 B2 | 8/2015 | Altschul et al. | |
| 9,149,485 B2 | 10/2015 | Pan et al. | |
| 9,273,047 B2 | 3/2016 | Hunt et al. | |
| 9,289,436 B2 | 3/2016 | Szmulewitz et al. | |
| 9,314,473 B2 | 4/2016 | Altschul et al. | |
| 9,320,747 B1 | 4/2016 | Altschul et al. | |
| 9,422,323 B2 | 8/2016 | Houpis et al. | |
| 9,623,032 B2 | 4/2017 | Pan et al. | |
| 9,707,223 B2 | 7/2017 | Hunt et al. | |
| 9,801,893 B2 | 10/2017 | Szmulewitz et al. | |
| 9,829,495 B2 | 11/2017 | Moraitis | |
| 9,943,505 B2 | 4/2018 | Hunt et al. | |
| 9,956,216 B2 | 5/2018 | Hunt et al. | |
| 10,047,082 B2 | 8/2018 | Hunt et al. | |
| 10,117,852 B2 | 11/2018 | Hunt et al. | |
| 10,213,414 B2 | 2/2019 | Hunt et al. | |
| 10,323,034 B2 | 6/2019 | Hunt et al. | |
| 10,413,540 B2 | 9/2019 | Hunt | |
| 10,449,178 B2 | 10/2019 | Hunt et al. | |
| 10,456,392 B2 | 10/2019 | Hunt et al. | |

(Continued)

FOREIGN PATENT DOCUMENTS

| | | |
|---|---|---|
| EP | 0145121 A2 | 6/1985 |
| EP | 0375210 A1 | 6/1990 |

(Continued)

OTHER PUBLICATIONS

Identification of the Clinical Candidate (R)-(1-(4-Fluorophenyl)-6-((1-methyl-1H-pyrazol-4-yl)sulfonyl)-4,4a,5,6,7,8 hexahydro-1H-pyrazolo[3,4-g]isoquinolin-4a-yl)(4-(trifluoromethyl)pyridin-2-yl)methanone (CORT125134): A Selective Glucocorticoid Receptor (GR) Antagonist Hunt et al. J. Med. Chem. 2017 (Year: 2017).*

The First Large-Scale Synthesis of MK-4305: A Dual Orexin Receptor Antagonist for the Treatment of Sleep Disorder Baxter et al. dx.doi.org/10.1021/op1002853 |Org. Process Res. Dev. 2011, 15, 367-375 (Year: 2011).*

Synthetic Strategies for Oseltamivir Phosphate Shibasaki et al. Eur. J. Org. Chem. 2008, 1839-1850 (Year: 2008).*

Amine Protection / Deprotection FischerSci https://www.fishersci.co.uk/gb/en/scientific-products/lab-reporter-europe/chemicals/amine-protection-deprotection.html#:~:text=2%2DDEPROTECTION,are%20the%20acids%20of%20choice. (Year: 2014).*

(Continued)

*Primary Examiner* — Jeffrey S Lundgren
*Assistant Examiner* — Eric Tran
(74) *Attorney, Agent, or Firm* — Mintz, Levin, Cohn, Ferris, Glovsky and Popeo, P.C.

(57) ABSTRACT

The present invention provides methods of preparing heteroaryl-ketone fused azadecalin glucocorticoid receptor modulators, and compositions having low impurity levels.

41 Claims, 7 Drawing Sheets

(56) References Cited

U.S. PATENT DOCUMENTS

| | | |
|---|---|---|
| 10,568,880 B2 | 2/2020 | Hunt |
| 10,646,474 B2 | 5/2020 | Hunt et al. |
| 10,787,449 B2 | 9/2020 | Hunt et al. |
| 10,828,280 B2 | 11/2020 | Hunt et al. |
| 10,898,478 B2 | 1/2021 | Hunt |
| 10,973,813 B2 | 4/2021 | Hunt et al. |
| 11,370,789 B2 | 6/2022 | Hunt et al. |
| 11,464,764 B2 | 10/2022 | Scott et al. |
| 11,576,907 B2 | 2/2023 | Hunt et al. |
| 11,648,245 B2 | 5/2023 | Hunt et al. |
| 2002/0115613 A1 | 8/2002 | Kumar |
| 2003/0064974 A1 | 4/2003 | Belanoff |
| 2004/0102422 A1 | 5/2004 | Gaston |
| 2004/0229855 A1 | 11/2004 | Belanoff |
| 2005/0085464 A1 | 4/2005 | Sapse et al. |
| 2005/0124533 A1 | 6/2005 | Schatzberg et al. |
| 2005/0245588 A1 | 11/2005 | Ali et al. |
| 2006/0063748 A1 | 3/2006 | Belanoff |
| 2007/0128627 A1 | 6/2007 | Simons et al. |
| 2007/0203179 A1 | 8/2007 | Clark et al. |
| 2007/0281928 A1 | 12/2007 | Clark et al. |
| 2008/0070950 A1 | 3/2008 | Benjamin et al. |
| 2008/0287419 A1 | 11/2008 | Bruncko et al. |
| 2009/0156672 A1 | 6/2009 | Budunova et al. |
| 2010/0135956 A1 | 6/2010 | Gant et al. |
| 2010/0179115 A1 | 7/2010 | Belanoff |
| 2010/0292477 A1 | 11/2010 | Clark et al. |
| 2011/0166110 A1 | 7/2011 | Clark et al. |
| 2011/0166115 A1 | 7/2011 | Belanoff |
| 2011/0269728 A1 | 11/2011 | Pan et al. |
| 2012/0022121 A1 | 1/2012 | Dalton et al. |
| 2012/0201747 A1 | 8/2012 | Altschul et al. |
| 2012/0220565 A1 | 8/2012 | Clark et al. |
| 2013/0225633 A1 | 8/2013 | Hunt et al. |
| 2014/0005158 A1 | 1/2014 | Belanoff |
| 2014/0038926 A1 | 2/2014 | Hunt et al. |
| 2015/0080389 A1 | 3/2015 | Hunt et al. |
| 2015/0196640 A1 | 7/2015 | Cacase et al. |
| 2016/0215049 A1 | 7/2016 | Feldhaus et al. |
| 2017/0020860 A1 | 1/2017 | Hunt et al. |
| 2017/0045535 A1 | 2/2017 | Moraitis |
| 2017/0273972 A1 | 9/2017 | Hunt et al. |
| 2018/0125856 A1 | 5/2018 | Moraitis et al. |
| 2018/0193313 A1 | 7/2018 | Hunt et al. |
| 2018/0280378 A1 | 10/2018 | Hunt |
| 2019/0076424 A1 | 3/2019 | Hunt |
| 2020/0197372 A1 | 6/2020 | Scott et al. |
| 2021/0169872 A1 | 6/2021 | Hunt et al. |
| 2021/0369701 A1 | 12/2021 | Hunt et al. |
| 2024/0131020 A1 | 4/2024 | Bastin |

FOREIGN PATENT DOCUMENTS

| | | |
|---|---|---|
| JP | H09505030 A | 5/1997 |
| JP | 2002506032 A | 2/2002 |
| JP | 2002544271 A | 12/2002 |
| WO | 9504734 A1 | 2/1995 |
| WO | 9945925 A1 | 9/1999 |
| WO | 0069846 A1 | 11/2000 |
| WO | 03015692 A2 | 2/2003 |
| WO | 03061651 A1 | 7/2003 |
| WO | 2005087769 A1 | 9/2005 |
| WO | 2009064738 A2 | 5/2009 |
| WO | 2011113015 A2 | 9/2011 |
| WO | 2012027702 A1 | 3/2012 |
| WO | 2013039916 A1 | 3/2013 |
| WO | 2013177559 A2 | 11/2013 |
| WO | 2015077530 A1 | 5/2015 |
| WO | 2016014365 A1 | 1/2016 |
| WO | 2016055533 A1 | 4/2016 |
| WO | 2016141365 A1 | 9/2016 |
| WO | 2017023694 A1 | 2/2017 |
| WO | 2018151613 A1 | 9/2017 |
| WO | 2020132023 A1 | 6/2020 |
| WO | 2020172501 A1 | 8/2020 |
| WO | 2020190351 | 9/2020 |
| WO | 2021163058 | 8/2021 |
| WO | 2022134033 A1 | 6/2022 |
| WO | 2022140600 A1 | 6/2022 |
| WO | 2024006773 | 1/2024 |

OTHER PUBLICATIONS

Identification of the Clinical Candidate (CORT125134): A Selective Glucocorticoid Receptor (GR) Antagonist Hunt et al. J. Med. Chem. 2017 (Year: 2017).*

International Search Report and Written Opinion, Application No. PCT/CN2020/139524, dated Sep. 26, 2021, 15 pages.

International Search Report and Written Opinion, Application No. PCT/US2021/064947, dated Apr. 15, 2022, 16 pages.

(2017) Capryol® 90—Propylene glycol monocaprylate type II, Accessed Nov. 14, 2021. First made available to public on May 28, 2017. Available from:<https://www.gattefosse.com/pharmaceuticals-products/capryol-90 >, 4 pages.

Extended European Search Report for Application No. EP09774351.2, dated May 7, 2012, 7 pages.

Extended European Search Report for Application No. EP19188885.8, dated Oct. 28, 2019, 6 pages.

Extended European Search Report, Application No. EP13751132.5, dated Mar. 21, 2016, 14 pages.

Extended European Search Report, Application No. EP13793417.0, dated Jan. 4, 2016, 7 pages.

Extended European Search Report, Application No. EP16183642.4, dated Dec. 1, 2016, 12 pages.

Extended European Search Report, Application No. EP18154256.4, dated Mar. 26, 2018, 6 pages.

Extended European Search Report, Application No. EP18777520.0, dated Jul. 16, 2020, 9 pages.

International Preliminary Report on Patentability for Application No. PCT/US2013/027150, dated Sep. 4, 2014, 7 pages.

International Preliminary Report on Patentability, Application No. PCT/US2013/042732, dated Nov. 25, 2014, 5 pages.

International Search Report and Written Opinion for Application No. PCT/US2009/049273, dated Aug. 14, 2009, 7 pages.

International Search Report and Written Opinion for Application No. PCT/US2011/049408, dated Jan. 30, 2012, 10 pages.

International Search Report and Written Opinion for Application No. PCT/US2013/027150, dated Apr. 29, 2013, 9 pages.

International Search Report and Written Opinion for Application No. PCT/US2013/027720, dated Jun. 17, 2013, 9 pages.

International Search Report and Written Opinion for Application No. PCT/US2018/025547, dated Aug. 9, 2018, 13 pages.

International Search Report and Written Opinion for PCT Application No. PCT/US2019/067108, dated Jun. 25, 2020, 13 pages.

International Search Report and Written Opinion, for Application No. PCT/US2010/034382, dated Jul. 9, 2010, 7 pages.

International Search Report for PCT Application No. PCT/US2013/042732, Dec. 2, 2013, 4 pages.

Office Action, Application No. JP2007-503030, dated Feb. 23, 2011, 8 pages.

(2005) "Preservatives and Antioxidants Database—Compounding Today", Available at: <CompoundingToday.com | Preservatives and Antioxidants Database>, 2 pages.

Study of Drug 1 (Enzalutamide) Plus Drug 2 (Relacorilant) for Patients with Prostate Cancer, ClinicaiTrials.gov NCT03674814, 8 pages.

Study to Evaluate Cort125134 in Combination with Nab-Paclitaxel in Patients with Solid Tumors, ClinicaiTrials.gov NCT02762981, 8 pages.

Substantive Examination Adverse Report, MYPI2014003289, mailed on dated Mar. 30, 2018, 2 pages.

Aherne et al. (2002) "Finding the Needle in the Haystack: Why Highthroughput Screening is Good for Your Health", Breast Cancer Research, 4(4):148-154.

Aisen et al. (Feb. 8, 2000) "A Randomized Controlled Trial of Prednisone in Alzheimer's Disease. Alzheimer's Disease Cooperative Study", Neurology, 54(3):588-593.

(56) References Cited

OTHER PUBLICATIONS

Akiyama et al. (May-Jun. 2000) "Inflammation and Alzheimer's Disease", Neurobiol Aging, 21(3):383-421.
Antonarakis et al. (Sep. 2011) "Emerging Therapeutic Approaches in the Management of Metastatic Castration Resistant Prostate Cancer", Prostate Cancer and Prostatic Diseases, 14(3):206-218.
Arrat et al. (May 8, 2015) "ACTH (Acthar Gel) Reduces Toxic SOD1 Protein Linked to Amyotrophic Lateral Sclerosis in Transgenic Mice: A Novel Observation", PLoS One, 10(5):e0125638 (12 pages).
Attard et al. (Jun. 15, 2011) "Translating Scientific Advancement into Clinical Benefit for Castration-Resistant Prostate Cancer Patients", Clinical Cancer Research, 17(12):3867-3875.
Behl et al. (May 1997) "Protection Against Oxidative Stress-Induced Neuronal Cell Death—A Novel Role for RU486", European Journal of Neuroscience, 9(5):912-920.
Belova et al. (Aug. 2009) "Glucocorticoid Receptor Expression in Breast Cancer Associates with Older Patient Age", Breast Cancer Research and Treatment, 116(3):441-447.
Benagiano et al. (Oct. 2008) "Selective Progesterone Receptor Modulators 3: Use in Oncology, Endocrinology and Psychiatry", Expert Opinion on Pharmacotherapy, 9(14):2487-2496.
Block et al. (Mar. 6, 2017) "Glucocorticoid Receptor Expression in 20 Solid Tumor Types Using Immunohistochemistry Assay", Cancer Management and Research, 9:65-72.
Bolton et al. (Aug. 2007) "Cell- and Gene-Specific Regulation of Primary Target Genes by the Androgen Receptor", Genes & Development, 21(16):2005-2017.
Brusaferri et al. (Jun. 2000) "Steroids for Multiple Sclerosis and Optic Neuritis: A Meta-Abstract Analysis of Randomized Controlled Clinical Trials", Journal of Neurology, 247(6):435-442.
Caccamo et al. (Jan. 16, 2013) "Glucocorticoids Exacerbate Cognitive Deficits in TDP-25 Transgenic Mice Via a Glutathionemediated Mechanism: Implications for Aging, Stress and TDP-43 Proteinopathies", The Journal of Neuroscience, 33(3):906-913.
Carri et al. (Aug. 30, 2003) "Neurodegeneration in Amyotrophic Lateral Sclerosis: The Role of Oxidative Stress and Altered Homeostasis of Metals", Brain Research Bulletin, 61(4):365-374.
Chan et al. (Nov. 1, 2000) "Prognostic Significance of Gleason Score 3+4 versus Gleason Score 4+3 Tumor at Radical Prostatectomy", Adult Urology, 56(5):823-827.
Check et al. (May 2014) "Evidence that Mifepristone, A Progesterone Receptor Antagonist, Can Cross the Blood Brain Barrier and Provide Palliative Benefits for Glioblastoma Multiforme Grade IV", Anticancer Research, 34(5):2385-2388.
Check et al. (May 2014) "Mifepristone Causing Complete Remission of Rapidly Advancing Leukemia with Measurement of Progesterone-induced Blocking Factor", Anticancer Research, 34(5):2413-2416.
Chen et al. (May 30, 1997) "Androgen and Glucocorticoid Receptor Heterodimer Formation. A Possible Mechanism for Mutual Inhibition of Transcriptional Activity", Journal of Biological Chemistry, 272(22):14087-14092.
Chen et al. (Feb. 27, 2014) "Mechanism of the Reversal Effect of Mifepristone on Drug Resistance of the Human Cervical Cancer Cell Line HELA/MMC", Genetics and Molecular Research, 13(1):1288-1295.
Chi et al. (Oct. 2009) "Castration-Resistant Prostate Cancer: From New Pathophysiology to New Treatment Targets", European Urology, 56(4):594-605.
Cho et al. (Mar. 8, 2005) "Role of Activation Function Domain-1, DNA Binding, and Coactivator GRIP1 in the Expression of Partial Agonist Activity of Glucocorticoid Receptor-Antagonist Complexes", Biochemistry, 44(9):3547-3561.
Clark et al. (Feb. 15, 2008) "1H-Pyrazolo[3,4-g]Hexahydro-Isoguinolines as Selective Glucocorticoid Receptor Antagonists with High Functional Activity", Bioorganic & Medicinal Chemistry Letters, 18(4):1312-1317.
Clark Robin D. (2008) "Glucocorticoid Receptor Antagonists", Current Topics in Medicinal Chemistry, 8(9):813-838.
Cleutjens et al. (Dec. 1997) "Both Androgen Receptor and Glucocorticoid Receptor Are Able to Induce Prostate-Specific Antigen Expression, but Differ in Their Growth-Stimulating Properties of LNCaP Cells", Endocrinology, 138(12):5293-5300.
Colleoni et al. (Aug. 2000) "Response to Primary Chemotherapy in Breast Cancer Patients with Tumors Not Expressing Estrogen and Progesterone Receptors", Annals of Oncology, 11(8):1057-1059.
Hunt et al. (2015) "1H-Pyrazolo[3,4-g]hexahydro-isoquinolines as Potent GR Antagonists with Reduced hERG Inhibition and an Improved Pharmacokinetic Profile", Bioorganic & Medicinal Chemistry Letters, 25(24):5720-5725.
Cossu et al. (Jul. 2005) "The Role of Mifepristone in Meningiomas Management: A Systematic Review of the Literature", BioMed Research International, 2015:267831(11 pages).
Cummings et al. (2019) "Treatment Combinations for Alzheimer's Disease: Current and Future Pharmacotherapy Options", Journal of Alzheimer's Disease, 67(3):779-794.
Damia et al. (Nov. 2009) "Contemporary Pre-clinical Development of Anticancer Agents—What Are the Optimal Preclinical Models?", European Journal of Cancer, 45(16):2768-2781.
Davies et al. (Oct. 1990) "Association of Glucocorticoid Receptors with Prostate Nuclear Sites for Androgen Receptors and with Androgen Response Elements", Journal of Molecular Endocrinology, 5(2):117-127.
De-Bono et al. (May 26, 2011) "Abiraterone and Increased Survival in Metastatic Prostate Cancer", The New England Journal of Medicine, 364(21):1995-2005.
Desmedt et al. (Jun. 1, 2007) "Strong Time Dependence of the 76-Gene Prognostic Signature for Node-Negative Breast Cancer Patients in the TRANSBIG Multicenter Independent Validation Series", Clinical Cancer Research, 13(11):3207-3214.
Di-Lorenzo et al. (2010) "Castration-Resistant Prostate Cancer", Drugs 70(8):983-1000.
Dinkel et al. (Feb. 2003) "Novel Glucocorticoid Effects on Acute Inflammation in the CNS", Journal of Neurochemistry, 84(4):705-716.
Donovan et al. (Feb. 2010) "Androgen Receptor Expression is Associated with Prostate Cancer-Specific Survival in Castrate Patients with Metastatic Disease", BJU International, 105(4):462-467.
Evans et al. (2014) "CNS-Targeted Glucocorticoid Reduces Pathology in Mouse Model of Amyotrophic Lateral Sclerosis", Acta Neuropathologica Communications, 2:66 (13 pages).
Fakih et al. (Oct. 2002) "Glucocorticoids and Treatment of Prostate Cancer: A Preclinical and Clinical Review", Urology, 60(4):553-561.
Fidler et al. (Dec. 25, 2011) "Disease Progression in a Mouse Model of Amyotrophic Lateral Sclerosis: The Influence of Chronic Stress and Corticosterone", The FASEB Journal, 25(12):4369-4377.
Fiorentino et al. (Feb. 2010) "Blood and tissue biomarkers in prostate cancer: state of the art", Urologic Clinics of North America, 37(1):131-141.
Flexner Charles (Dec. 2007) "HIV Drug Development: The Next 25 Years", Nature Reviews, Drug Discovery, 6(12):959-966.
Gaddy et al. (Aug. 1, 2004) "Mifepristone Induces Growth Arrest, Caspase Activation, And Apoptosis Of Estrogen Receptor-Expressing, Antiestrogen-Resistant Breast Cancer Cells", Clinical Cancer Research, 10(15):5215-5225.
Gargiulo-Monachelli et al. (Jun. 2014) "Circulating Gonadal and Adrenal Steroids in Amyotrophic Lateral Sclerosis: Possible Markers of Susceptibility and Outcome", Hormone and Metabolic Research, 46(6):433-439.
Ghoumari et al. (Jun. 2003) "Mifepristone (RU486) Protects Purkinje Cells from Cell Death in Organotypic Slice Cultures of Postnatal Rat and Mouse Cerebellum", Proceedings of the National Academy of Sciences, 100(13):7953-7958.
González Deniselle et al. (Feb. 1997) "Glucocorticoid Receptors and Actions in the Spinal Cord of the Wobbler Mouse, A Model for Neurodegenerative Diseases", Journal of Steroid Biochemistry and Molecular Biology, 60(3-4):205-213.
Grover et al. (Jul. 2002) "The Initiation of Breast and Prostate Cancer", Carcinogenesis, 23(7):1095-1102.
Gulliver, Linda S. M. (Mar. 2017) "Xenobiotics and the Glucocorticoid Receptor", Toxicology and Applied Pharmacology, 319:69-79.

(56) References Cited

OTHER PUBLICATIONS

Guo et al. (Mar. 2009) "A Novel Androgen Receptor Splice Variant Is Up-Regulated During Prostate Cancer Progression and Promotes Androgen Depletion-Resistant Growth", 69(6):2305-2313.
Han et al. (Feb. 2003) "Biochemical (Prostate Specific Antigen) Recurrence Probability Following Radical Prostatectomy for Clinically Localized Prostate Cancer", The Journal of Urology, 169(2):517-523.
He et al. (2015) "Discovery of a Highly Potent Glucocorticoid for Asthma Treatment", Cell Discovery, 1(15035):13 Pages.
Hein et al. (2008) "Click Chemistry, A powerful Tool for Pharmaceutical Sciences", Pharmaceutical Research, 25(10):2216-2230.
Hemmi et al. (2011) "Dramatic Response of Dropped Head Sign to Treatment with Steroid in Parkinson's Disease: Report of Three Cases", Internal Medicine, 50(7):757-761.
Henderson et al. (1998) "Estrogens as a Cause of Human Cancer: the Richard and Hinda Rosenthal Foundation Award Lecture", 48(2):246-253.
Ho et al. (1993) "A Complex Response Element in Intron 1 of the Androgen-Regulated 20-kDa Protein Gene Displays Cell Type-Dependent Androgen Receptor Specificity", Journal of Biological Chemistry, 268(36):27226-27235.
Huang et al. (2010) "Reversal Effect of Mifepristone on Adriamycin Resistance in Human Breast Cancer Cell Line MCF-7/ADM in Vitro and in Vivo", Journal of Central South University (Medical Sciences), 35(6):576-583.
Zhang et al. (Mar. 15, 2006) "Corticosteroid Co-Treatment Induces Resistance to Chemotherapy in Surgical Resections, Xenografts and Established Cell Lines of Pancreatic Cancer", BMC Cancer, 6(61):1-14.
Hunt et al. (2017) "Abstract 3623: Preclinical Efficacy of the Selective GR Antagonist, CORT125134", American Association for Cancer Research, 4 pages.
Zou et al. (Apr. 2009) "Androgen-Induced Coactivator ANCCA Mediates Specific Androgen Receptor Signaling in Prostate Cancer", Cancer Research, 69(8):3339-3346.
Hunt et al. (2017) "Identification of the Clinical Candidate (R)-(1-(4-Fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor", Journal of Medicinal Chemistry, 60(8):3405-3421.
Jannin et al. (2014) "Polyoxylglycerides and Glycerides: Effects of Manufacturing Parameters on API Stability, Excipient Functionality and Processing", International Journal of Pharmaceutics, 466(1-2):109-121.
Jemal et al. (2010) "Cancer Statistics", CA: A Cancer Journal for Clinicians, 60(5):277-300(25 Pages).
Johnson et al. (2001) "Relationships Between Drug Activity in NCI Preclinical in Vitro and in Vivo Models and Early Clinical Trial", British Journal of Cancer, 84(10):1424-1431.
Kach et al. (2015) "Glucocorticoid Receptor Signaling in Breast and Prostate Cancers: Emergence as a Therapeutic Target", Science Translational Medicine, 7(305):9 Pages.
Kach et al. (2017) "Selective Glucocorticoid Receptor Modulators (SGRMs) Delay Castrate-Resistant Prostate Cancer Growth", Molecular Cancer Therapeutics, 16(8):1680-1692.
Kadmiel et al. (2013) "Glucocorticoid Receptor Signaling in Health and Disease", Trends in Pharmacological Sciences, 34(9):518-530.
Keen et al. (2003) "The Biology of Breast Carcinoma", Cancer, 97(3 Suppl):825-833.
Kim et al. (2011) "Current Treatment Strategies for Castration-Resistant Prostate Cancer", Korean Journal of Urology, 52(3):157-165.
Klein et al. (2007) "Analyzing Survival Curves at a Fixed Point in Time", Statistics in Medicine, 26(24):4505-4519.
Klijn et al. (1989) "Antiprogestins a New Form of Endocrine Therapy for Human Breast Cancer", Cancer Research, 49(11):2851-2856.

Kondo (2010) "A Case of Ectopic Adrenocorticotropic Hormone-Producing Pancreatic Neuroendocrine Tumor with Multiple Liver Metastases", Endocrine Journal, 57(3):229-236.
Koochekpour (2010) "Androgen Receptor Signaling and Mutations in Prostate Cancer", Asian Journal of Andrology, 12(5):639-657.
Kriaucionis et al. (2009) "The Nuclear DNA Base 5-Hydroxymethylcytosine is Present in Brain and Enriched in Purkinje Neurons", Science, 24(5929):929-930.
Lante et al. (2015) "Subchronic Glucocorticoid Receptor Inhibition Rescues Early Episodic Memory and Synaptic Plasticity Deficits in a Mouse Model of Alzheimer's Disease", Neuropsychopharmacology, 40(7):1772-1781.
Li et al. (2004) "High Level of Androgen Receptor is Associated with Aggressive Clinicopathologic Features and Decreased Biochemical Recurrence-Free Survival in Prostate: Cancer Patients Treated with Radical Prostatectomy", The American Journal of Surgical Pathology, 28(7):928-934.
Li et al. (2017) "Systemic Overexpression of the 11 B-HSD1 Promotes Endoplasmic Reticulum Stress in Multiple Tissues and the Development of Metabolic Syndrome in Mice", Molecular Medicine Reports, 16(5):7738-7744.
Loi et al. (2007) "Definition of Clinically Distinct Molecular Subtypes in Estrogen Receptor-Positive Breast Carcinomas Through Genomic Grade", Journal of Clinical Oncology, 25(10):1239-1246.
Loi et al. (2008) "Predicting Prognosis Using Molecular Profiling in Estrogen Receptor-Positive Breast Cancer Treated With Tamoxifen", BMC Genomics, 9(239):12 Pages.
Lotan et al. (2007) "Up-Regulation of MKK4, MKK6 and MKK7 During Prostate Cancer Progression: An Important Role for SAPK Signalling in Prostatic Neoplasia", The Journal of Pathology, 212(4):386-394.
Lucci et al. (1999) "Modification of Ceramide Metabolism Increases Cancer Cell Sensitivity to Cytotoxics", International Journal of Oncology, 15(3):541-546.
Ma et al. (2003) "IL-21 Activates Both Innate and Adaptive Immunity to Generate Potent Antitumor Responses that Require Perforin but Are Independent of IFN-Gamma", Journal of Immunology, 171(2):608-615.
Macpherson et al. (2005) "Glucocorticoids Worsen Excitotoxin-Induced Expression of Pro-Infammatory Cytokines in Hippocarnpal Cultures", Experimental Neurology, 194(2):376-383.
Makarov et al. (2007) "Updated Nomogram to Predict Pathologic Stage of Prostate Cancer Given Prostate-Specific Antigen Level, Clinical Stage, and Biopsy Gleason Score (Partin Tables) Based on Cases from 2000 to 2005", Urology, 69(6):1095-1101.
Melhem et al. (2009) "Administration of Glucocorticoids to Ovarian Cancer Patients is Associated with Expression of the Anti-apoptotic Genes SGK1 and MKP1/DUSP1 in Ovarian Tissues", Clinical Cancer Research, 15(9):3196-3204.
Meyer et al. (2018) "The Selective Glucocorticoid Receptor Modulator Cort 113176 Reduces Neurodegeneration and Neuroinflammation in Wobbler Mice Spinal Cord", Neuroscience, 384:384-396.
Meyer et al. (2014) "The Selective Glucocorticoid Receptor Modulator CORT108297 Restores Faulty Hippocampal Parameters in Wobbler and Corticosterone-Treated Mice", The Journal of Steroid Biochemistry and Molecular Biology, 143:40-48.
Mifeprex (Jul. 19, 2005) "Mifepristone", Label, Rev 2, Available Online at: A96. http://web.archive.org/web/20060628212659/http://www.fda.gov/cder/foi/label/2005/020687s0131bl.pdf, 20 pages.
Mikosz et al. (2001) "Glucocorticoid Receptor-Mediated Protection from Apoptosis is Associated with Induction of the Serine/Threonine Survival Kinase Gene, sgk-1", The Journal of Biological Chemistry, 276(20):16649-16654.
Miljkovic et al. (2009) "Methylprednisolone Inhibits IFN-Y and IL-17 Expression and Production by Cells Infiltrating Central Nervous System in Experimental Autoimmune Encephalomyelitis", Journal of Neuroinflammation, 6(37):10 Pages.
Minn et al. (Jul. 28, 2005) "Genes that Mediate Breast Cancer Metastasis to Lung", Nature, 436(7050):518-524(15 pages).
Mohler et al. (May 1996) "Androgen and Glucocorticoid Receptors in the Stroma and Epithelium of Prostatic Hyperplasia and Carcinoma", Clinical Cancer Research, 2(5):889-895.

(56) References Cited

OTHER PUBLICATIONS

Möller et al. (May 2010) "Impact of New Technologies for Cellular Screening Along The Drug Value Chain", Drug Discovery Today, 15(9/10):384-390.

Moran et al. (Feb. 15, 2000) "The Glucocorticoid Receptor Mediates a Survival Signal in Human Mammary Epithelial Cells1", Cancer Research, 60(4):867-872.

Moses et al. (2007) "The Growing Applications of Click Chemistry", Chemical Society Reviews, 36:1249-1262.

Mottet et al. (2011) "EAU Guidelines on Prostate Cancer. Part II: Treatment of Advanced, Relapsing, and Castration-Resistant Prostate Cancer", European Urology, 59(4):572-583.

Munhoz et al. (2006) "Chronic Unpredictable Stress Exacerbates Lipopolysaccharide-Induced Activation of Nuclear Factor-kappaB in the Frontal Cortex and Hippocampus Via Glucocorticoid Secretion", The Journal of Neuroscience, 26(14):3813-3820.

Munster et al. (2018) "A Phase 1/2 Study of Relacorilant + Nab-Paclitaxel (Nabpac) in Patients (Pts) with Solid Tumors: The Dose-Finding Phase", Journal of Clinical Oncology, 36(15):4 Pages.

Niemeier et al. (2010) "Androgen Receptor in Breast Cancer: Expression in Estrogen Receptor-Positive Tumors and in Estrogen Receptor-Negative Tumors with Apocrine Differentiation", Modern Pathology, 23:205-212.

Norman et al. (1994) "Functional Glucocorticoid Receptor Modulates Pancreatic Carcinoma Growth through an Autocrine Loop", Journal of Surgical Research, 57(1):33-38.

Novotny et al. (2003) "Cancer Therapy: New Targets for Chemotherapy", Hematology, 8(3):129-137.

Ocana et al. (2011) "Preclined Development of Molecular-targeted Agents for Cancer", Nature Reviews Clinical Oncology review, 8(4):200-209.

Ohlmann et al. (2012) "Novel Options for the Treatment of Castration-Resistant Prostate Cancer", World Journal of Urology, 30(4):495-503.

Orayj et al. (Nov. 3, 2019) "Patterns and Determinants of Prescribing for Parkinson's Disease: A Systematic Literature Review", Parkinson's Disease, 2019:9237181(40 pages).

Pan et al. (2011) "Activation of the Glucocorticoid Receptor is Associated with Poor Prognosis in Estrogen Receptor-Negative Breast Cancer", Cancer Research, 71(20): 6360-6370.

Pan et al. (Mar. 25, 2010) "Identification of Glucocorticoid Receptor (GR) Signatures in Primary Human Breast Cancer: Association with Relapse-Free Survival Time", Poster Presented by S.D. Conzen as a Short Talk, presented at Nuclear Receptors: Signaling, Gene Regulation and Cancer, Keystone Symposia on Molecular and Cellular Biology, Keystone Resort, Keystone, Colorado, 1 page.

Pang et al. (2006) "Dexamethasone Decreases Xenograft Response to Paclitaxel Through Inhibition of Tumor Cell Apoptosis", Cancer Biology & Therapy, 5(8):933-940.

Panigrahi et al. (2018) "Gelucire: A versatile polymer for modified release drug delivery system", Future Journal of Pharmaceutical Sciences, 4:102-108.

Patacchioli et al. (Dec. 2003) "Adrenal Dysregulation in Amyotrophic Lateral Sclerosis", Journal of Endocrinological Investigation, 26(12):RC23-RC25.

Peeters et al. (Dec. 2008) "Differential Effects of the New Glucocorticoid Receptor Antagonist ORG 34517 and RU486 (Mifepristone) on Glucocorticoid Receptor Nuclear Translocation in the AtT20 Cell Line", Annals of the New York Academy of Sciences, 1148:536-541.

Perini et al. (Feb. 1, 1992) "Effects of Carbamazepine on Pituitary-Adrenal Function in Healthy Volunteers", The Journal of Clinical Endocrinology and Metabolism, 74(2):406-412.

Petrov et al. (Mar. 2017) "ALS Clinical Trials Review: 20 Years of Failre. Are we Any Closer to Registering a New Treatment?", Frontiers in Aging Neuroscience, 9(68):1-11 Pages.

Petrylak et al. (Apr. 19, 2006) "Evaluation of Prostate-Specific Antigen Declines for Surrogacy in Patients Treated on SWOG 99-16", Journal of the National Cancer Institute, 98(8):516-521.

Pike et al. (Jan. 1, 1993) "Estrogens, Progestogens, Normal Breast Cell Proliferation, and Breast Cancer Risk", Epidemiologic Review, 15(1):17-30.

Pomara et al. (May 2002) "Mifepristone (RU 486) for Alzheimer's Disease", Neurology, 58(9):1436-1437.

Pound et al. (May 5, 1999) "Natural History of Progression after PSA Elevation Following Radical Prostatectomy", JAMA, 281(17):1591-1597.

Rakotomamonjy et al. (Jan. 12, 2019) "Brain-Derived Neurotrophic Factor is Required for the Neuroprotctive Effect of Mifepristone on Immature Purkinje Cells in Cerebellar Slice Culture", International Journal of Molecular Sciences, 20(2):9 Pages.

Rauhala et al. (Dec. 2005) "Dual-Specificity Phosphatase 1 and Serum/Glucocorticoid-Regulated Kinase are Downregulated in Prostate Cancer", International Journal of Cancer, 117(5):738-745.

Ring et al. (Dec. 2004) "Mechanisms of Tamoxifen Resistance", Endocrine-Related Cancer, 11(4):643-658.

Robinson et al. (2009) "Octahydrophenanthrene-2,7-diol Analogues as Dissociated Glucocoricoid Receptor Agonists: Discovery and Lead Exploration", Journal of Medicinal Chemistry, 52(6):1731-1743.

Roozendaal et al. (Jan. 2012) "The Cortisol Awakening Response in Amyotrophic Lateral Sclerosis is Blunted and Correlates with Clinical Status and Depressive Mood", Psychoneuroendocrinology, 37(1):20-26.

Rosner et al. (Dec. 2007) "Higher Tumor to Benign Ratio of the Androgen Receptor mRNA Expression Associates with Prostate Cancer Proogression after Radical Prostatectomy", Urology, 70(6):1225-1229.

Sahoo et al. (Nov. 2005) "Coordinate Expression of the PI3-Kinase Downstream Effectors Serum and Glucocorticoid-Induced Kinase (SGK-1) and Akt-1 in Human Breast Cancer", Journal of Cancer, 41(17):2754-2749.

Sahu et al. (Mar. 2013) "FoxA1 Specifies Unique Androgen and Glucocorticoid Receptor Binding Events in Prostate Cancer Cells", Cancer Research, 73(5):1570-1580.

Schenone et al. (2013) "Target Identification and Mechanism of Action in Chemical Biology and Drug Discovery", Nature Chemical Biology, 9(4):232-240.

Scher et al. (Apr. 2010) "Antitumour Activity of Mdv3100 in Castration-Resistant Prostate Cancer: A Phase 1-2 Study", Lancet, 375(9724):1437-1446.

Scher et al. (Nov. 10, 2005) "Biology of Progressive, Castration-Resistant Cancer: Directed Therapies Targeting the Androgen-Receptor Signaling Axis", Journal of Clinical Oncology, 23(32):8253-8261.

Scher et al. (Sep. 20, 2011) "End Points and Outcomes in Castration-Resistant Prostate Cancer: From Clinical Trials to Clinical Practice", Journal of Clinical Oncology, 29(27):3695-3704.

Schlossmacher et al. (Oct. 2011) "Glucocorticoid Receptor-Mediated Apoptosis: Mechanisms of Resistance in Cancer Cells", Journal of Endocrinology, 211(1):17-25.

Segovia-Mendoza et al. (Jan. 27, 2015) "Antihormonal Agents as a Strategy to Improve the Effect of Chemo-Radiation in Cervical Cancer: In Vitro and in Vivo Study", BMC Cancer, 15(21):1-11.

Seruga et al. (Jan. 2011) "Drug Resistance in Metastatic Castration-Resistant Prostate Cancer", Nature Reviews Clinical Oncology, 8(1):12-23.

Shanmugam et al. (Oct. 12, 2007) "Serum/Glucocorticoid-Induced Protein Kinase-1 Facilitates Androgen Receptor-Dependent Cell Survival", Cell Death & Differentiation, 14(12):2085-2094.

Sharma et al. (Apr. 2010) "Cell Line-based Platforms to Evaluate the Therapeutic Efficacy of Candidate Anticancer Agents", Nature Reviews Cancer, 10(4):241-253.

Sherk et al. (Sep. 15, 2008) "Development of a Small Molecule Serum and Glucocorticoid-Regulated Kinase 1 Antagonist and its Evaluation as a Prostate Cancer Therapeutic", Cancer Research, 68(18):7475-7483 (20 pages).

Sims et al. (Sep. 21, 2008 "The Removal of Multiplicative, Systematic Bias Allows Integration of Breast Cancer Gene Expression Datasets-Improving Meta-Analysis and Prediction of Prognosis", BMC Medical Genomics, 1(42):1-14.

(56) References Cited

OTHER PUBLICATIONS

Smith et al. (Dec. 4, 2002) "Expression of Glucocorticoid and Progesterone Nuclear Receptor Genes in Archival Breast Cancer Tissue", Breast Cancer Research, 5(1):R9-R12.
Smith et al. (Sep. 18, 2007), "Progesterone, Glucocorticoid, but not Estrogen Receptor mRNA is Altered in Breast Cancer Stroma", Cancer Letters, 255(1):77-84.
Song et al. (Sep. 2014), "Dihydrotestosterone Enhances Castration-Resistant Prostate Cancer Cell Proliferation through STAT5 Activation via Glucocorticoid Receptor Pathway", The Prostate, 74(12):1240-1248.
Sorlie et al. (Sep. 11, 2001), "Gene Expression Patterns of Breast Carcinomas Distinguish Tumor Subclasses with Clinical Implications", Proceedings of the National Academy of Sciences of the United States of America, 98(19):10869-10874.
Sotiriou et al. (Feb. 15, 2006) "Gene Expression Profiling in Breast Cancer: Understanding the Molecular Basis of Histologic Grade to Improve Prognosis", Journal of the National Cancer Institute, 98(4):262-272.
Spataro et al. (Nov. 2015) "Plasma Cortisol Level in Amyotrophic Lateral Sclerosis", Journal of the Neurological Sciences, 358:282-286.
Srinivas et al. (May 1, 2006) "Phase II Study Evaluating Oral Triamcinolone in Patients with Androgen-Independent Prostate Cancer", Urology, 67(5):1001-1006.
Srinivas et al. (Aug. 2002) "Proteomics for Cancer Biomarker Discovery", Clinical Chemistry, 48(8):1160-1169.
Stephenson et al. (May 17, 2006) "Preoperative Nomogram Predicting the 10-Year Probability of Prostate Cancer Recurrence After Radical Prostatectomy", Journal of the National Cancer Institute, 98(10):715-717.
Sterbis et al. (Feb. 1, 2008) "Higher Expression of the Androgen-Regulated Gene PSA-HK3 mRNA in Prostate Cancer Tissues Predicts Biochemical Recurrence-Free Survival", Clinical Cancer Research, 14(3):758-763.
Stringer-Reasor et al. (Sep. 2015) "Glucocorticoid Receptor Activation Inhibits Chemotherapy-Induced Cell Death in High-Grade Serous Ovarian Carcinoma", Gynecologic Oncology, 138(3):656-662.
Sui et al. (Jun. 1, 2007) "Estrogen Receptor α Mediates Breast Cancer Cell Resistance to Paclitaxel through Inhibition of Apoptotic Cell Death", Cancer Research., 67(11):5337-5344.
Sun et al. (Aug. 2010) "Castration Resistance in Human Prostate Cancer Is Conferred by a Frequently Occurring Androgen Receptor Splice Variant", Journal of Clinical Investigation, 120(8):2715-2730.
Sundahl et al. (Jul. 2016) "Selective Glucocorticoid Receptor-Activating Adjuvant Therapy in Cancer Treatments", Oncoscience, 3(7-8):188-202.
Szmulewitz et al. (Feb. 1, 2012) "Serum/Glucocorticoid-Regulated Kinase 1 Expression in Primary Human Prostate Cancers", Prostate, 72(2):157-164.
Tannock et al. (Oct. 7, 2004) "Docetaxel Plus Prednisone or Mitoxantrone Plus Prednisone for Advanced Prostate Cancer", The New England Journal of Medicine, 351(15):1502-1512.
Taplin et al. (May 2008) "A Phase II Study of Mifepristone (Ru-486) in Castration-Resistant Prostate Cancer, with a Correlative Assessment of Androgen-Related Hormones", BJU International, 101(9):1084-1089.
Tessier et al. (Aug. 15, 2006) "Serum and Glucocorticoid-Regulated Protein Kinases: Variations on a Theme", Journal of Cellular Biochemistry, 98(6):1391-1407.
Tokuda et al. (May 14, 2002) "Prednisolone (30-60 Mg/Day) for Diseases Other than AD Decreases Amyloid beta-peptides in CSF", Neurology, 58(9):1415-1418.
Touat et al. (Oct. 2014 "Successful Treatment of Multiple Intracranial Meningiomas with the Antiprogesterone Receptor Agent Mifepristone (RU486)", Acta Neurochirurgica, 156(10):1831-1835.

Twiddy et al. (Mar. 2011) "Cholesterol as a Potential Target for Castration-Resistant Prostate Cancer", Pharmaceutical Research, 28(3):423-437.
Venkatesh et al. (Feb. 2000) "Role of the Development Scientist in Compound Lead Selection and Optimization", Journal of Pharmaceutical Sciences, 89(2):145-154.
Wang et al. (Feb. 19-25, 2005) "Gene-Expression Profiles to Predict Distant Metastasis of Lymph-Node-Negative Primary Breast Cancer", The Lancet, 365(9460):671-679.
Ward et al. (Apr. 1, 2005) "Rising Prostate-Specific Antigen after Primary Prostate Cancer Therapy", Nature Clinical Practice Urology, 2(4):174-182.
(2004) Wayne Genck, Chemical Processing.com.
West et al. (Feb. 2016) "Abstract PD3-02: Second-generation selective glucocorticoid receptor modulators in triple-negative breast cancer", Cancer Research, Poster Discussion Abstracts, Thirty-Eighth Annual CTRC-AACR, 76(4 Supplement):PD3-02 (2 pages).
Wright et al. (Dec. 2009) "Differences in Prostate Cancer Outcomes Between Cases with Gleason 4+3 and Gleason 3+4 Tumors in a Population Based Cohort", The Journal of Urology, 182(6):2702-2707.
Wu et al. (Oct. 1, 2006) "Glucocorticoid Receptor Activation Signals through Forkhead Transcription Factor 3a in Breast Cancer Cells", Molecular Endocrinology, 20(10):2304-2314.
Wu et al. (Mar. 1, 2004) "Microarray Analysis Reveals Glucocorticoid-Regulated Survival Genes that are Associated with Inhibition of Apoptosis in Breast Epithelial Cells", Cancer Research, 64(5):1757-1764.
Wu et al. (Aug. 16, 2004) "Prevalent Expression of the Immunostimulatory MHC Class I Chain-Related Molecule Is Counteracted by Shedding in Prostate Cancer", Journal of Clinical Investigation, 114(4):560-568.
Yemelyanov et al. (Jan. 15, 2012) "Differential Targeting of Androgen and Glucocorticoid Receptors Induces ER Stress and Apoptosis in Prostate Cancer Cells", Cell Cycle, 11(2):395-406.
Yemelyanov et al. (Mar. 22, 2007) "Tumor Suppressor Activity of Glucocorticoid Receptor in the Prostate", Oncogene, 26(13):1885-1896.
Yu et al. (Jan. 19, 2015) "Systems Pharmacology of Mifepristone (RU486) Reveals its 47 Hub Targets and Network: Comprehensive Analysis and Pharmacological Focus on FAK-Src-Paxillin Complex", Scientific Reports, 5(1):7830(10 pages).
Yves Fradet (May 2009) "Biomarkers in Prostate Cancer Diagnosis and Prognosis: Beyond Prostate-Specific Antigen", Current Opinion in Urology, 19(3);243-246.
Zegarra-Moro et al. (Feb. 15, 2002) "Disruption of Androgen Receptor Function Inhibits Proliferation of Androgen-refractory Prostate Cancer Cells", Cancer Research, 62(4):1008-1013.
Study of Relacorilant in Combination with Nab-Paclitaxel for Patients with Recurrent Platinum-Resistant Ovarian, Fallopian Tube, or Primary Peritoneal Can, ClinicaiTrials.gov, Available online at: https://clinicaltrials.gov/ct2/show/NCT03776812, 11 pages.
Belanoff et al. (Mar. 25, 2011) "Selective Glucocorticoid Receptor (type II) Antagonists prevent Weight Gain caused by Olanzapine in Rats", European Journal of Pharmacology, 655(1-3):117-120.
Bolton et al. (1989) "The Effects of the Anti-Glucocorticoid RU 38486 on Steroid-Mediated Suppression of Experimental Allergic encephalomyelitis (EAE) in the Lewis Rat", Life Sciences, 45(1):97-104.
International Search Report for PCT Application No. PCT/US2005/008049, dated Jun. 15, 2005, 8 pages.
Partial Supplementary European Search Report, Application No. EP13751132.5, dated Sep. 7, 2015, 6 pages.
"Propylene Glycol Monocaprylate Type 11", Capryol® 90, Available Online at: https://www.gattefosse.com/pharmaceuticals-products/capryol-90, May 28, 2017.
"Study of Drug 1 (Enzalutamide) Plus Drug 2 (Relacorilant) for Patients With Prostate Cancer", ClinicalTrials.gov, Available online at: www.clinicaltrials.gov/ct2/show/NCT03674814.
"Study of Relacorilant in Combination with Nab-Paclitaxel for Patients with Recurrent Platinum-Resistant Ovarian, Fallopian Tube, or Primary Peritoneal Can", ClinicalTrials.gov, Available online at: www.clinicaltrials.gov/ct2/show/ NCT03776812.

(56) References Cited

OTHER PUBLICATIONS

"Study to Evaluate Cort125134 in Combination with Nab-Paclitaxel in Patients with Solid Tumors", ' ClinicaiTrials.gov, Available online at: www.clinicaltrials.gov/ct2/show/NCT02762981.

Hunt et al., "Assessment of Safety, Tolerability, Pharmacokinetics, and Pharmacological Effect of Orally Administered CORT125134: An Adaptive, Double-Blind, Randomized, Placebo-Controlled Phase 1 Clinical Study", Clinical Pharmacology in Drug Development, vol. 7, No. 4, 2018, pp. 408-421.

Hunt et al., "Identification of the clinical candidate (R)-(1-(4-fluorophenyl)-6-((1-methyl-1H-pyrazol-4-yl) sulfonyl)-4,4a,5,6,7,8-hexahydro-1H-pyrazolo [3,4g]isoquinolin-4a-yl)(4-(trifluoromethyl)pyridin-2-yl) methanone (CORT125134): a selective glucocorticoid receptor (GR) antagonist", Journal of Medicinal Chemistry, 2017, 60, 3405-3421.

Hunt et al., "Preclinical Efficacy of the Selective GR antagonist, CORT125134", American Association for Cancer Research, 2017, 1 page.

Jannin, V., et al. "Polyoxylglycerides and glycerides: Effects of manufacturing parameters on API stability, excipient functionality and processing." International J of Pharmaceutics. (2014), vol. 466, pp. 109-121. (Year: 2014).

Munster et al., "A Phase 1/2 Study of Relacorilant + Paclitaxel in Patients with Solid Tumors: The Dose-Finding Phase", American Association for Cancer Research, 2018, 1 page.

MYPI2014003289, "Substantive Examination Adverse Report", dated Mar. 30, 2018, 2 pages.

Niemeier et al., "Androgen Receptor in Breast Cancer: Expression in Estrogen Receptor-Positive Tumors and in Estrogen Receptor-Negative Tumors with Apocrine Differentiation", Mod Pathol., vol. 23, No. 2, 2010, pp. 205-212.

Pineau et al., "New selective glucocorticoid receptor modulators reverse amyloid-ß peptide-induced hippocampus toxicity", Nuerobiology of aging, 2016, vol. 45, pp. 109-122.

International Search Report and Written Opinion, Application No. PCT/US2023/069188, dated Oct. 30, 2023.

International Search Report and Written Opinion, Application No. PCT/US2023/076130, dated Feb. 5, 2024.

EP19898009.6, "Extended European Search Report", Sep. 8, 2022, 14 pages.

EP21154665.0, "Extended European Search Report", Apr. 23, 2021, 5 pages.

EP13751132.5, "Extended European Search Report", dated Mar. 21, 2016, 6 pages.

EP13793417.0, "Extended European Search Report", dated Jan. 4, 2016, 7 pages.

PCT/US2019/067108, "International Preliminary Report on Patentability", Jul. 1, 2021.

\* cited by examiner

METHODS OF PREPARING HETEROARYL-KETONE FUSED AZADECALIN GLUCOCORTICOID RECEPTOR MODULATORS

CROSS-REFERENCES TO RELATED APPLICATIONS

This application claims the benefit of foreign priority to PCT Application No. PCT/CN2020/139524, filed Dec. 25, 2020, which is incorporated herein in its entirety for all purposes.

BACKGROUND

There are two types of high-affinity receptors for corticosteroids; the type I (mineralocorticoid receptor, MR) and the type II (glucocorticoid receptor (GR), or cortisol receptor, GR). In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these include the ligand binding domain, GR-beta is unable to bind ligand, is constitutively localized in the nucleus, and is transcriptionally inactive. The GR is also known as the GR-II.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129). Relacorilant (CORT-125134) is another such glucocorticoid receptor modulator compound, and has been described previously in PCT Publication No. WO 2013/177559, and U.S. Pat. No. 8,859,774. What is needed in the art are new methods of preparing relacorilant having lower impurity content. Surprisingly, the present invention meets these and other needs.

BRIEF SUMMARY OF THE INVENTION

In some embodiments, the present invention provides a method of preparing a compound of Formula J:

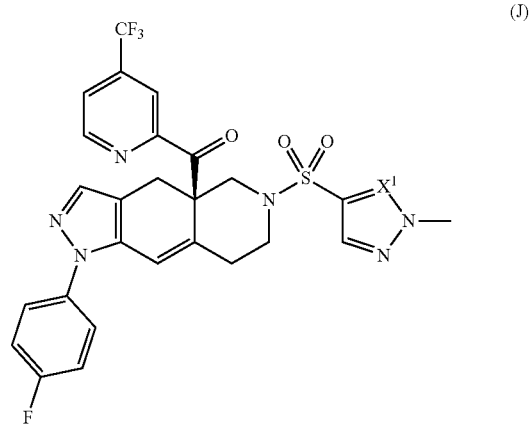

(J)

or a pharmaceutically acceptable salt thereof, comprising:

(a) forming a first reaction mixture comprising a compound of Formula IIb:

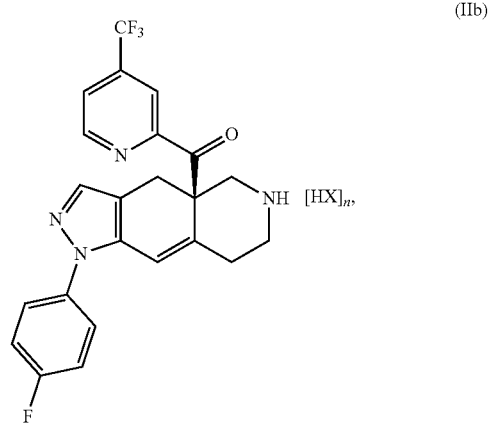 [SMILES: O=C(c1cc(C(F)(F)F)ccn1)[C@@]12CNCCC1=Cc1c(cnn1-c1ccc(F)cc1)C2]

(IIb)

and
a sulfonyl chloride:

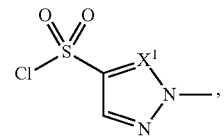

to prepare the compound of Formula J in a yield of at least 60% and a purity of at least 98%, wherein $X^1$ is —CH= or —N=;

HX is an acid solvate; and subscript n is from 1 to 4.

In some embodiments, the present invention provides a method of preparing a compound of Formula I:

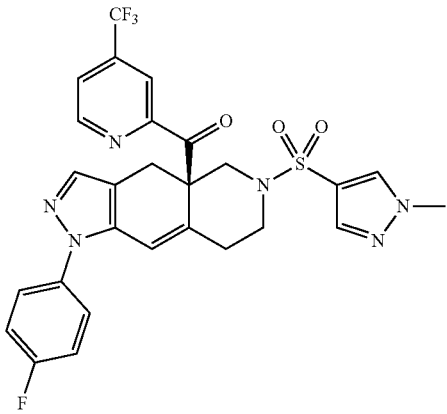

(I)

or a pharmaceutically acceptable salt thereof, comprising:
(a) forming a first reaction mixture comprising a compound of Formula IIb:

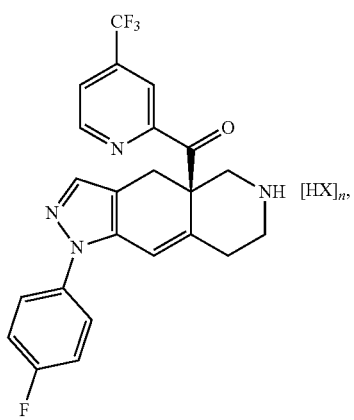

(IIb)

and
1-methyl-1H-pyrazole-4-sulfonyl chloride:

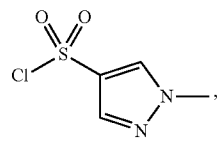

to prepare the compound of Formula I in a yield of at least 60% and a purity of at least 98%,
wherein
HX is an acid solvate; and
subscript n is from 1 to 4.

In some embodiments, the present invention provides a method of preparing a compound of Formula I:

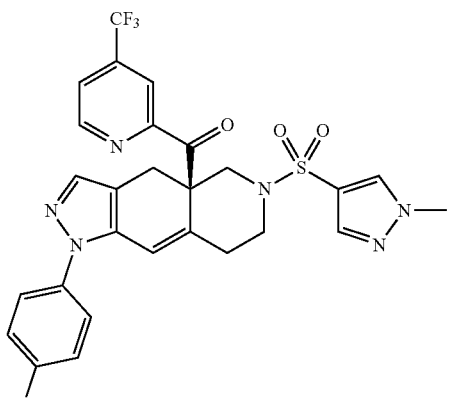

(I)

or a pharmaceutically acceptable salt thereof, comprising:
(a) forming a first reaction mixture comprising a compound of Formula IIb-1:

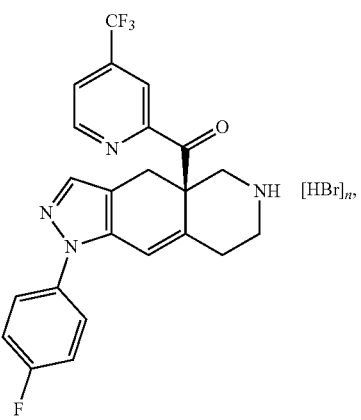

(IIb-1)

and
1-methyl-1H-pyrazole-4-sulfonyl chloride:

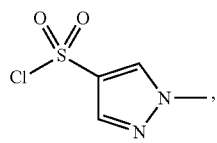

to prepare the compound of Formula I in a yield of at least 60% and a purity of at least 98%, wherein the compound of Formula I contains less than 1% (w/w) of a compound of Formula X-5:

(X-5)

and wherein subscript n is from 1 to 4.

In some embodiments, the present invention provides a method of purifying a compound of Formula I:

(I)

or a pharmaceutically acceptable salt thereof, comprising:
 (a) eluting the compound of Formula I through a High Pressure Liquid Chromatography C18 column using
  (i) a first mobile mixture comprising water in an amount of at least 95% (v/v), formic acid in an amount of 0.05 to 0.2% (v/v), and acetonitrile in an amount of 1 to 5% (v/v),
  (ii) a second mobile mixture comprising water in an amount of 45 to 55% (v/v), formic acid in an amount of 0.01 to 0.1% (v/v), and acetonitrile in an amount of 45 to 55% (v/v), and
  (iii) a third mobile phase comprising water in an amount of 5 to 15% (v/v), formic acid in an amount of 0.005 to 0.02% (v/v), and acetonitrile in an amount of at least 85% (v/v),
 to form an eluted mixture comprising the compound of Formula I having a purity of at least 98% and the compound of Formula X-5 in an amount of less than 0.75% (w/w):

(X-5)

(a1) extracting the compound of Formula I from the eluted mixture into ethyl acetate to form an extracted mixture;
 (a2) mixing the extracted mixture with methyl t-butyl ether (MTBE) under vacuum to form an MTBE mixture comprising less than 5% (v/v) ethyl acetate;
 (d) filtering the MTBE mixture through a filter to form a filtered MTBE mixture comprising:
  the compound of Formula I,
  the compound of Formula X-5 in an amount of less than 0.5% (w/w),
  a compound of Formula X-4 in an amount of less than 0.3% (w/w):

(X-4)

and
 a compound of Formula X-6 in an amount of less than 0.25% (w/w):

(X-6)

(e) adding the filtered MTBE mixture to heptane to form a precipitated compound of Formula I, wherein the precipitated compound of Formula I comprises less than 20 ppm of 1,4-dibromopentane;

(f) dissolving the precipitated compound of Formula I in methanol to form a methanol mixture; and (g) adding the methanol mixture to water to precipitate the purified compound of Formula I, wherein the purified compound of Formula I has a purity of at least 99%, and comprises the compound of Formula X-5 in an amount of less than 0.5% (w/w), 1,4-dibromopentane in an amount of less than 6 ppm, methyl-1-methyl-1H-pyrazole-4-sulfonate in an amount of less than 6 ppm:

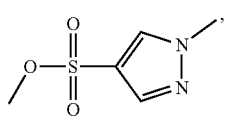

and 1-methyl-1H-pyrazole-4-sulfonyl chloride in an amount of less than 6 ppm:

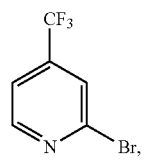

In some embodiments, the present invention provides a method of preparing a compound of Formula IIa:

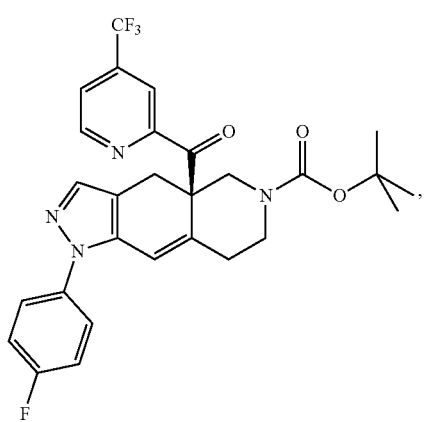

comprising the step of:

(c) forming a third reaction mixture comprising a Grignard reagent, a compound of Formula III:

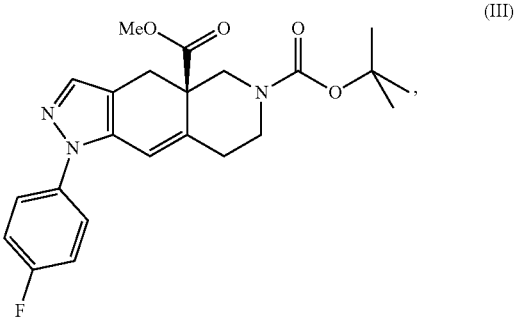 [SMILES: COC(=O)[C@]12Cc3cnn(-c4ccc(F)cc4)c3C=C1CCN(C(=O)OC(C)(C)C)C2]

and 2-bromo-4-(trifluoromethyl)pyridine:

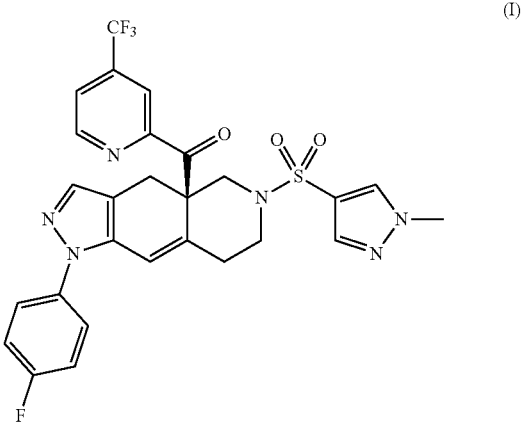

wherein the pyridine is present in a molar ratio of 1.0 to 1.5 to the compound of Formula III, and wherein the Grignard reagent is present in a molar ratio of 1.5 to 1.7 to the compound of Formula III, to prepare the compound of Formula IIa.

In some embodiments, the present invention provides a method of preparing a compound of Formula I:

or a pharmaceutically acceptable salt thereof, comprising:
(a) forming a fourth reaction mixture comprising a compound of Formula IIb-2:

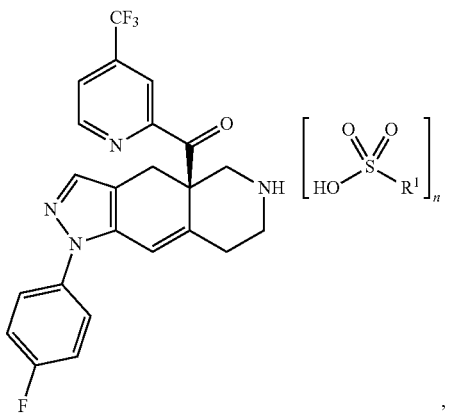

and 1-methyl-1H-pyrazole-4-sulfonyl chloride:

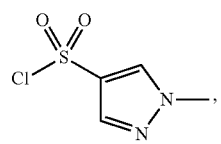

to prepare the compound of Formula I in a yield of at least 75% and a purity of at least 98%,
wherein
R¹ is $C_{1-6}$ alkyl, $C_{1-10}$ haloalkyl, phenyl, or 4-methylphenyl; and
subscript n is 1 to 4.

In some embodiments, the present invention provides a method of preparing a compound of Formula IIb-2:

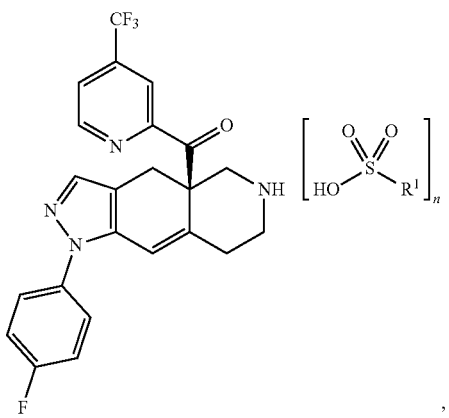

comprising:
(b) forming a fifth reaction mixture comprising a compound of Formula IIa:

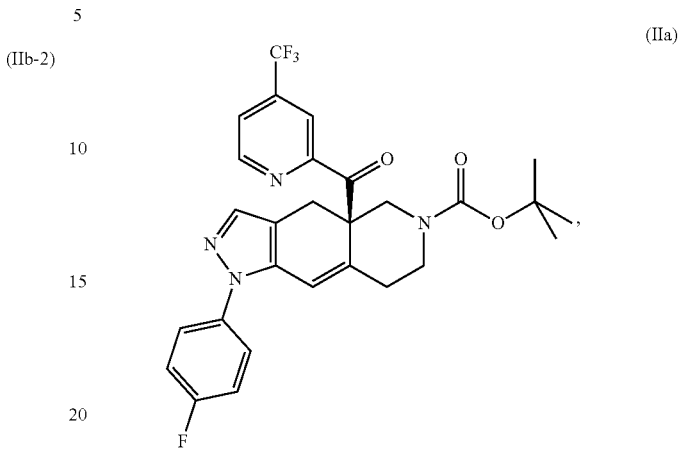

and
a sulfonic acid of the formula:

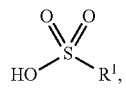

to form the compound of Formula IIb-2,
wherein
R¹ is $C_{1-6}$ alkyl, $C_{1-10}$ haloalkyl, phenyl, or 4-methylphenyl; and
subscript n is 1 to 4.

In some embodiments, the present invention provides a composition comprising:
a compound of Formula I in an amount of at least 99% (w/w):

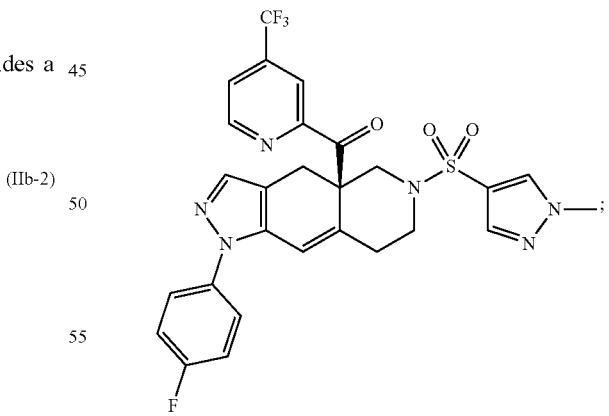

and
one or more impurity in an amount of from 0.01 to 1% (w/w).

In some embodiments, the present invention provides a crystalline form of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid:

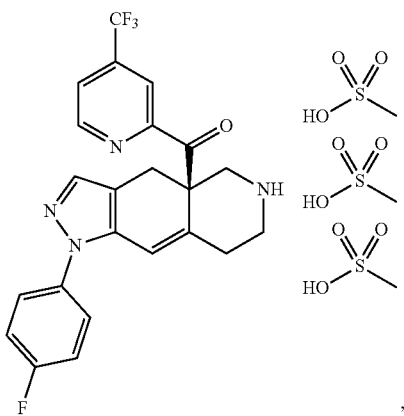

characterized by an X-ray powder diffraction (XRPD pattern having peaks at about 18.2°, 18.3°, and 19.7° 2-θ±0.2° 2-θ.

DETAILED DESCRIPTION OF THE INVENTION

I. General

Figure 1:
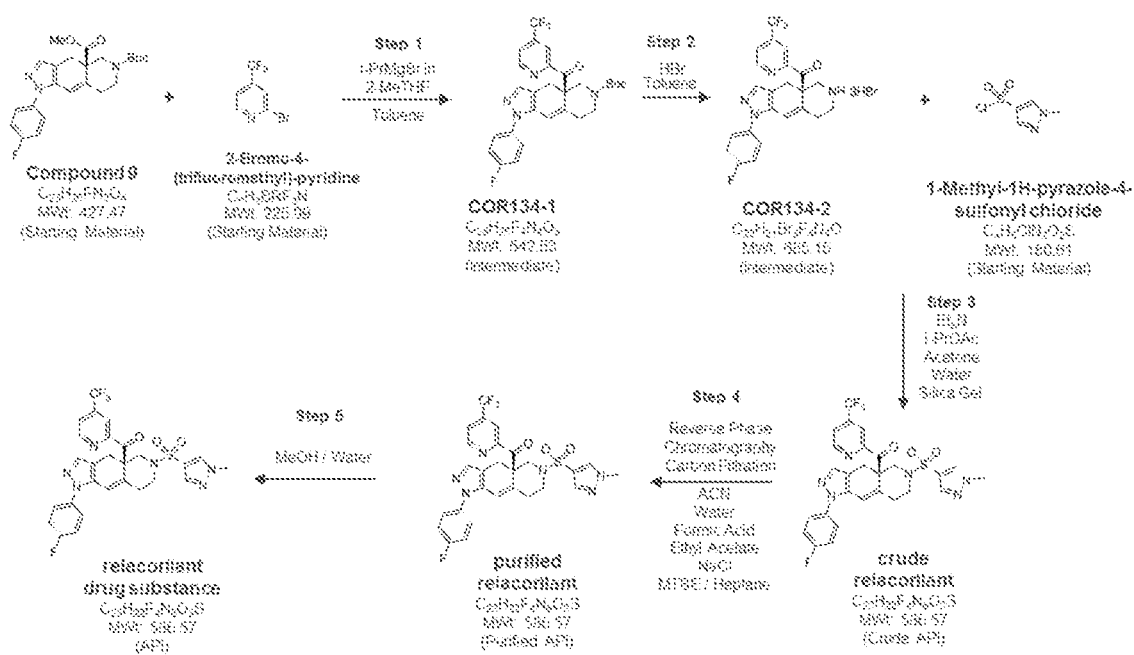
FIG. 1 shows the synthetic scheme for preparing (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid (relacorilant) according to Example 3.

The instant disclosure describes new methods of preparing the compound of Formula I, (R)-(1-(4-fluorophenyl)-6-((1-methyl-1H-pyrazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone (relacorilant), having lower impurity levels than the methods previously described. Relacorilant can also be named (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, as in Example 18 of U.S. Pat. No. 8,859,774. The instant disclosure also describes compositions of relacorilant that have lower impurity levels.

II. Definitions

"About" when referring to a value includes the stated value+/−10% of the stated value. For example, about 50% includes a range of from 45% to 55%, while about 20 molar equivalents includes a range of from 18 to 22 molar equivalents. Accordingly, when referring to a range, "about" refers to each of the stated values+/−10% of the stated value of each end of the range. For instance, a ratio of from about 1 to about 3 (weight/weight) includes a range of from 0.9 to 3.3.

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Dissolve", "dissolving" or "dissolution" refers to a solid material that is substantially soluble in a particular solvent. For example, the solid material can be greater than 90% soluble in the solvent, or greater than 91, 92, 93, 94, 95, 96, 97, 98, or greater than 99% soluble in the solvent.

"Distilling", "distill" or "distillation" refers to the separation of components in a liquid mixture using a combination of temperature and pressure. The target component is converted from a liquid to a gas followed by condensing the gas back to a liquid to separate the target component from the other components of the mixture.

"Eluting", "elute" or "elution" refers to the process of separating a target component from other components in a mixture by passing the mixture over a stationary phase. The target component is eluted from the stationary phase using a mobile phase that can include any suitable solvent or acid.

"Precipitate", "precipitated" or "precipitation" refers to a solid formed from a solution, such as adding a first solvent in which a compound is dissolved to an excess of a second solvent in which the compound is not substantially soluble such that the dissolved compound comes out of solution and forms a solid.

"Substantially free" refers to a composition having an undesired component in an amount less than 5%, less than 1%, less than 0.5% or even less than 0.1% by weight.

"Aqueous phase" refers to a mixture containing water.

"Organic phase" refers to a mixture containing water-miscible or -immiscible solvents capable of dissolving either or both of water-soluble and water-insoluble organic compounds. The organic phase of the present invention can formed from one or more organic solvents. Exemplary organic solvents can be non-polar aprotic solvents, polar aprotic solvents, and polar protic solvents. Representative solvents include, but are not limited to, pentanes, hexanes, hexane, heptanes, benzene, toluene, diethyl ether, tetrahydrofuran, acetone, ethyl acetate, acetonitrile, methylene chloride, chloroform, etc.

"Acid" refers to a compound that is capable of donating a proton ($H^+$) under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, camphorsulfonic acid, among others.

"Grignard reagent" refers to a reagent containing a complex of magnesium metal, a halide, and an alkyl ligand, capable of forming a carbon-carbon bond. Representative Grignard reagents include, but are not limited to, iPrMgCl and iPrMgBr.

"Non-nucleophilic base" refers to a base that is a moderate to strong base but at the same time is a poor nucleophile. Representative non-nucleophilic bases include bases such as potassium carbonate, sodium carbonate, potassium tert-butoxide, and sodium tert-butoxide, as well as amine bases, such as triethylamine, diisopropylethyl amine, N,N-diethylaniline, pyridine, 2,6-lutidine, 2,4,6-collidine, 4-dimethylaminopyridine, and quinuclidine. This includes non-nucleophilic amine bases.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, diethyl ether, 1,4-dioxane, acetone, ethyl acetate, dimethylformamide, dimethylacetamide, acetonitrile and dimethyl sulfoxide. Representative non-polar solvents include alkanes (pentanes, hexanes, etc.), cycloalkanes (cyclopentane, cyclohexane, etc.), benzene, and toluene. Other solvents are useful in the present invention.

"Room temperature" is the range of air temperatures generally considered to be suitable for human occupancy, or between about 15 degrees Celsius (59 degrees Fahrenheit) and 25 degrees Celsius (77 degrees Fahrenheit).

"Vacuum" or "reduced pressure" refers to a pressure that is less than atmospheric pressure. Atmospheric pressure is measured as about 1013 mbar, 760 mm Hg, or about 14.7 psi. Accordingly, vacuum can be less than 1013 mbar, or less than 100, 10, 1, 0.1, or less than 0.01 mbar.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. The term "perfluoro" can be used to define a compound or radical where all the hydrogens are replaced with fluorine. For example, perfluoromethyl refers to 1,1,1-trifluoromethyl.

"Pharmaceutically acceptable salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier(s), diluent(s) or excipient(s) must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, surfactants, coatings, sweeteners, flavors and colors. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

A cortisol receptor is a glucocorticoid receptor (GR), specifically the type II GR, which specifically binds cortisol and/or cortisol analogs such as dexamethasone (See, e.g., Turner & Muller, J. Mol. Endocrinol. Oct. 1, 2005 35 283-292).

"Mineralocorticoid receptor" (MR) refers to a type I glucocorticoid receptor (GR I), which is activated by aldosterone in humans.

"Glucocorticoid receptor modulator" (GRM) refers to any compound which modulates any biological response associated with the binding of a glucocorticoid receptor to an agonist. As used herein, with respect to a GRM, the glucocorticoid receptor may be GR, or both. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, inhibits the agonist-induced increase in the activity of tyrosine aminotransferase (TAT) in HepG2 cells. TAT activity can be measured as outlined in the literature by A. Ali et al., J. Med. Chem., 2004, 47, 2441-2452.

"Glucocorticoid receptor antagonist" (GRA) refers to any compound which inhibits any biological response associated with the binding of a glucocorticoid receptor to an agonist. As used herein, with respect to a GRA, the glucocorticoid receptor may be GR, or both. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. An inhibitor is a compound with an $IC_{50}$ (half maximal inhibition concentration) of less than 10 micromolar. See Example 1 of U.S. Pat. No. 8,685,973, the entire contents of which is hereby incorporated by reference in its entirety.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Antagonize' and "antagonizing" refer to inhibiting the binding of an agonist at a receptor molecule or to inhibiting the signal produced by a receptor-agonist. A receptor antagonist inhibits or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulator of the present invention. In some embodiments, examples of disorders or conditions include, but are not limited to, fatty liver disease, nonalcoholic fatty liver disease (NAFLD), nonalcoholic steatohepatitis (NASH), and antipsychotic-induced weight gain.

"Fatty liver disease" refers to a disease or a pathological condition caused by, at least in part, abnormal hepatic lipid deposits. Fatty liver disease includes, e.g., alcoholic fatty liver disease, nonalcoholic fatty liver disease, and acute fatty liver of pregnancy. Fatty liver disease may be, e.g., macrovesicular steatosis or microvesicular steatosis.

"Non-alcoholic fatty liver disease" ("NAFLD") refers to one of the types of fatty liver disease which occurs when fat is deposited (steatosis) in the liver due to causes other than excessive alcohol use. NAFLD is considered to cover a spectrum of disease activity. This spectrum begins as fatty accumulation in the liver (hepatic steatosis). Most people with NAFLD have few or no symptoms. Patients may complain of fatigue, malaise, and dull right-upper-quadrant abdominal discomfort. Mild jaundice may be noticed, although this is rare. More commonly NAFLD is diagnosed following abnormal liver function tests during routine blood tests. By definition, alcohol consumption of over 20 g/day (about 25 ml/day of net ethanol) excludes the condition.

"Non-alcoholic steatohepatitis" ("NASH") refers to the most extreme form of NAFLD. NAFLD can progress to become non-alcoholic steatohepatitis (NASH), a state in which steatosis is combined with inflammation and fibrosis (steatohepatitis). NASH is a progressive disease. Over a 10-year period, up to 20% of patients with NASH will develop cirrhosis of the liver, and 10% will suffer death related to liver disease.

"Substance use disorder" refers to the compulsive use of a substance despite unpleasant or harmful consequences of that use. A substance use disorder may involve impaired control (e.g., use of excessive amounts of the substance, or over longer periods of time, than was originally intended), social impairment (e.g., failure to fulfill major roles obligations at work, school, or home), risky use (e.g., recurrent use of the substance in situations in which it is physically hazardous), and pharmacological criteria (e.g., tolerance or withdrawal). A substance use disorder may have formerly been termed an "addiction" although, since the publication of the *Diagnostic and Statistical Manual of Mental Disor-* ders *Fifth Edition DSM*-5 (hereafter "DSM-V"), terms such as "addiction" and "addict" have been replaced for the terms "substance use disorder" (replacing "addiction") and person suffering from a substance use disorder (replacing "addict"). A person suffering from a substance use disorder may be termed as suffering from a substance use disorder related to a particular substance; prior to the publication of DSM-V, such a person may have been described as being "addicted to" that substance. For example, where a person has a substance use disorder related to a stimulant, that person may have been described as being "addicted to" that stimulant prior to the publication of DSM-V.

"Substance" as recited in phrases such as "substance use disorder related to said substance" and "substance use disorder related to the substance" refers to the substance for which a patient has a craving, or which the patient uses compulsively despite unpleasant or harmful consequences of that use. Thus, such a "substance" is the substance used by, or ingested, or otherwise administered to (including self-administration) a person who suffers from a substance use disorder related to that substance. The terms "substance of addiction", and "substance of abuse" may have formerly been used to refer such a substance, which substance may formerly have been termed an "addictive substance" (e.g., prior to the publication of DSM-V).

"Person suffering from a substance use disorder" refers to a person suffering from a substance use disorder related to a particular substance, or, in some cases, more than one particular substance. Such a "substance" may be a drug, or alcohol, or a cigarette, or other substance a person may take (ingest). For example, such a "substance" may be alcohol, a stimulant, an opioid, or other substance.

III. Method of Preparing Formula I from Formula IIb-1

The present invention provides methods for preparing compounds of Formula J:

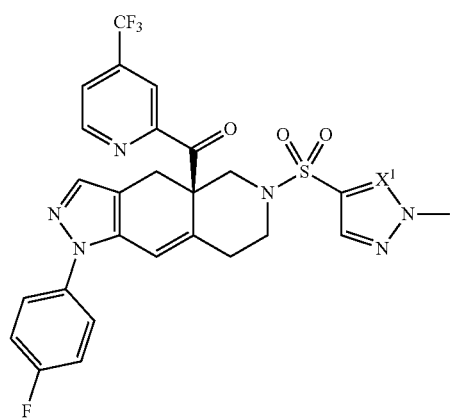

or a pharmaceutically acceptable salt thereof, comprising:
(a) forming a first reaction mixture comprising a compound of Formula IIb:

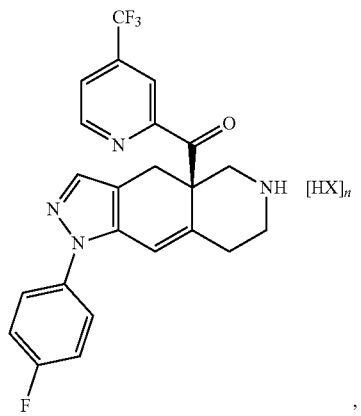

and
a sulfonyl chloride:

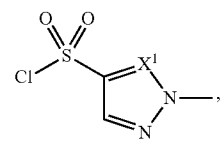

to prepare the compound of Formula J in a yield of at least 60% and a purity of at least 98%,
wherein
X$^1$ is —CH═ or —N═;
HX is an acid solvate; and
subscript n is from 1 to 4.
In some embodiments, X$^1$ of Formula J is —CH═.

The present invention provides methods for preparing the compound of Formula I, (R)-(1-(4-fluorophenyl)-6-((1-methyl-1H-pyrazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone (relacorilant):

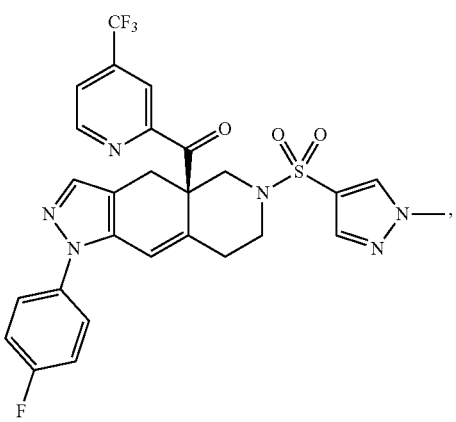

and the compound of Formula Ia, (R)-(1-(4-fluorophenyl)-6-((2-methyl-2H-1,2,3-triazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone:

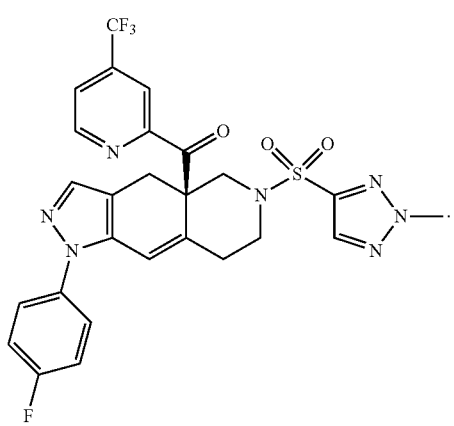

(Ia)

The compound of Formula I (relacorilant; CORT125134) and Formula Ia are described in PCT Publication No. WO 2013/177559, and U.S. Pat. No. 8,859,774.

In some embodiments, the present invention provides a method of preparing a compound of Formula I:

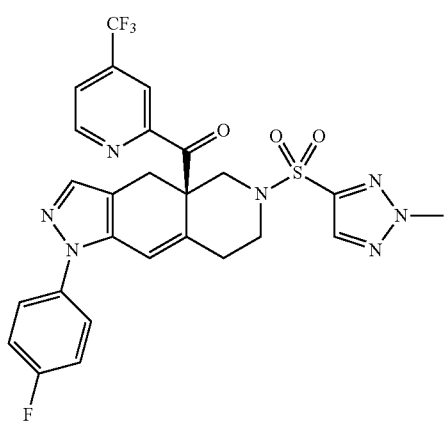

(I)

or a pharmaceutically acceptable salt thereof, comprising:
(a) forming a first reaction mixture comprising a compound of Formula IIb:

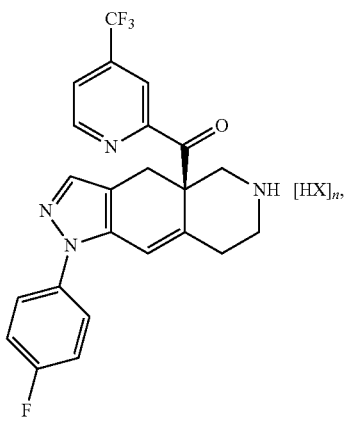

(IIb)

and
1-methyl-1H-pyrazole-4-sulfonyl chloride:

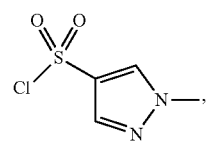

to prepare the compound of Formula I in a yield of at least 60% and a purity of at least 98%,
wherein
HX is an acid solvate; and
subscript n is from 1 to 4.
In some embodiments, HX is HCl, HBr,

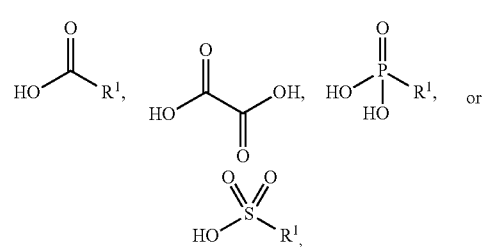

wherein $R^1$ is $C_{1-6}$ alkyl, $C_{1-10}$ haloalkyl, phenyl, or 4-methylphenyl.

In some embodiments, the compound of Formula IIb can have the structure:

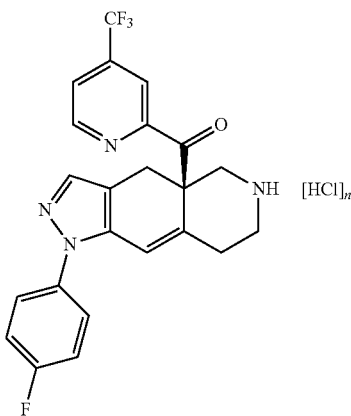 [SMILES: O=C(c1cc(C(F)(F)F)ccn1)[C@@]12CNCCC1=Cc1c(cnn1-c1ccc(F)cc1)C2]

wherein subscript n is from 1 to 4.

In some embodiments, the compound of Formula IIb can have the structure:

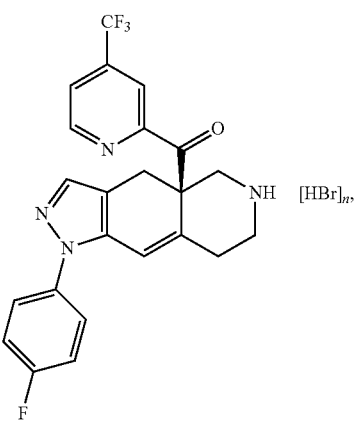 [SMILES: O=C(c1cc(C(F)(F)F)ccn1)[C@@]12CNCCC1=Cc1c(cnn1-c1ccc(F)cc1)C2]

wherein subscript n is from 1 to 4.

In some embodiments, the compound of Formula IIb can have the structure:

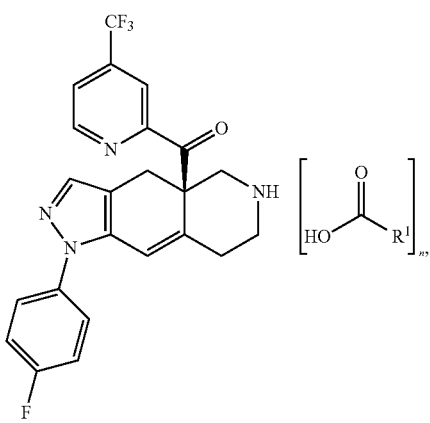

wherein $R^1$ is $C_{1-6}$ alkyl, $C_{1-10}$ haloalkyl, phenyl, or 4-methylphenyl; and subscript n is from 1 to 4.

In some embodiments, the compound of Formula IIb can have the structure:

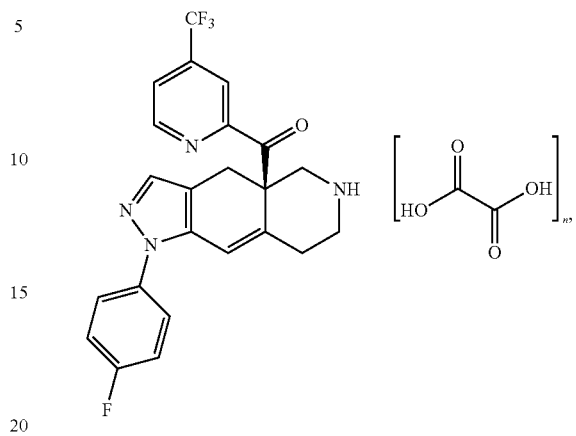

wherein subscript n is from 1 to 4.

In some embodiments, the compound of Formula IIb can have the structure:

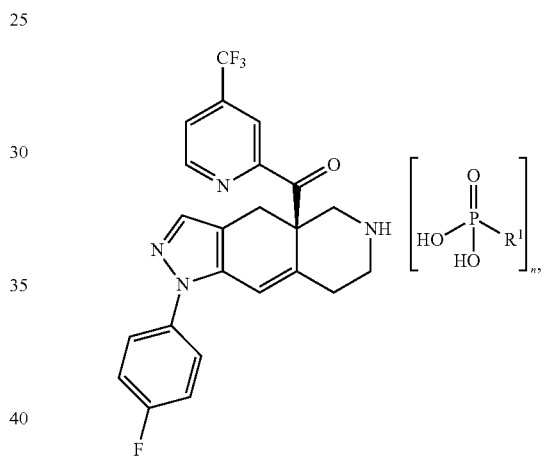

wherein $R^1$ is $C_{1-6}$ alkyl, $C_{1-10}$ haloalkyl, phenyl, or 4-methylphenyl; and subscript n is from 1 to 4.

In some embodiments, the compound of Formula IIb can have the structure:

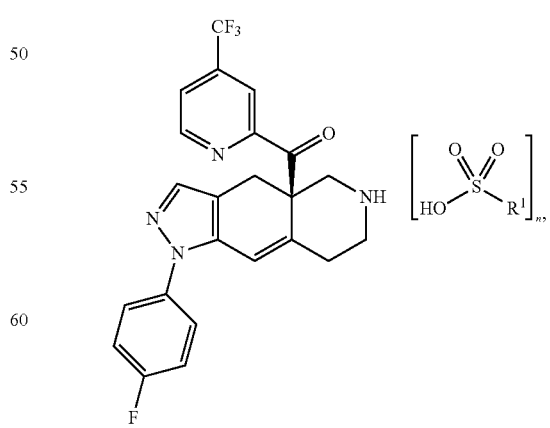

wherein $R^1$ is $C_{1-6}$ alkyl, $C_{1-10}$ haloalkyl, phenyl, or 4-methylphenyl; and subscript n is from 1 to 4.

A. Preparing Formula I from Formula IIb-1

In some embodiments, HX is HBr. The compound of Formula I can be prepared from the compound of Formula IIb-1:

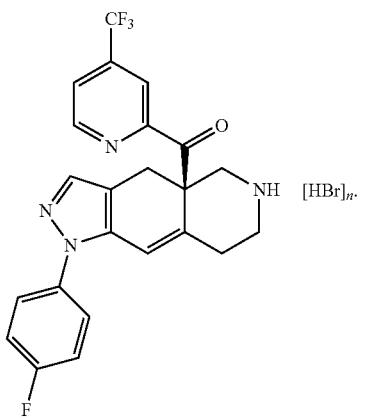
(IIb-1)

In some embodiments, the present invention provides a method of preparing a compound of Formula I:

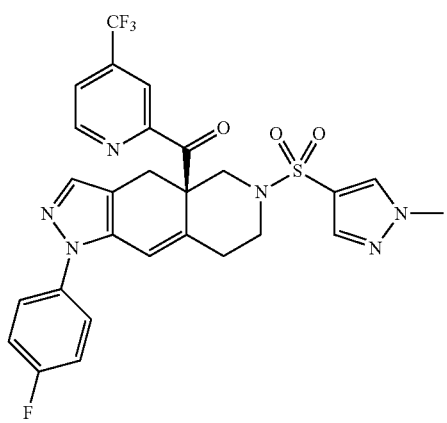
(I)

or a pharmaceutically acceptable salt thereof, comprising:

(a) forming a first reaction mixture comprising a compound of Formula IIb-1:

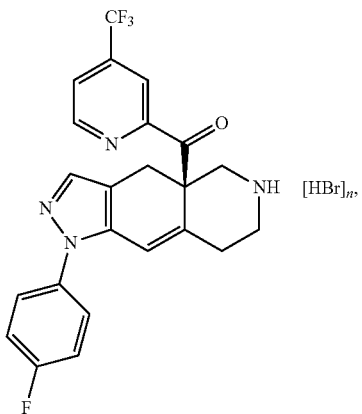
(IIb-1)

and
1-methyl-1H-pyrazole-4-sulfonyl chloride:

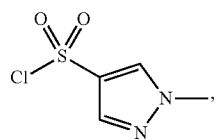

to prepare the compound of Formula I in a yield of at least 60% and a purity of at least 98%, wherein the compound of Formula I contains less than 1% (w/w) of a compound of Formula X-5:

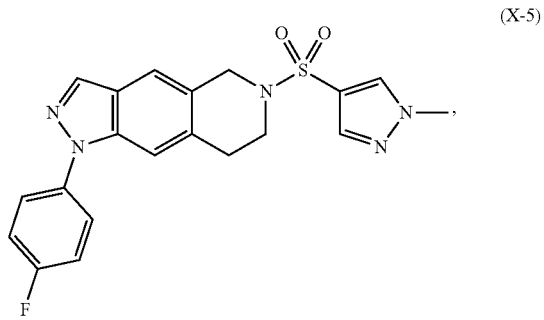 [SMILES: Cn1cc(S(=O)(=O)N2CCc3cc4c(cnn4-c4ccc(F)cc4)cc3C2)cn1]
(X-5)

and wherein subscript n is from 1 to 4.

Subscript n can be 1, 1.5, 2, 2.5, 3, 3.5 or 4. In some embodiments, subscript n is 1. In some embodiments, subscript n is 2. In some embodiments, subscript n is 3. In some embodiments, subscript n is 4. In some embodiments, the compound of Formula IIb-1 has the structure:

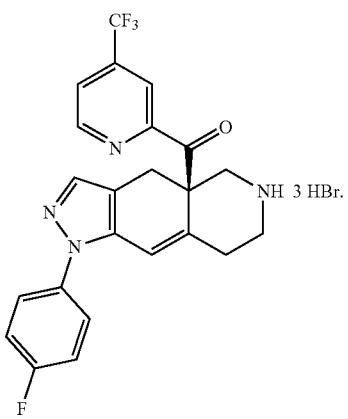

In some embodiments, the first reaction mixture further comprises a non-nucleophilic amine base. Any suitable non-nucleophilic amine base can be used in the first reaction mixture. In some embodiments, the non-nucleophilic amine base comprises trimethylamine, triethylamine, N,N-diisopropyl ethylamine (DIPEA), N,N-dimethyl isopropylamine (DIMPA), 1-ethylpiperidine, N-methylmorpholine, N-methylpyrrolidine, pyridine, N,N-dimethylaniline, N,N-diethylaniline, 2,6-lutidine, 2,4,6-collidine, 4-dimethyl aminopyridine (DMAP), quinuclidine, 4-pyrrolidinopyridine, 1,4-diazabicyclo[2.2.2]octane (DABCO), or mixtures thereof. In some embodiments, the non-nucleophilic amine base comprises triethylamine.

The first reaction mixture can include any suitable solvent. For example, the solvent can be an organic solvent including, but not limited to, ethyl acetate, isopropylacetate, and n-butyl acetate. In some embodiments, the first reaction mixture further comprises a first solvent. In some embodiments, the first solvent includes ethyl acetate, isopropyl acetate, or n-butyl acetate. In some embodiments, the first reaction mixture further comprises isopropyl acetate.

The sulfonyl chloride used in the first reaction mixture can be present in any suitable molar ratio to the compound of Formula IIb-1. For example, the sulfonyl chloride can be present in a molar ratio of from 1.0 to 3.0 to the compound of Formula IIb-1, from 1.0 to 2.5, from 1.0 to 2.0, from 1.0 to 1.5, from 1.1 to 2.4, or from 1.2 to 2.3 to the compound of Formula IIb-1. In some embodiments, the sulfonyl chloride is present in a molar ratio of 1.2 to 2.3 to the compound of Formula IIb-1. The sulfonyl chloride can be present in a molar ratio of 1.0, 1.1, 1.2, 1.3, 1.4, 1.5, 1.6, 1.7, 1.8, 1.9, 2.0, 2.1, 2.2 or 2.3 to the compound of Formula IIb-1. In some embodiments, the sulfonyl chloride can be present in a molar ratio of about 1.2 to the compound of Formula IIb-1.

The compound of Formula I can be prepared in any suitable yield. For example, the compound of Formula I can be prepared in a yield of at least 10, 20, 30, 40, 50, 60, 65, 70, 75, 80, 85, 90, or at least 95%. In some embodiments, the compound of Formula I can be prepared in a yield of at least 60%.

The compound of Formula I can be prepared in any suitable purity. For example, the compound of Formula I can be prepared in a purity of at least 90%, or 91, 92, 93, 94, 95, 96, 97, 98, or at least 99%. In some embodiments, the compound of Formula I can be prepared in a purity of at least 96%. In some embodiments, the compound of Formula I can be prepared in a purity of at least 97%. In some embodiments, the compound of Formula I can be prepared in a purity of at least 98%. In some embodiments, the compound of Formula I can be prepared in a purity of at least 99%.

The compound of Formula I can be prepared with any acceptable amount of a compound of Formula X-4:

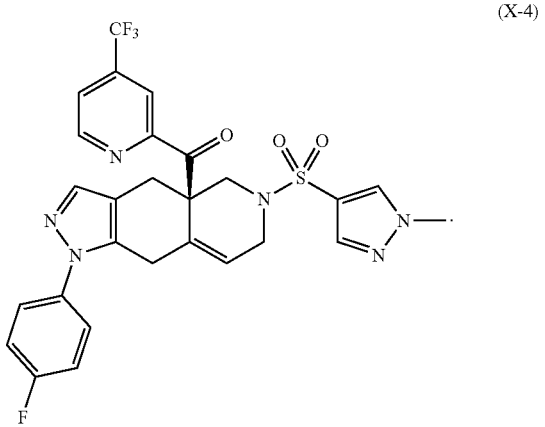 [SMILES: Cn1cc(S(=O)(=O)N2CC=C3Cc4c(cnn4-c4ccc(F)cc4)C[C@]3(C(=O)c3cc(C(F)(F)F)ccn3)C2)cn1]

(X-4)

For example, the compound Formula I can be prepared containing less than 5% (w/w), or 4, 3, 2, 1, 0.9, 0.8, 0.75, 0.7, 0.6, 0.5, 0.4, 0.3, 0.25, 0.2, or less than 0.1% (w/w) of the compound of Formula X-4. In some embodiments, the compound of Formula I can be prepared containing less than 0.5% (w/w) of the compound of Formula X-4. In some embodiments, the compound of Formula I can be prepared containing less than 0.3% (w/w) of the compound of Formula X-4. In some embodiments, the compound of Formula I can be prepared containing less than 0.1% (w/w) of the compound of Formula X-4.

The compound of Formula I can be prepared with any acceptable amount of Formula X-5. For example, the compound Formula I can be prepared containing less than 5% (w/w), or 4, 3, 2, 1, 0.9, 0.8, 0.75, 0.7, 0.6, 0.5, 0.4, 0.3, 0.25, 0.2, or less than 0.1% (w/w) of the compound of Formula X-5. In some embodiments, the compound of Formula I can be prepared containing less than 1% (w/w) of the compound of Formula X-5. In some embodiments, the compound of Formula I can be prepared containing less than 0.75% (w/w) of the compound of Formula X-5. In some embodiments, the compound of Formula I can be prepared containing less than 0.5% (w/w) of the compound of Formula X-5. In some embodiments, the compound of Formula I can be prepared containing less than 0.2% (w/w) of the compound of Formula X-5.

The compound of Formula I can be prepared with any acceptable amount of a compound of Formula X-6:

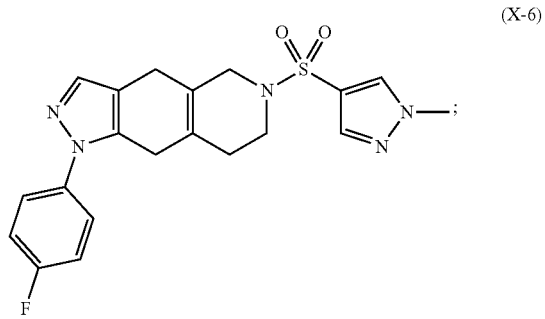 [SMILES: Cn1cc(S(=O)(=O)N2CCC3=C(Cc4cnn(-c5ccc(F)cc5)c4C3)C2)cn1]

(X-6)

For example, the compound Formula I can be prepared containing less than 5% (w/w), or 4, 3, 2, 1, 0.9, 0.8, 0.75, 0.7, 0.6, 0.5, 0.4, 0.3, 0.25, 0.2, or less than 0.1% (w/w) of the compound of Formula X-6. In some embodiments, the compound of Formula I can be prepared containing less than 0.25% (w/w) of the compound of Formula X-6. In some embodiments, the compound of Formula I can be prepared containing less than 0.2% (w/w) of the compound of Formula X-6. In some embodiments, the compound of Formula I can be prepared containing less than 0.1% (w/w) of the compound of Formula X-6.

The compound of Formula I can be prepared with 1,4-diboromopentane in an amount of less than 10 ppm. For example, the compound of Formula I can be prepared with an amount of 1,4-dibromopentane in an amount of less than 10 ppm, or less than 10, 9, 8, 7, 6, 5, or less than 4 ppm. In some embodiments, the compound of Formula I can be prepared with an amount of 1,4-dibromopentane in an amount of less than 8 ppm. In some embodiments, the compound of Formula I can be prepared with an amount of 1,4-dibromopentane in an amount of less than 6 ppm. In some embodiments, the compound of Formula I can be prepared with an amount of 1,4-dibromopentane in an amount of less than 4 ppm.

The compound of Formula I can be prepared with methyl-1-methyl-1H-pyrazole-4-sulfonate:

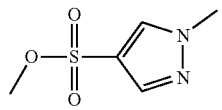

in an amount of less than 10 ppm. For example, the compound of Formula I can be prepared with an amount of methyl-1-methyl-1H-pyrazole-4-sulfonate in an amount of less than 10 ppm, or less than 10, 9, 8, 7, 6, 5, or less than 4 ppm. In some embodiments, the compound of Formula I can be prepared with an amount of methyl-1-methyl-1H-pyrazole-4-sulfonate in an amount of less than 8 ppm. In some embodiments, the compound of Formula I can be prepared with an amount of methyl-1-methyl-1H-pyrazole-4-sulfonate in an amount of less than 6 ppm. In some embodiments, the compound of Formula I can be prepared with an amount of methyl-1-methyl-1H-pyrazole-4-sulfonate in an amount of less than 4 ppm.

The compound of Formula I can be prepared with ethyl-1-methyl-1H-pyrazole-4-sulfonate:

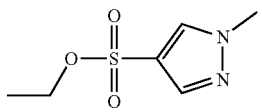

in an amount of less than 10 ppm. For example, the compound of Formula I can be prepared with an amount of ethyl-1-methyl-1H-pyrazole-4-sulfonate in an amount of less than 10 ppm, or less than 10, 9, 8, 7, 6, 5, or less than 4 ppm. In some embodiments, the compound of Formula I can be prepared with an amount of ethyl-1-methyl-1H-pyrazole-4-sulfonate in an amount of less than 8 ppm. In some embodiments, the compound of Formula I can be prepared with an amount of ethyl-1-methyl-1H-pyrazole-4-sulfonate in an amount of less than 6 ppm. In some embodiments, the compound of Formula I can be prepared with an amount of ethyl-1-methyl-1H-pyrazole-4-sulfonate in an amount of less than 4 ppm.

The compound of Formula I can be prepared with isopropyl-1-methyl-1H-pyrazole-4-sulfonate:

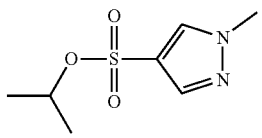

in an amount of less than 10 ppm. For example, the compound of Formula I can be prepared with an amount of isopropyl-1-methyl-1H-pyrazole-4-sulfonate in an amount of less than 10 ppm, or less than 10, 9, 8, 7, 6, 5, or less than 4 ppm. In some embodiments, the compound of Formula I can be prepared with an amount of isopropyl-1-methyl-1H-pyrazole-4-sulfonate in an amount of less than 8 ppm. In some embodiments, the compound of Formula I can be prepared with an amount of isopropyl-1-methyl-1H-pyrazole-4-sulfonate in an amount of less than 6 ppm. In some embodiments, the compound of Formula I can be prepared with an amount of isopropyl-1-methyl-1H-pyrazole-4-sulfonate in an amount of less than 4 ppm.

The compound of Formula I can be prepared with 1-methyl-1H-pyrazole-4-sulfonyl chloride:

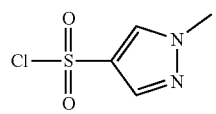

in an amount of less than 10 ppm. For example, the compound of Formula I can be prepared with an amount of 1-methyl-1H-pyrazole-4-sulfonyl chloride in an amount of less than 10 ppm, or less than 10, 9, 8, 7, 6, 5, or less than 4 ppm. In some embodiments, the compound of Formula I can be prepared with an amount of 1-methyl-1H-pyrazole-4-sulfonyl chloride in an amount of less than 8 ppm. In some embodiments, the compound of Formula I can be prepared with an amount of 1-methyl-1H-pyrazole-4-sulfonyl chloride in an amount of less than 6 ppm. In some embodiments, the compound of Formula I can be prepared with an amount of 1-methyl-1H-pyrazole-4-sulfonyl chloride in an amount of less than 4 ppm.

In some embodiments, the method of preparing the compound of Formula I includes:

(a) forming the first reaction mixture comprising the compound of Formula IIb-1, triethylamine, and 1-methyl-1H-pyrazole-4-sulfonyl chloride:

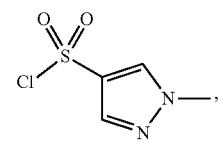

wherein the sulfonyl chloride is present in the molar ratio of about 1.2 to the compound of Formula IIb-1, to prepare the compound of Formula I in the yield of at least 60% and the purity of at least 98%, wherein the compound of Formula I contains less than 1% (w/w) of the compound of Formula X-5:

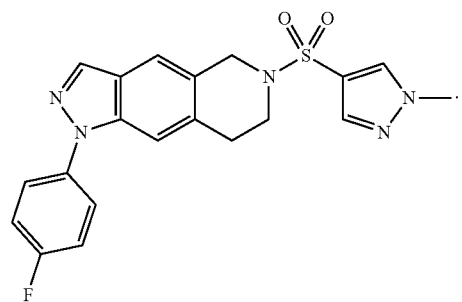

(X-5)

In some embodiments, the method of preparing the compound of Formula I also includes after step (a):

(a1) mixing the first reaction mixture with water having a pH of between 4 and 5 to form a first organic phase and a first aqueous phase;

(a2) mixing the first organic phase with water and sodium chloride wherein the water has a pH of between 5 and 6; and (a3) mixing the first organic phase and silica gel.

The organic phase can include any suitable organic solvent. In some embodiments, the first organic phase includes the first solvent.

Any suitable silica gel can be used in the method of the present invention. Representative silica gel include, but are not limited to, 200-300 mesh silica gel, or 60-80 mesh, 80-120 mesh, 100-200 mesh, etc. In some embodiments, the silica gel is 200-300 mesh silica gel.

B. Preparing Formula IIb-1 from Formula IIa

The compound of Formula IIb-1 can be prepared by a variety of methods. In some embodiments, the compound of Formula IIb-1 is prepared by the step of:
(b) forming a second reaction mixture comprising a compound of Formula IIa:

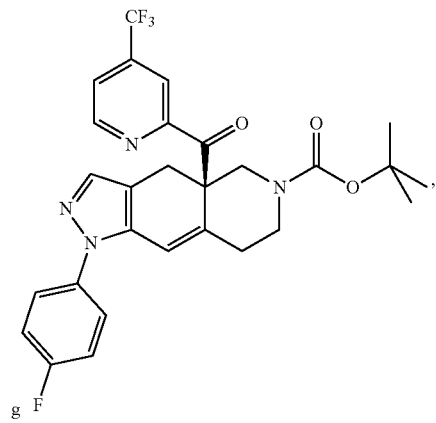

(IIa)

and gaseous HBr, to form the compound of Formula IIb-1 having the structure:

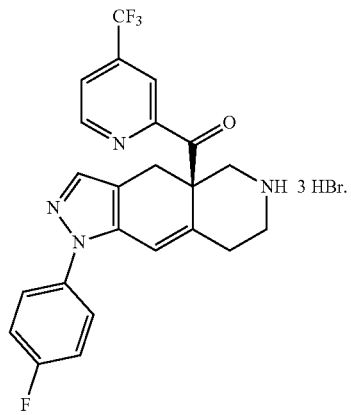

The gaseous HBr can be present in any suitable partial pressure.

The second reaction mixture can also include a second solvent. The second solvent can be any suitable solvent including, but not limited to, tetrahydrofuran, 2-methyltetrahydrofuran, toluene or xylene. In some embodiments, the second reaction mixture further comprises a second solvent. In some embodiments, the second solvent can be tetrahydrofuran, 2-methyltetrahydrofuran, toluene or xylene. In some embodiments, the second reaction mixture further comprises toluene.

The compound of Formula I can be prepared from the compound of Formula IIa. The compound of Formula IIa corresponds to Intermediate 29 of U.S. Pat. No. 8,859,974, (R)-tert-butyl 1-(4-chlorophenyl)-4a-(4-(trifluoromethyl)picolinoyl)-4a,5,7,8-tetrahydro-1H-pyrazolo[3,4-g]isoquinoline-6(4H)-carboxylate. The compound of Formula IIa can also be named tert-butyl (R)-1-(4-fluorophenyl)-4a-(4-(trifluoromethyl)picolinoyl)-1,4,4a,5,7,8-hexahydro-6H-pyrazolo[3,4-g]isoquinoline-6-carboxylate. In some embodiments, the compound of Formula I is prepared by the steps of:
(b) forming the second reaction mixture comprising a compound of Formula IIa:

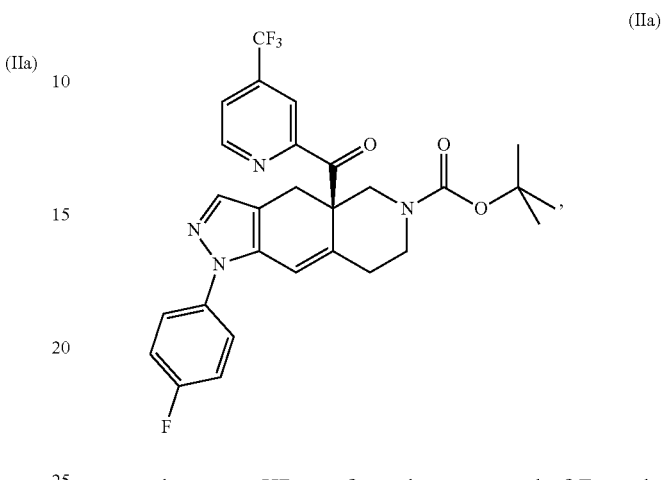

(IIa)

and gaseous HBr, to form the compound of Formula IIb-1 having the structure:

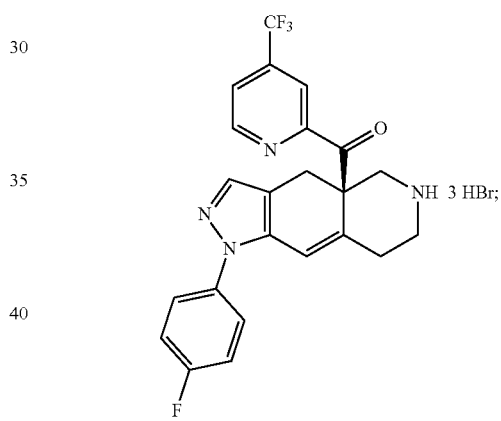

and
(a) forming the first reaction mixture comprising the compound of Formula IIb-1: triethylamine, and 1-methyl-1H-pyrazole-4-sulfonyl chloride:

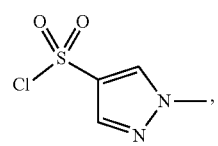

wherein the sulfonyl chloride is present in a molar ratio of about 1.2 to the compound of Formula IIb-1;
(a1) mixing the first reaction mixture with water having a pH of between 4 and 5 to form a first organic phase and a first aqueous phase;
(a2) mixing the first organic phase with water and sodium chloride wherein the water has a pH of between 5 and 6; and
(a3) mixing the first organic phase and silica gel to prepare the compound of Formula I in a yield of at least 60% and a purity of at least 98%, wherein the compound of Formula I contains less than 1% (w/w) of the compound of Formula X-5:

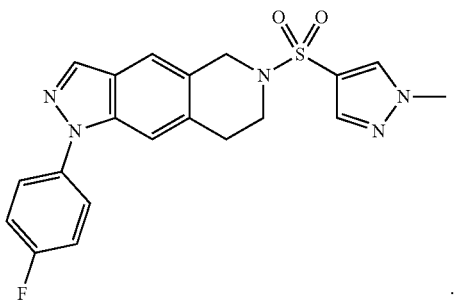

(X-5)

C. Preparing Formula IIa from Formula III

The compound of Formula IIa can be prepared by any suitable method. In some embodiments, the compound of Formula IIa is prepared by:

(c) forming a third reaction mixture comprising a Grignard reagent, a compound of Formula III:

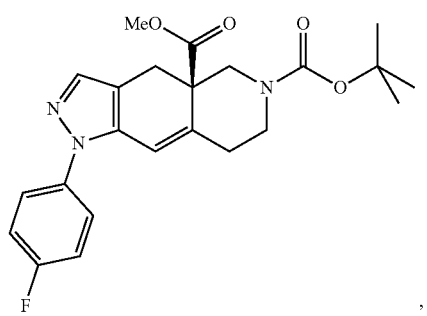

(III)

and
2-bromo-4-(trifluoromethyl)pyridine:

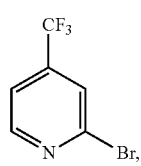

wherein the pyridine is present in a molar ratio of 1.0 to 1.5 to the compound of Formula III, and wherein the Grignard reagent is present in a molar ratio of 1.5 to 1.7 to the compound of Formula III, to prepare the compound of Formula IIa.

Additional embodiments for preparing the compound of Formula IIa are described below in Section IV.

In some embodiments, the method of preparing the compound of Formula I comprises:

(c) forming the third reaction mixture comprising iPrMgBr, 2-methyltetrahydrofuran, toluene, the compound of Formula III:

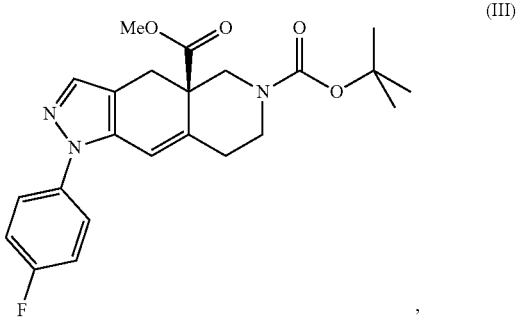 [SMILES: COC(=O)[C@]12Cc3cnn(-c4ccc(F)cc4)c3C=C1CCN(C(=O)OC(C)(C)C)C2]

(III)

and
2-bromo-4-(trifluoromethyl)pyridine:

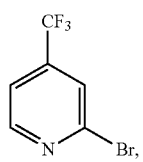

wherein the pyridine is present in the molar ratio of about 1.4 to the compound of Formula III, and wherein the Grignard reagent is present in the molar ratio of about 1.65 to the compound of Formula III, to prepare the compound of Formula IIa:

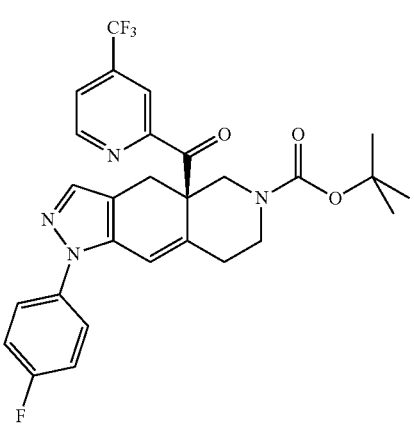

(IIa)

(c1) adding acetic acid and water to the third reaction mixture to form a workup mixture;

(c2) distilling the workup mixture to form an intermediate mixture comprising the compound of Formula IIa, 2-methyltetrahydrofuran in an amount of less than 100 ppm, and water in an amount of less than 0.5% (w/w);

(b) forming the second reaction mixture comprising the intermediate mixture and gaseous HBr, to form the compound of Formula IIb-1 having the structure:

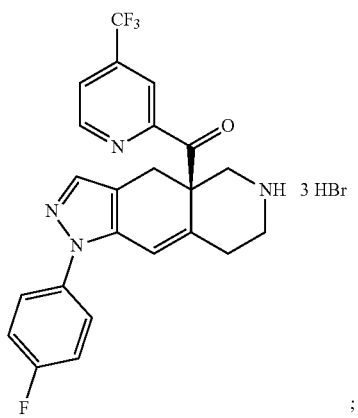 [SMILES: O=C(c1cc(C(F)(F)F)ccn1)[C@@]12CNCCC1=Cc1c(cnn1-c1ccc(F)cc1)C2 ; "3 HBr"]

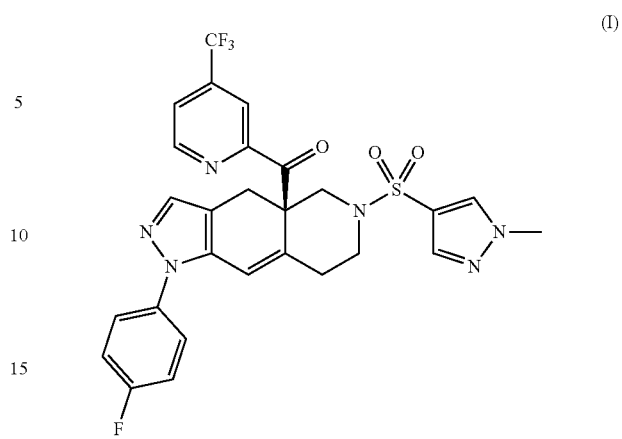

and (a) forming the first reaction mixture comprising the compound of Formula IIb-1, triethylamine, and 1-methyl-1H-pyrazole-4-sulfonyl chloride:

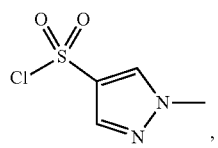

wherein the sulfonyl chloride is present in the molar ratio of about 1.2 to the compound of Formula IIb-1, to prepare the compound of Formula I in the yield of at least 60% and the purity of at least 98%, wherein the compound of Formula I contains less than 1% (w/w) of the compound of Formula X-5:

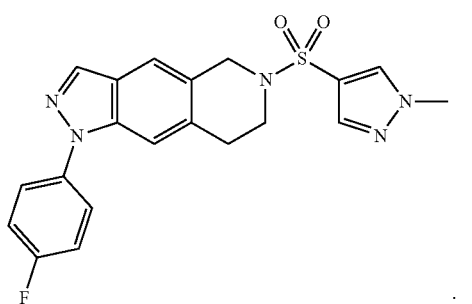

In some embodiments, the method of preparing the compound of Formula I comprises following step (a):

(a1) mixing the first reaction mixture with water having the pH of between 4 and 5 to form the first organic phase and the first aqueous phase;

(a2) mixing the first organic phase with water and sodium chloride wherein the water has the pH of between 5 and 6; and (a3) mixing the first organic phase and silica gel.

D. Purification of the Compound of Formula I

The compound of Formula I can be purified by a variety of methods. In some embodiments, the present invention provides a method of purifying a compound of Formula I:

or a pharmaceutically acceptable salt thereof, comprising:
(a) eluting the compound of Formula I through a High Pressure Liquid Chromatography C18 column using
(i) a first mobile mixture comprising water in an amount of at least 95% (v/v), formic acid in an amount of 0.05 to 0.2% (v/v), and acetonitrile in an amount of 1 to 5% (v/v),
(ii) a second mobile mixture comprising water in an amount of 45 to 55% (v/v), formic acid in an amount of 0.01 to 0.1% (v/v), and acetonitrile in an amount of 45 to 55% (v/v), and
(iii) a third mobile phase comprising water in an amount of 5 to 15% (v/v), formic acid in an amount of 0.005 to 0.02% (v/v), and acetonitrile in an amount of at least 85% (v/v),
to form an eluted mixture comprising the compound of Formula I having a purity of at least 98% and the compound of Formula X-5 in an amount of less than 0.75% (w/w):

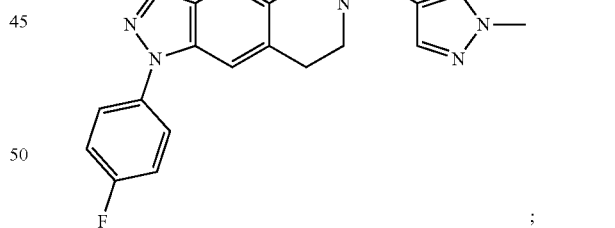

(a1) extracting the compound of Formula I from the eluted mixture into ethyl acetate to form an extracted mixture;
(a2) mixing the extracted mixture with methyl t-butyl ether (MTBE) under vacuum to form an MTBE mixture comprising less than 5% (v/v) ethyl acetate;
(d) filtering the MTBE mixture through a filter to form a filtered MTBE mixture comprising:
the compound of Formula I,
the compound of Formula X-5 in an amount of less than 0.5% (w/w),
a compound of Formula X-4 in an amount of less than 0.3% (w/w):

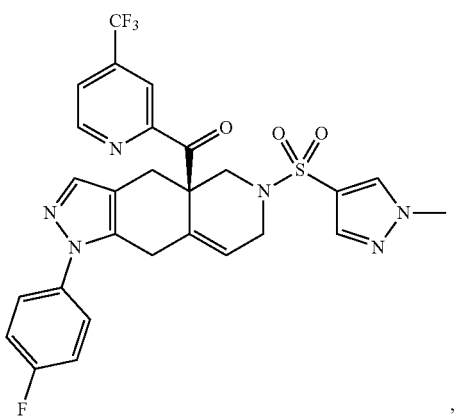

and
a compound of Formula X-6 in an amount of less than 0.25% (w/w):

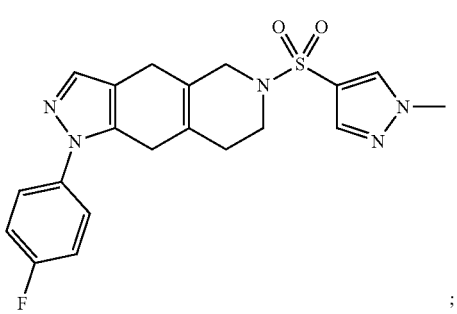

(e) adding the filtered MTBE mixture to heptane to form a precipitated compound of Formula I, wherein the precipitated compound of Formula I comprises 1,4-dibromopentane in an amount of less than 20 ppm;

(f) dissolving the precipitated compound of Formula I in methanol to form a methanol mixture; and (g) adding the methanol mixture to water to precipitate the purified compound of Formula I, wherein the purified compound of Formula I has a purity of at least 99%, and comprises the compound of Formula X-5 in an amount of less than 0.5% (w/w), 1,4-dibromopentane in an amount of less than 6 ppm, methyl-1-methyl-1H-pyrazole-4-sulfonate in an amount of less than 6 ppm:

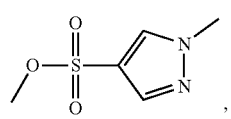

and
1-methyl-1H-pyrazole-4-sulfonyl chloride in an amount of less than 6 ppm:

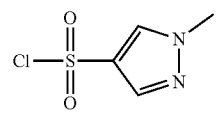

Any suitable filter can be used in the purification method of the present invention. For example, the filter can be a cartridge filter. In some embodiments, the filter can be a CUNO cartridge filter.

In some embodiments, the purified compound of Formula I has a purity of at least 99%, and comprises 1,4-dibromopentane in an amount of less than 8 ppm.

In some embodiments, the purified compound of Formula I has a purity of at least 99%, and further comprises methyl bromide in an amount of less than 20 ppm, and 2-bromopropane in an amount of less than 20 ppm. In some embodiments, the purified compound of Formula I has a purity of at least 99%, and further comprises methyl bromide in an amount of less than 8 ppm, and 2-bromopropane in an amount of less than 8 ppm. In some embodiments, the purified compound of Formula I has a purity of at least 99%, and comprises methyl bromide in an amount of less than 8 ppm, 2-bromopropane in an amount of less than 8 ppm, and 1,4-dibromopentane in an amount of less than 8 ppm.

In some embodiments, the purified compound of Formula I has a purity of at least 99%, and comprises
the compound of Formula X-4 in an amount of less than 0.1% (w/w),
the compound of Formula X-5 in an amount of less than 0.2% (w/w),
the compound of Formula X-6 in an amount of less than 0.2% (w/w),
1,4-dibromopentane in an amount of less than 4 ppm,
1-methyl-1H-pyrazole-4-sulfonyl chloride in an amount of less than 4 ppm, and
methyl 1-methyl-1H-pyrazole-4-sulfonate in an amount of less than 4 ppm.

In some embodiments, the purified compound of Formula I has a purity of at least 99%, and further comprises
ethyl 1-methyl-1H-pyrazole-4-sulfonate in an amount of less than 6 ppm:

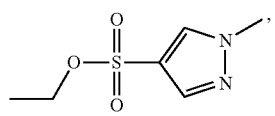

and
isopropyl 1-methyl-1H-pyrazole-4-sulfonate in an amount of less than 6 ppm:

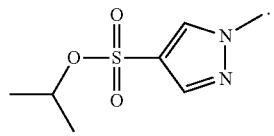

In some embodiments, the purified compound of Formula I has a purity of at least 99%, and further comprises
the compound of Formula X-4 in an amount of less than 0.1% (w/w), the compound of Formula X-5 in an amount of less than 0.2% (w/w), the compound of Formula X-6 in an amount of less than 0.2% (w/w), methyl bromide in an amount of less than 4 ppm, 2-bromopropane in an amount of less than 4 ppm, 1,4-dibromopentane in an amount of less than 4 ppm, 1-methyl-1H-pyrazole-4-sulfonyl chloride in an amount of less than 4 ppm, methyl 1-methyl-1H-pyrazole-4-sulfonate in an amount of less than 4 ppm, ethyl 1-methyl-1H-pyrazole-4-sulfonate in an amount of less than 4 ppm, and isopropyl 1-methyl-1H-pyrazole-4-sulfonate in an amount of less than 4 ppm.

The compound of Formula I purified by the method above can be prepared by the methods described above.

IV. Method of Preparing Formula IIA from Formula III

The compound of Formula IIa can be prepared by any suitable method. In some embodiments, the present invention provides a method of preparing a compound of Formula IIa:

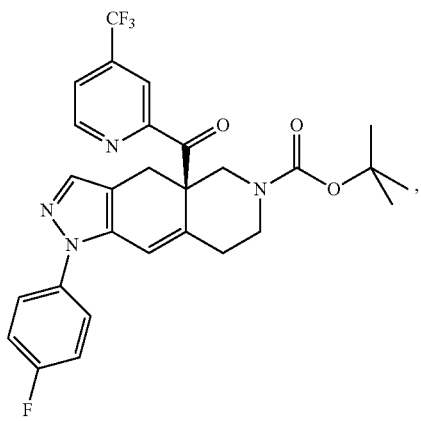

comprising the step of:

(c) forming a third reaction mixture comprising a Grignard reagent, a compound of Formula III:

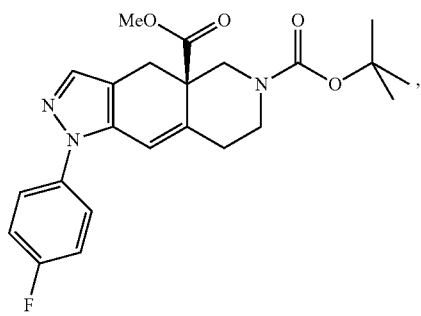

and 2-bromo-4-(trifluoromethyl)pyridine:

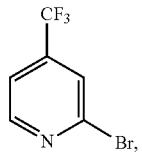

wherein the pyridine is present in a molar ratio of 1.0 to 1.5 to the compound of Formula III, and wherein the Grignard reagent is present in a molar ratio of 1.5 to 1.7 to the compound of Formula III, to prepare the compound of Formula IIa.

The Grignard reagent can be any suitable Grignard reagent. In some embodiments, the Grignard reagent comprises iPrMgCl or iPrMgBr. In some embodiments, the Grignard reagent comprises iPrMgBr.

The Grignard reagent can be present in any suitable molar ratio to the compound of Formula III. For example, the Grignard reagent can be present in a molar ratio of from 1.0 to 2.0, or from 1.1 to 1.9, from 1.2 to 1.8, from 1.3 to 1.8, from 1.4 to 1.7, from 1.5 to 1.7, or from 1.6 to 1.7 to the compound of Formula III. In some embodiments, the Grignard reagent can be present in a molar ratio of from 1.5 to 1.7 to the compound of Formula III. The Grignard reagent can be present in a molar ratio of about 1.5, or about 1.55, 1.60, 1.65, 1.70, or about 1.75 to the compound of Formula III. In some embodiments, the Grignard reagent can be present in a molar ratio of about 1.65 to the compound of Formula III.

The pyridine can be present in any suitable ratio to the compound of Formula III. For example, the pyridine can be present in a molar ratio of 1.0 to 2.0, or from 1.0 to 1.9, from 1.0 to 1.8, from 1.0 to 1.7, from 1.0 to 1.6, from 1.0 to 1.5, from 1.1 to 1.5, from 1.2 to 1.5, or from 1.3 to 1.5 to the compound of Formula III. In some embodiments, the pyridine can be present in a molar ratio of from 1.0 to 1.5 to the compound of Formula III. The pyridine can be present in a molar ratio of about 1.0, or about 1.1, 1.2, 1.3, 1.4, 1.5, 1.6, 1.7, 1.8, 1.9 or about 2.0 to the compound of Formula III. In some embodiments, the pyridine can be present in a molar ratio of about 1.4 to the compound of Formula III.

The third reaction mixture can also include a third solvent. The third solvent can be any suitable solvent including, but not limited to, tetrahydrofuran, 2-methyltetrahydrofuran, toluene xylene, or combinations thereof. In some embodiments, the third reaction mixture further comprises a third solvent. In some embodiments, the third solvent can be tetrahydrofuran, 2-methyltetrahydrofuran, toluene, xylene, or combinations thereof. In some embodiments, the third reaction mixture further comprises 2-methyltetrahydrofuran and toluene.

In some embodiments, the method of preparing the compound of Formula IIa also includes: (c1) adding an acid and water to the third reaction mixture to form a workup mixture; and (c2) distilling the workup mixture to form an intermediate mixture comprising the compound of Formula IIa, 2-methyltetrahydrofuran in an amount of less than 200 ppm, and water in an amount of less than 0.5% (w/w).

The acid of step (c1) can be any suitable acid. In some embodiments, the acid comprises formic acid, acetic acid, propanoic acid, butyric acid, hexanoic acid, octanoic acid, trifluoroacetic acid, or mixtures thereof. In some embodiments, the acid comprises acetic acid.

The intermediate mixture can include 2-methyltetrahydrofuran in any amount of less than 200 ppm. For example, the intermediate mixture can include 2-methyltetrahydrofuran in an amount of less than 200 ppm, or less than 190, 180, 170, 160, 150, 140, 130, 120, 110, 100, 90, 80, 70, 60, or less than 50 ppm. In some embodiments, the intermediate mixture can include 2-methyltetrahydrofuran in an amount of less than 100 ppm.

In some embodiments, the method of preparing the compound of Formula IIa comprises:

(c) forming the third reaction mixture comprising iPrMgBr, 2-methyltetrahydrofuran, toluene, the compound of Formula III:

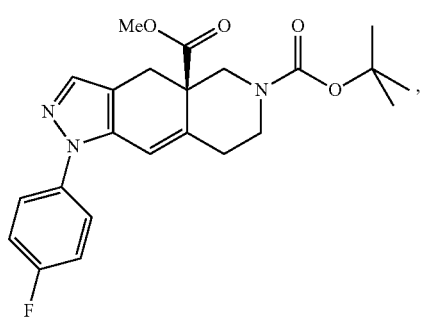

(III)

and
2-bromo-4-(trifluoromethyl)pyridine:

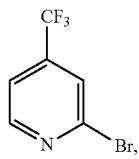

wherein the pyridine is present in the molar ratio of about 1.4 to the compound of Formula III, and wherein the Grignard reagent is present in the molar ratio of about 1.65 to the compound of Formula III, to prepare the compound of Formula IIa:

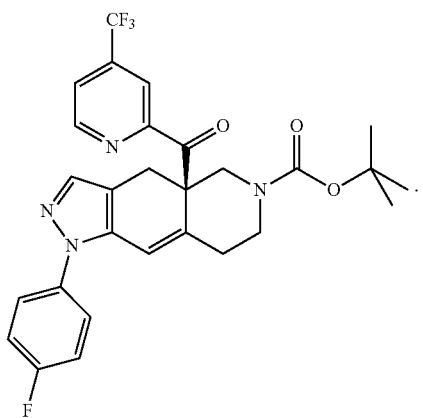

(IIa)

(c1) adding acetic acid and water to the third reaction mixture to form the workup mixture; and
(c2) distilling the workup mixture to form an intermediate mixture comprising the compound of Formula IIa, 2-methyltetrahydrofuran in an amount of less than 100 ppm, and water in an amount of less than 0.5% (w/w).

V. Method of Preparing Formula J from Formula IIb-2

In some embodiments, HX is

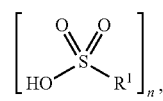

wherein $R^1$ is $C_{1-6}$ alkyl, $C_{1-10}$ haloalkyl, phenyl, or 4-methylphenyl; and subscript n is 1 to 4.

In some embodiments, the method for preparing the compound of Formula J:

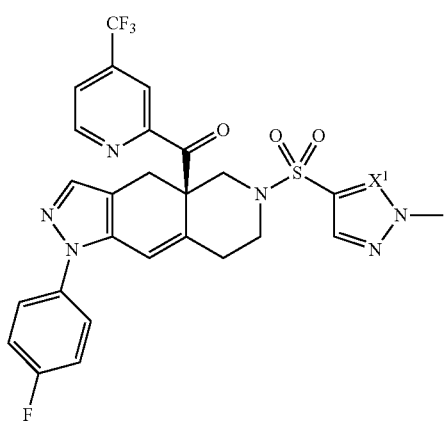

(J)

or a pharmaceutically acceptable salt thereof, comprises:

(a) forming a fourth reaction mixture comprising a compound of Formula IIb-2:

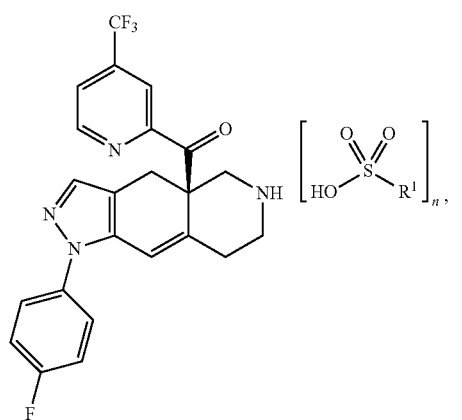

(IIb-2)

and the sulfonyl chloride:

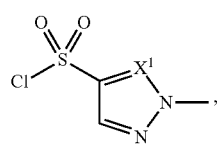

to prepare the compound of Formula J in a yield of at least 75% and a purity of at least 98%, wherein $X^1$ is —CH= or —N=;

$R^1$ is $C_{1-6}$ alkyl, $C_{1-10}$ haloalkyl, phenyl, or 4-methylphenyl; and subscript n is 1 to 4.

In some embodiments, the method for preparing the compound of Formula Ia:

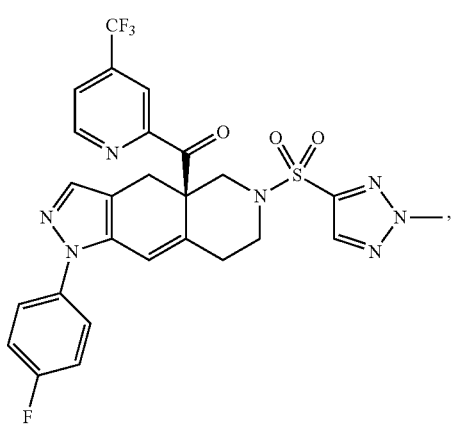

or a pharmaceutically acceptable salt thereof, comprises:

(a) forming the fourth reaction mixture comprising the compound of Formula IIb-2:

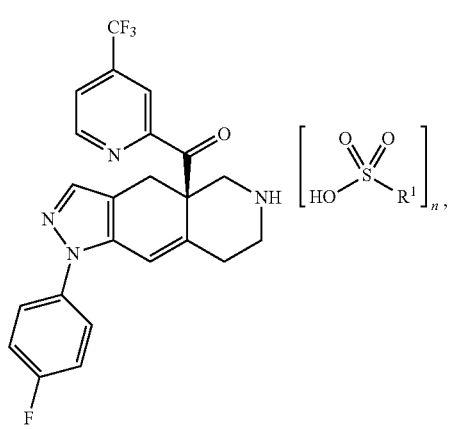

and 2-methyl-2H-1,2,3-triazole-4-sulfonyl chloride:

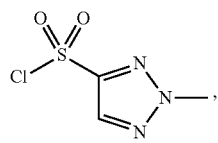

to prepare the compound of Formula Ia in a yield of at least 75% and a purity of at least 98%, wherein $R^1$ is $C_{1-6}$ alkyl, $C_{1-10}$ haloalkyl, phenyl, or 4-methylphenyl; and subscript n is 1 to 4.

In some embodiments, the compound of Formula I contains less than 1% (w/w) of the compound of Formula X-5a:

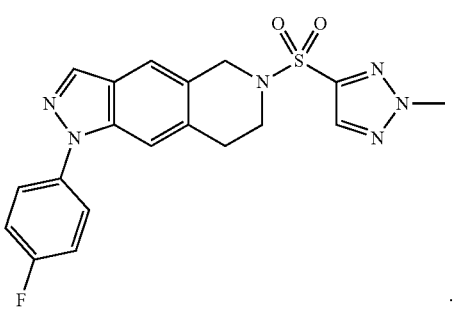

The compound of Formula I can be prepared from the compound of Formula IIb-2:

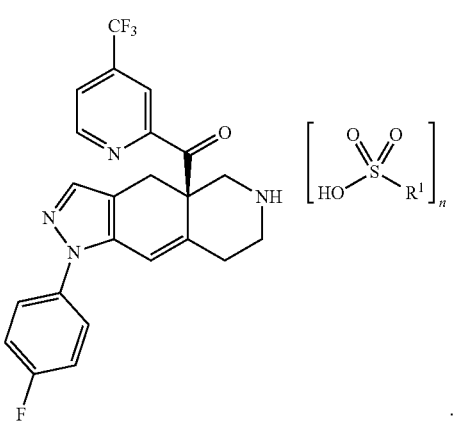

A. Preparing Formula J from Formula IIb-2

In some embodiments, the present invention provides a method of preparing a compound of Formula J:

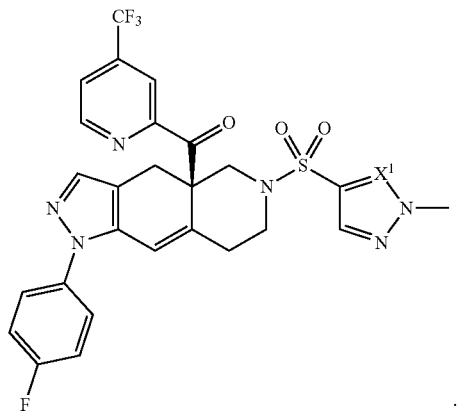
(J)

or a pharmaceutically acceptable salt thereof, comprising:
(a) forming a fourth reaction mixture comprising a compound of Formula IIb-2:

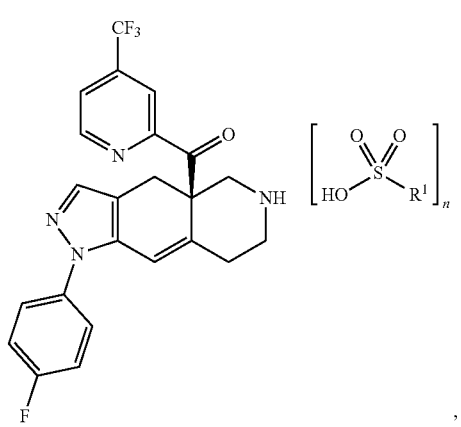
(IIb-2)

and the sulfonyl chloride:

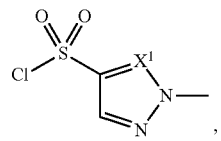

to prepare the compound of Formula J in a yield of at least 75% and a purity of at least 98%,
wherein
$X^1$ is —CH= or —N=;
$R^1$ is $C_{1-6}$ alkyl, $C_{1-10}$ haloalkyl, phenyl, or 4-methylphenyl; and
subscript n is 1 to 4.

In some embodiments, the present invention provides a method of preparing a compound of Formula I:

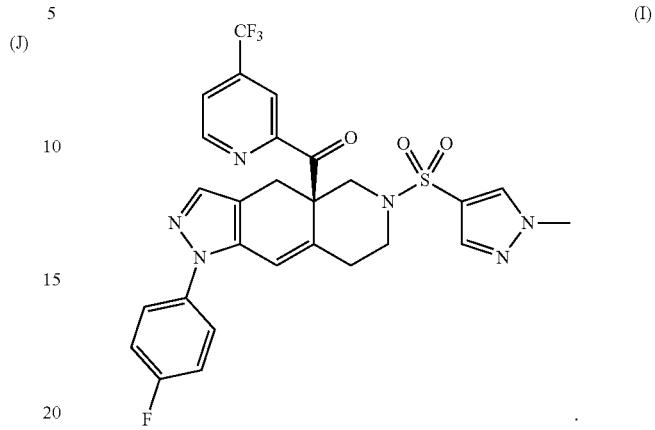
(I)

or a pharmaceutically acceptable salt thereof, comprising:
(a) forming a fourth reaction mixture comprising a compound of Formula IIb-2:

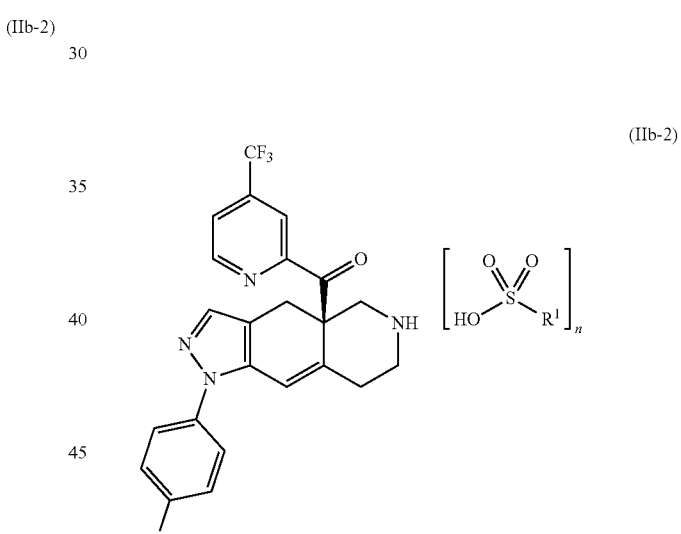
(IIb-2)

and 1-methyl-1H-pyrazole-4-sulfonyl chloride:

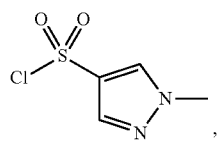

to prepare the compound of Formula I in a yield of at least 75% and a purity of at least 98%,
wherein
$R^1$ is $C_{1-6}$ alkyl, $C_{1-10}$ haloalkyl, phenyl, or 4-methylphenyl; and
subscript n is 1 to 4.

In some embodiments, the present invention provides a method of preparing a compound of Formula Ia:

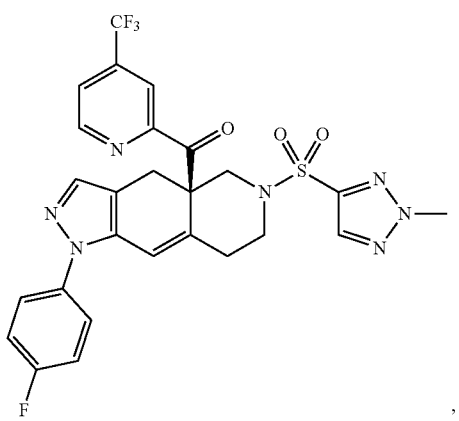

(Ia)

or a pharmaceutically acceptable salt thereof, comprising:
(a) forming a fourth reaction mixture comprising a compound of Formula IIb-2:

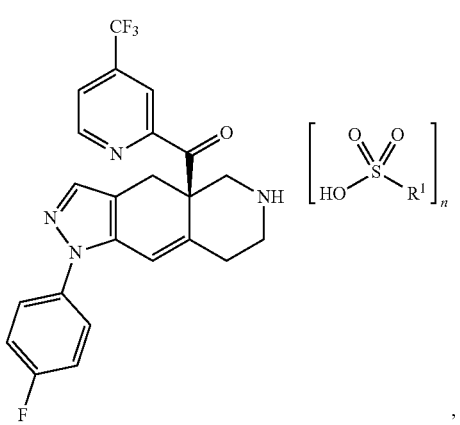

(IIb-2)

and 2-methyl-2H-1,2,3-triazole-4-sulfonyl chloride:

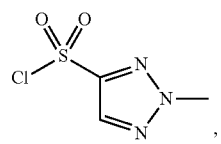

to prepare the compound of Formula Ia in a yield of at least 75% and a purity of at least 98%,
wherein
$R^1$ is $C_{1-6}$ alkyl, $C_{1-10}$ haloalkyl, phenyl, or 4-methylphenyl; and
subscript n is 1 to 4.

In some embodiments, $R^1$ is $C_{1-2}$ alkyl, $C_{1-2}$ haloalkyl, phenyl, or 4-methylphenyl. In some embodiments, $R^1$ is methyl, ethyl, —$CF_3$, phenyl, or 4-methylphenyl. In some embodiments, $R^1$ is methyl.

Subscript n can be 1, 2, 3 or 4. In some embodiments, subscript n is 1. In some embodiments, subscript n is 2. In some embodiments, subscript n is 3. In some embodiments, subscript n is 4. In some embodiments, the compound of Formula IIb-2 has the structure:

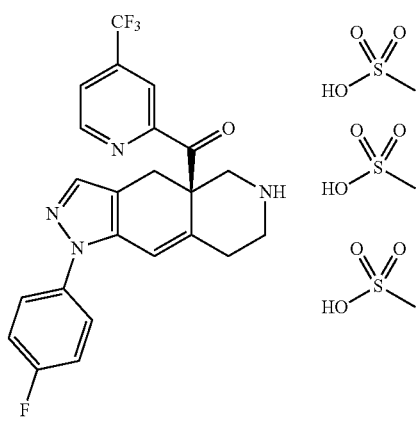

(IIb-2)

In some embodiments, the fourth reaction mixture further comprises a non-nucleophilic amine base. Any suitable non-nucleophilic amine base can be used in the fourth reaction mixture. In some embodiments, the non-nucleophilic amine base comprises trimethylamine, triethylamine, N,N-diisopropyl ethylamine (DIPEA), N,N-dimethyl isopropylamine (DIMPA), 1-ethylpiperidine, N-methylmorpholine, N-methylpyrrolidine, pyridine, N,N-dimethylaniline, N,N-diethylaniline, 2,6-lutidine, 2,4,6-collidine, 4-dimethyl aminopyridine (DMAP), quinuclidine, 4-pyrrolidinopyridine, 1,4-diazabicyclo[2.2.2]octane (DABCO), or mixtures thereof. In some embodiments, the non-nucleophilic amine base comprises triethylamine.

The fourth reaction mixture can include any suitable solvent. For example, the solvent can be an organic solvent including, but not limited to, ethyl acetate, isopropylacetate, and n-butyl acetate. In some embodiments, the fourth reaction mixture further comprises a fourth solvent. In some embodiments, the fourth solvent includes ethyl acetate, isopropyl acetate, n-butyl acetate, or mixtures thereof. In some embodiments, the fourth reaction mixture further comprises ethyl acetate.

The sulfonyl chloride used in the fourth reaction mixture can be present in any suitable molar ratio to the compound of Formula IIb-2. For example, the sulfonyl chloride can be present in a molar ratio of from 0.5 to 2.0 to the compound of Formula IIb-2, from 0.5 to 1.5, from 0.6 to 1.4, from 0.7 to 1.3, from 0.8 to 1.2, or from 0.9 to 1.1 to the compound of Formula IIb-2. In some embodiments, the sulfonyl chloride is present in a molar ratio of 0.5 to 1.5 to the compound of Formula IIb-2. The sulfonyl chloride can be present in a molar ratio of 0.5, 0.6, 0.7, 0.8, 0.9, 1.0, 1.1, 1.2, 1.3, 1.4 or 1.5 to the compound of Formula IIb-2. In some embodiments, the sulfonyl chloride can be present in a molar ratio of about 1.0 to the compound of Formula IIb-2.

The compound of Formula J, Formula I, or Formula Ia can be prepared in any suitable yield. For example, the compound of Formula J, Formula I, or Formula Ia can be prepared in a yield of at least 10, 20, 30, 40, 50, 60, 65, 70, 75, 80, 85, 90, or at least 95%. In some embodiments, the compound of Formula J, Formula I, or Formula Ia can be prepared in a yield of at least 75%.

The compound of Formula I can be prepared in any suitable yield. For example, the compound of Formula I can be prepared in a yield of at least 10, 20, 30, 40, 50, 60, 65, 70, 75, 80, 85, 90, or at least 95%. In some embodiments, the compound of Formula I can be prepared in a yield of at least 75%.

The compound of Formula J, Formula I, or Formula Ia can be prepared in any suitable purity. For example, the compound of Formula J, Formula I, or Formula Ia can be prepared in a purity of at least 90%, or 91, 92, 93, 94, 95, 96, 97, 98, or at least 99%. In some embodiments, the compound of Formula J, Formula I, or Formula Ia can be prepared in a purity of at least 96%. In some embodiments, the compound of Formula J, Formula I, or Formula Ia can be prepared in a purity of at least 97%. In some embodiments, the compound of Formula J, Formula I, or Formula Ia can be prepared in a purity of at least 98%. In some embodiments, the compound of Formula J, Formula I, or Formula Ia can be prepared in a purity of at least 99%.

The compound of Formula I can be prepared in any suitable purity. For example, the compound of Formula I can be prepared in a purity of at least 90%, or 91, 92, 93, 94, 95, 96, 97, 98, or at least 99%. In some embodiments, the compound of Formula I can be prepared in a purity of at least 96%. In some embodiments, the compound of Formula I can be prepared in a purity of at least 97%. In some embodiments, the compound of Formula I can be prepared in a purity of at least 98%. In some embodiments, the compound of Formula I can be prepared in a purity of at least 99%.

In some embodiments, the method of preparing the compound of Formula J, Formula I, or Formula Ia further comprises the steps of:

(a1) adding methanol to the fourth reaction mixture; and (a2) adding water to the fourth reaction mixture to precipitate the compound of Formula J, Formula I, or Formula Ia.

In some embodiments, the method of preparing the compound of Formula I further comprises the steps of:

(a1) adding methanol to the fourth reaction mixture; and (a2) adding water to the fourth reaction mixture to precipitate the compound of Formula I.

In some embodiments, the method of preparing the compound of Formula I from the compound of Formula IIb-2 comprises the steps of:

(a) forming the fourth reaction mixture comprising the compound of Formula IIb-2

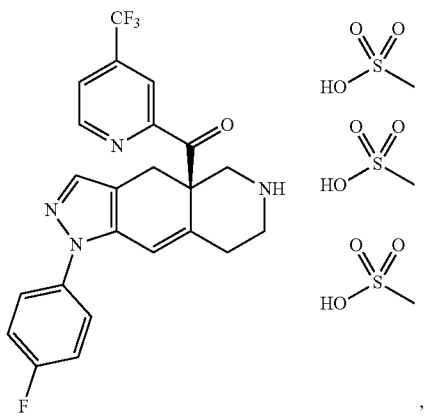

triethylamine, ethyl acetate, and 1-methyl-1H-pyrazole-4-sulfonyl chloride:

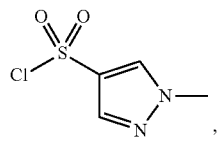

wherein the sulfonyl chloride is present in a ratio of about 1.0 to the compound of Formula IIb-2;

(a1) adding methanol to the fourth reaction mixture; and (a2) adding water to the fourth reaction mixture to precipitate the compound of Formula I in a yield of at least 75% and a purity of at least 98%.

The compound of Formula I can be prepared with any acceptable amount of Formula X-5:

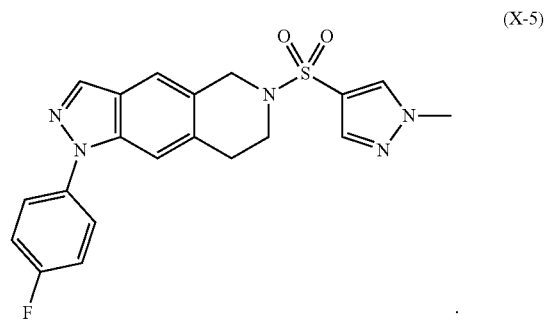 [SMILES: Cn1cc(S(=O)(=O)N2CCc3cc4c(cnn4-c4ccc(F)cc4)cc3C2)cn1]

For example, the compound Formula I can be prepared containing less than 5% (w/w), or 4, 3, 2, 1, 0.9, 0.8, 0.75, 0.7, 0.6, 0.5, 0.4, 0.3, 0.25, 0.2, or less than 0.1% (w/w) of the compound of Formula X-5. In some embodiments, the compound of Formula I can be prepared containing less than 1% (w/w) of the compound of Formula X-5:

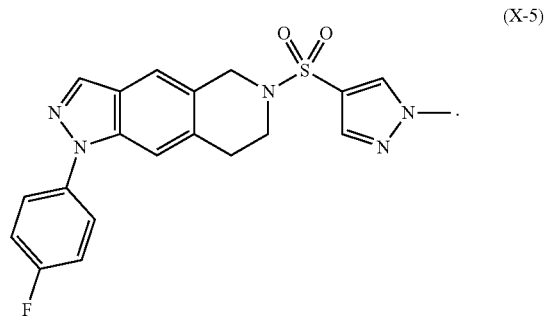 [SMILES: Cn1cc(S(=O)(=O)N2CCc3cc4c(cnn4-c4ccc(F)cc4)cc3C2)cn1]

In some embodiments, the compound of Formula I can be prepared containing less than 0.75% (w/w) of the compound of Formula X-5. In some embodiments, the compound of Formula I can be prepared containing less than 0.5% (w/w) of the compound of Formula X-5. In some embodiments, the compound of Formula I can be prepared containing less than 0.2% (w/w) of the compound of Formula X-5.

In some embodiments, the compound of Formula Ia contains less than 1% (w/w) of the compound of Formula X-5a:

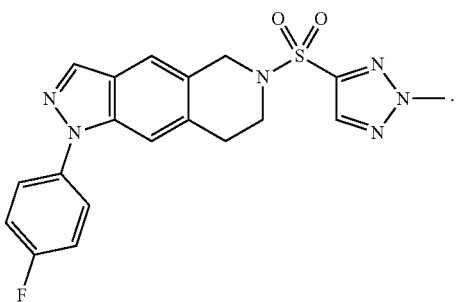

(X-5a)

B. Preparing Formula IIb-2 from Formula IIa

The compound of Formula IIb-2 can be prepared from the compound of Formula IIa. In some embodiments, the present invention provides a method of preparing a compound of Formula IIb-2:

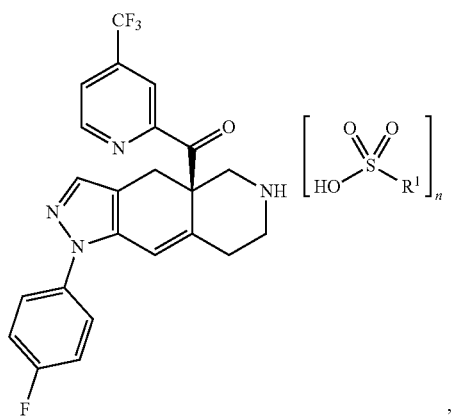

(IIb-2)

comprising:

(b) forming a fifth reaction mixture comprising a compound of Formula IIa:

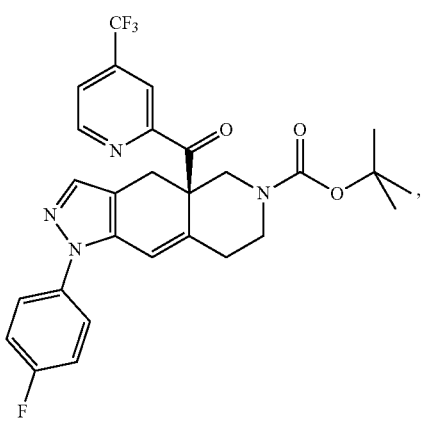

(IIa)

and a sulfonic acid of the formula:

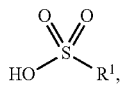

to form the compound of Formula IIb-2, wherein $R^1$ is $C_{1-6}$ alkyl, $C_{1-10}$ haloalkyl, phenyl, or 4-methylphenyl; and subscript n is 1 to 4.

Subscript n can be 1, 2, 3 or 4. In some embodiments, subscript n is 1. In some embodiments, subscript n is 2. In some embodiments, subscript n is 3. In some embodiments, subscript n is 4. In some embodiments, the compound of Formula IIb-2 has the structure:

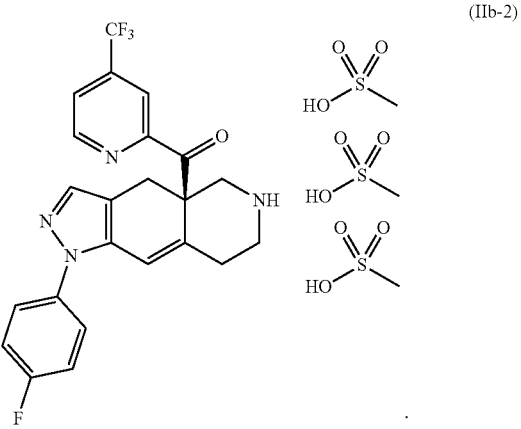

(IIb-2)

The fifth reaction mixture can include any suitable solvent. In some embodiments, the fifth reaction mixture includes a fifth solvent. The fifth solvent can include, but is not limited to, pentanes, hexanes, heptanes, benzene, toluene, diethyl ether, tetrahydrofuran, acetone, ethyl acetate, acetonitrile, methylene chloride, and chloroform. In some embodiments, the fifth solvent includes acetonitrile, tetrahydrofuran, 2-methyltetrahydrofuran, dimethylsulfoxide (DMSO), dimethylformamide (DMF), methanol, ethanol, diethyl ether, methyl-t-butyl ether (MTBE), toluene, or combinations thereof. In some embodiments, the fifth reaction mixture includes acetonitrile.

C. Preparing Formula IIa from Formula III

The compound of Formula IIa can be prepared by a variety of methods. In some embodiments, the compound of Formula IIa can be prepared by the steps of:

(c) forming a sixth reaction mixture comprising a Grignard reagent, a compound of Formula III:

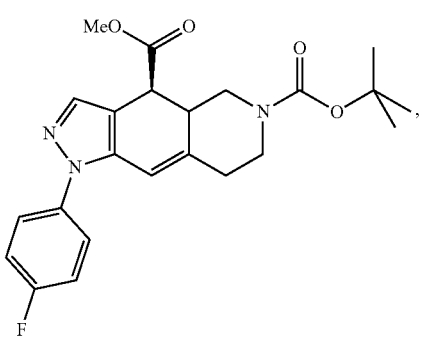

(III)

and
2-bromo-4-(trifluoromethyl)pyridine:

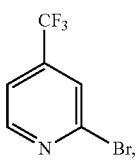

wherein the pyridine is present in a molar ratio of 2.8 to 3.2 to the compound of Formula III, and wherein the Grignard reagent is present in a molar ratio of 2.8 to 3.3 to the compound of Formula III, to prepare the compound of Formula IIa.

The Grignard reagent can be any suitable Grignard reagent. In some embodiments, the Grignard reagent comprises iPrMgCl or iPrMgBr. In some embodiments, the Grignard reagent comprises iPrMgCl.

The Grignard reagent can be present in any suitable molar ratio to the compound of Formula III. For example, the Grignard reagent can be present in a molar ratio of from 2.0 to 4.0, or 2.5 to 3.5, from 2.6 to 3.4, from 2.7 to 3.3, 2.8 to 3.3, 2.8 to 3.2, from 2.9 to 3.2, from 2.9 to 3.1 to the compound of Formula III. In some embodiments, the Grignard reagent can be present in a molar ratio of from 2.8 to 3.3 to the compound of Formula III. In some embodiments, the Grignard reagent can be present in a molar ratio of from 2.9 to 3.2 to the compound of Formula III. The Grignard reagent can be present in a molar ratio of about 2.90, or about 2.95, 3.00, 3.05, 3.10, 3.15, or about 3.20 to the compound of Formula III. In some embodiments, the Grignard reagent can be present in a molar ratio of about 3.05 to the compound of Formula III.

The pyridine can be present in any suitable ratio to the compound of Formula III. For example, the pyridine can be present in a molar ratio of 2.0 to 4.0, or 2.5 to 3.5, from 2.6 to 3.4, from 2.7 to 3.3, 2.8 to 3.2, from 2.9 to 3.1 to the compound of Formula III. In some embodiments, the pyridine can be present in a molar ratio of from 2.8 to 3.2 to the compound of Formula III. The pyridine can be present in a molar ratio of about 2.5, or about 2.6, 2.7, 2.8, 2.9, 3.0, 3.1, 3.2, 3.3, 3.4 or about 3.5 to the compound of Formula III. In some embodiments, the pyridine can be present in a molar ratio of about 3.0 to the compound of Formula III.

The sixth reaction mixture can also include a sixth solvent. The sixth solvent can be any suitable solvent including, but not limited to, tetrahydrofuran, 2-methyltetrahydrofuran, toluene, xylene, or combinations thereof. In some embodiments, the sixth reaction mixture further comprises a sixth solvent. In some embodiments, the sixth solvent can be tetrahydrofuran, 2-methyltetrahydrofuran, toluene, xylene, or combinations thereof. In some embodiments, the sixth reaction mixture further comprises 2-methyltetrahydrofuran and toluene.

In some embodiments, the method of preparing the compound of Formula IIa also includes: (c1) adding an acid and water to the sixth reaction mixture to form a workup mixture; and (c2) distilling the workup mixture to form an intermediate mixture comprising the compound of Formula IIa.

The acid of step (c1) can be any suitable acid. In some embodiments, the acid comprises formic acid, acetic acid, propanoic acid, butyric acid, hexanoic acid, octanoic acid, trifluoroacetic acid, or mixtures thereof. In some embodiments, the acid comprises acetic acid.

In some embodiments, the sixth reaction mixture further comprises the intermediate mixture comprising the compound of Formula IIa.

In some embodiments, the method of preparing the compound of Formula IIb-2 comprises the steps of:

(c) forming the sixth reaction mixture comprising tetrahydrofuran, toluene, iPrMgCl, the compound of Formula III:

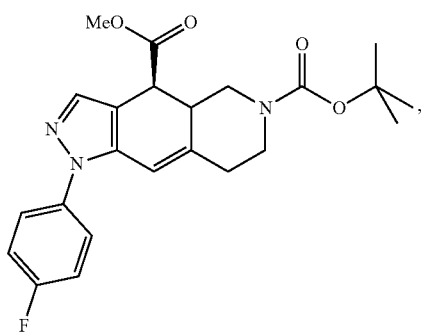

(III)

and
2-bromo-4-(trifluoromethyl)pyridine:

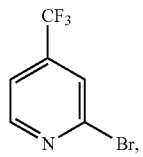

wherein the pyridine is present in the molar ratio of about 3.0 to the compound of Formula III, and wherein the Grignard reagent is present in the molar ratio of 3.05 to the compound of Formula III;

(c1) adding acetic acid and water to the sixth reaction mixture to form the workup mixture;

(c2) distilling the workup mixture to form the intermediate mixture comprising the compound of Formula IIa:

(IIa)

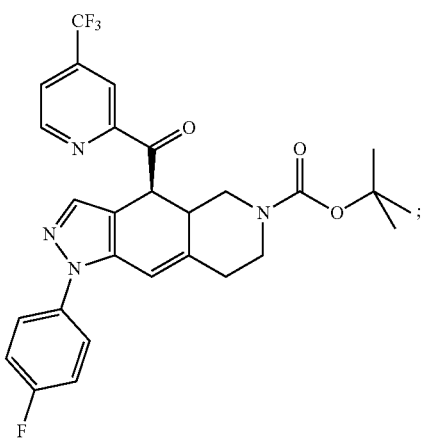

and (b) forming the fifth reaction mixture comprising the intermediate mixture, acetonitrile, and methanesulfonic acid, to form the compound of Formula IIb-2:

(IIb-2)

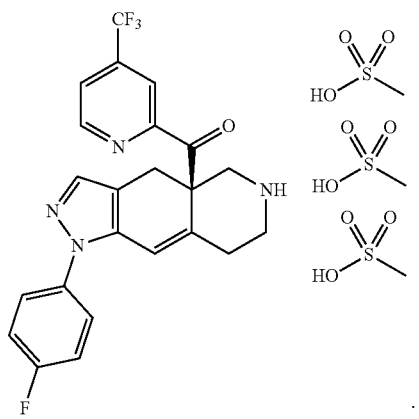

In some embodiments, the present invention provides a method of preparing a compound of Formula I:

(I)

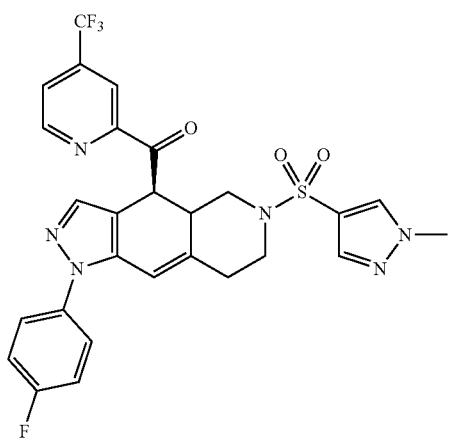

or a pharmaceutically acceptable salt thereof, comprising:

(c) forming a sixth reaction mixture comprising tetrahydrofuran, toluene, iPrMgCl, a compound of Formula III:

(III)

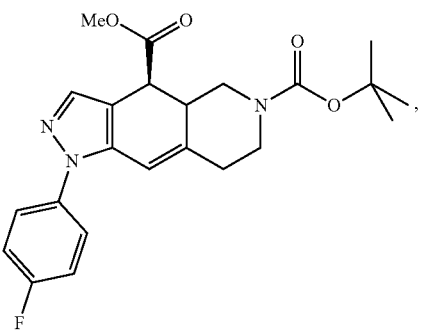

and 2-bromo-4-(trifluoromethyl)pyridine:

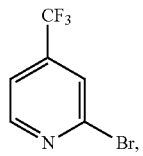

wherein the pyridine is present in a molar ratio of about 3.0 to the compound of Formula III, and wherein the Grignard reagent is present in a molar ratio of 3.05 to the compound of Formula III;

(c1) adding acetic acid and water to the sixth reaction mixture to form a workup mixture;

(c2) distilling the workup mixture to form an intermediate mixture comprising a compound of Formula IIa:

(IIa)

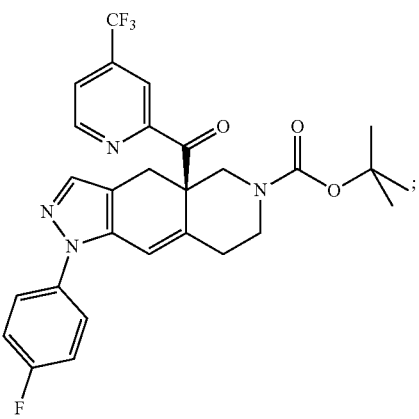

(b) forming a fifth reaction mixture comprising the intermediate mixture, acetonitrile, and methanesulfonic acid, to form a compound of Formula IIb-2:

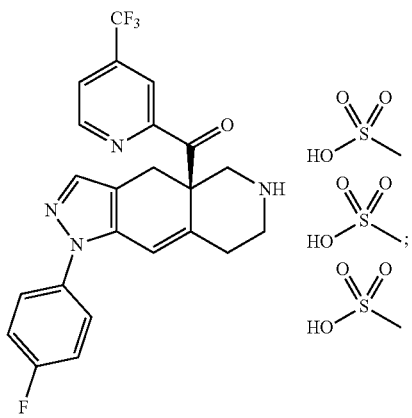

(IIb-2)

(a) forming a fourth reaction mixture comprising the compound of Formula IIb-2, triethylamine, ethyl acetate, and 1-methyl-1H-pyrazole-4-sulfonyl chloride:

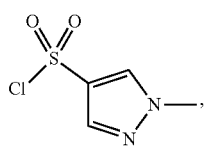

wherein the sulfonyl chloride is present in a ratio of about 1.0 to the compound of Formula IIb-2;

(a1) adding methanol to the fourth reaction mixture; and (a2) adding water to the reaction mixture to precipitate the compound of Formula I in a yield of at least 75% and a purity of at least 98%.

In some embodiments, the present invention provides a method of preparing a compound of Formula Ia:

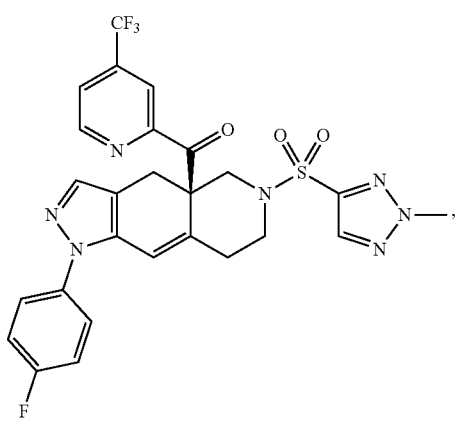

(Ia)

or a pharmaceutically acceptable salt thereof, comprising:

(c) forming a sixth reaction mixture comprising tetrahydrofuran, toluene, iPrMgCl, a compound of Formula III:

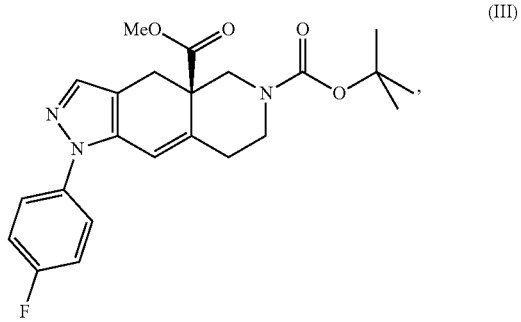 [SMILES: COC(=O)[C@]12Cc3cnn(-c4ccc(F)cc4)c3C=C1CCN(C(=O)OC(C)(C)C)C2]

(III)

and 2-bromo-4-(trifluoromethyl)pyridine:

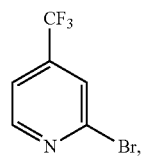

wherein the pyridine is present in a molar ratio of about 3.0 to the compound of Formula III, and wherein the Grignard reagent is present in a molar ratio of about 3.05 to the compound of Formula III;

(c1) adding acetic acid and water to the sixth reaction mixture to form a workup mixture;

(c2) distilling the workup mixture to form an intermediate mixture comprising a compound of Formula IIa:

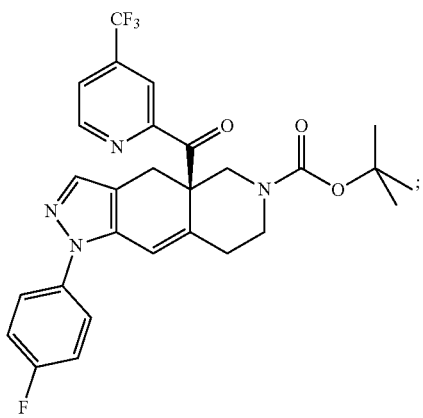

(IIa)

(b) forming a fifth reaction mixture comprising the intermediate mixture, acetonitrile, and methanesulfonic acid, to form a compound of Formula IIb-2:

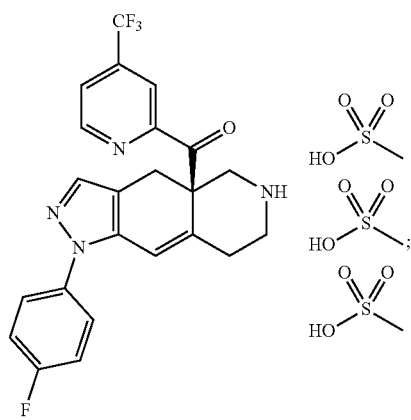

(IIb-2)

(a) forming a fourth reaction mixture comprising the compound of Formula IIb-2, triethylamine, ethyl acetate, and 2-methyl-2H-1,2,3-triazole-4-sulfonyl chloride:

wherein the sulfonyl chloride is present in a ratio of about 1.0 to the compound of Formula IIb-2;
(a1) adding methanol to the fourth reaction mixture; and
(a2) adding water to the reaction mixture to precipitate the compound of Formula Ia in a yield of at least 75% and a purity of at least 98%.

VI. Low Impurity Compositions

The present invention provides compositions of Formula I having a low impurity content. In some embodiments, the present invention provides a composition comprising:

a compound of Formula I in an amount of at least 99% (w/w):

(I)

and
one or more impurity in an amount of from 0.01 to 1% (w/w).

The composition of Formula I can include one or more impurities present in a total amount of 0.01 to 1% (w/w). In some embodiments, the impurity includes at least one of:

a compound of Formula X-4 in an amount of less than 0.5% (w/w):

(X-4)

a compound of Formula X-5 in an amount of less than 0.2% (w/w):

(X-5)

and
a compound of Formula X-6 in an amount of less than 0.1% (w/w):

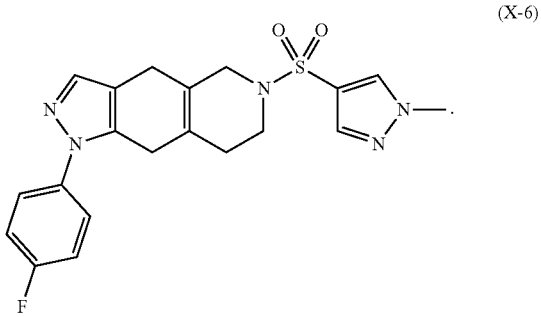 [SMILES: Cn1cc(S(=O)(=O)N2CCC3=C(Cc4cnn(-c5ccc(F)cc5)c4C3)C2)cn1]

(X-6)

The impurity present in the composition of the compound Formula I can include the compound of Formula X-4 in an amount of less than 1% (w/w). For example, the composition of the compound Formula I can include less than 1.0 (w/w), or less than 0.9, 0.8, 0.75, 0.7, 0.6, 0.5, 0.4, 0.3, 0.25, 0.2, or less than 0.1% (w/w) of the compound of Formula X-4. In some embodiments, the composition comprising the compound of Formula I can contain less than 0.5% (w/w) of the compound of Formula X-4. In some embodiments, the composition comprising the compound of Formula I can contain less than 0.3% (w/w) of the compound of Formula X-4. In some embodiments, the composition comprising the compound of Formula I can contain less than 0.1% (w/w) of the compound of Formula X-4.

The impurity present in the composition of the compound of Formula I can include the compound of Formula X-5 in an amount of less than 1% (w/w). For example, the composition comprising the compound of Formula I can contain less than 1.0 (w/w), or less than 0.9, 0.8, 0.75, 0.7, 0.6, 0.5, 0.4, 0.3, 0.25, 0.2, or less than 0.1% (w/w) of the compound of Formula X-5. In some embodiments, the composition comprising the compound of Formula I can contain less than 1% (w/w) of the compound of Formula X-5. In some embodiments, the composition comprising the compound of Formula I can contain less than 0.75% (w/w) of the compound of Formula X-5. In some embodiments, the composition comprising the compound of Formula I can contain less than 0.5% (w/w) of the compound of Formula X-5. In some embodiments, the composition comprising the compound of Formula I can contain less than 0.2% (w/w) of the compound of Formula X-5.

The impurity present in the composition comprising the compound of Formula I can contain less than 1.0 (w/w), or less than 0.9, 0.8, 0.75, 0.7, 0.6, 0.5, 0.4, 0.3, 0.25, 0.2, or less than 0.1% (w/w) of the compound of Formula X-6. In some embodiments, the composition comprising the compound of Formula I can contain less than 0.25% (w/w) of the compound of Formula X-6. In some embodiments, the composition comprising the compound of Formula I can contain less than 0.2% (w/w) of the compound of Formula X-6. In some embodiments, the composition comprising the compound of Formula I can contain less than 0.1% (w/w) of the compound of Formula X-6.

In some embodiments, the impurity comprises: the compound of Formula X-4 in an amount of less than 0.1% (w/w); the compound of Formula X-5 in an amount of less than 0.15% (w/w); and the compound of Formula X-6 in an amount of less than 0.1% (w/w).

The impurity present in the composition comprising the compound of Formula I can contain methyl-1-methyl-1H-pyrazole-4-sulfonate:

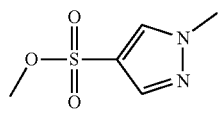

in an amount of less than 10 ppm. For example, the composition comprising the compound of Formula I can contain the impurity of methyl-1-methyl-1H-pyrazole-4-sulfonate in an amount of less than 10 ppm, or less than 9, 8, 7, 6, 5, or less than 4 ppm. In some embodiments, the composition comprising the compound of Formula I can contain the impurity of methyl-1-methyl-1H-pyrazole-4-sulfonate in an amount of less than 8 ppm. In some embodiments, the composition comprising the compound of Formula I can contain the impurity of methyl-1-methyl-1H-pyrazole-4-sulfonate in an amount of less than 6 ppm. In some embodiments, the composition comprising the compound of Formula I can contain the impurity of methyl-1-methyl-1H-pyrazole-4-sulfonate in an amount of less than 4 ppm.

The impurity present in the composition comprising the compound of Formula I can contain 1-methyl-1H-pyrazole-4-sulfonyl chloride:

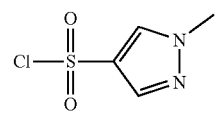

in an amount of less than 10 ppm. For example, the composition comprising compound of Formula I can contain 1-methyl-1H-pyrazole-4-sulfonyl chloride in an amount of less than 10 ppm, or less than 9, 8, 7, 6, 5, or less than 4 ppm. In some embodiments, the composition comprising compound of Formula I can contain 1-methyl-1H-pyrazole-4-sulfonyl chloride in an amount of less than 8 ppm. In some embodiments, the composition comprising compound of Formula I can contain 1-methyl-1H-pyrazole-4-sulfonyl chloride in an amount of less than 6 ppm. In some embodiments, the composition comprising compound of Formula I can contain 1-methyl-1H-pyrazole-4-sulfonyl chloride in an amount of less than 4 ppm.

In some embodiments, the impurity further comprises: 1-methyl-1H-pyrazole-4-sulfonyl chloride in an amount of less than 4 ppm; and methyl 1-methyl-1H-pyrazole-4-sulfonate in an amount of less than 4 ppm. In some embodiments, the impurity further comprises: 1-methyl-1H-pyrazole-4-sulfonyl chloride in an amount of less than 4 ppm; methyl 1-methyl-1H-pyrazole-4-sulfonate in an amount of less than 4 ppm, ethyl 1-methyl-1H-pyrazole-4-sulfonate in an amount of less than 4 ppm, and isopropyl 1-methyl-1H-pyrazole-4-sulfonate in an amount of less than 4 ppm.

The composition comprising the compound of Formula I can also contain one or more of the following impurities:

a compound having the Formula X-D in an amount of less than 0.40% (w/w):

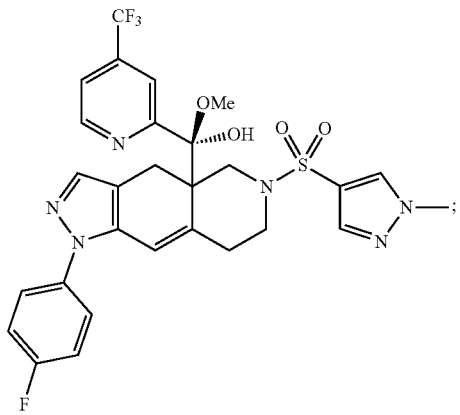

(X-D)

a compound having the Formula X-E in an amount of less than 0.40% (w/w):

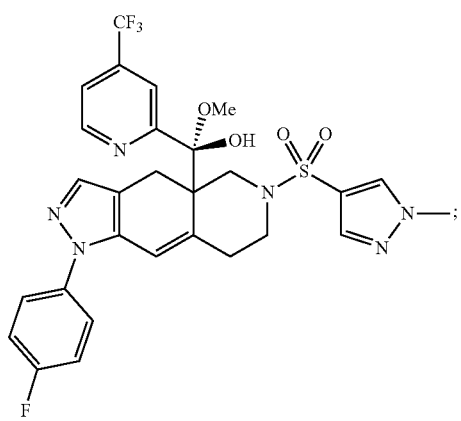

(X-E)

and
a compound having the Formula X-F in an amount of less than 0.30% (w/w):

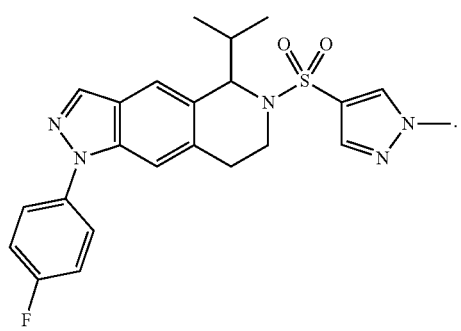

(X-F)

In some embodiments, the composition comprising the compound of Formula I can also contain one or more of the following impurities:

a compound having the Formula X-D in an amount of less than 0.40% (w/w):

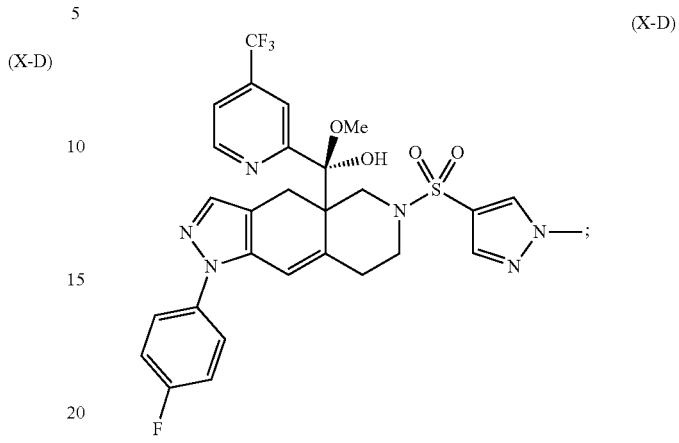

(X-D)

and
a compound having the Formula X-E in an amount of less than 0.40% (w/w):

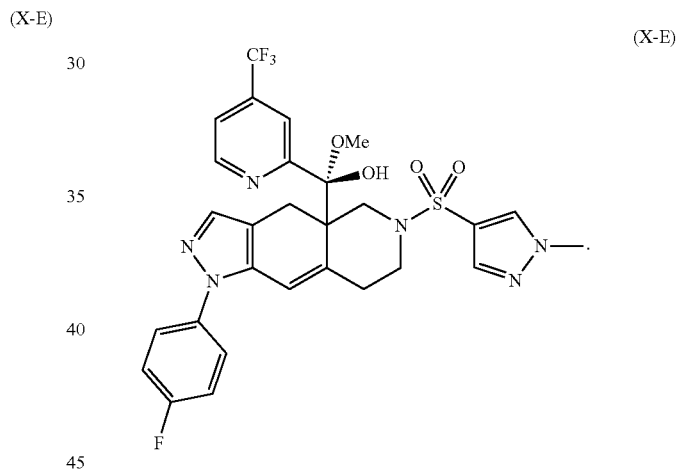

(X-E)

In some embodiments, the composition comprising the compound of Formula I can also contain a compound having the Formula X-F in an amount of less than 0.30% (w/w):

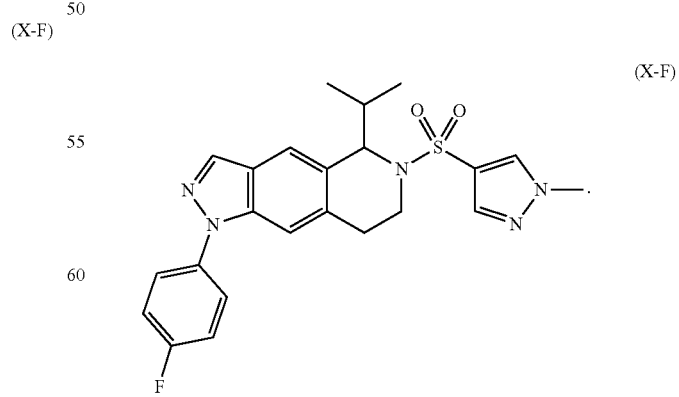

(X-F)

In some embodiments, the present invention provides a composition of:

a compound of Formula Ia in an amount of at least 99% (w/w):

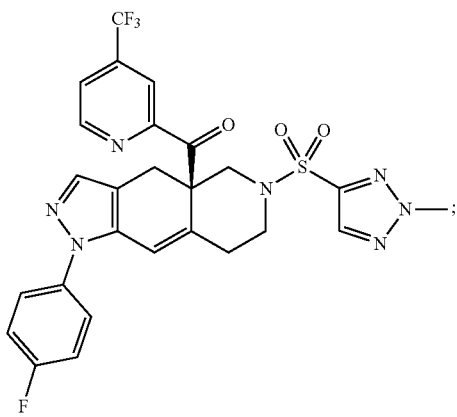

(Ia)

and one or more impurity in an amount of from 0.01 to 1% (w/w).

In some embodiments, the impurity includes at least one of:

a compound of Formula X-4a in an amount of less than 0.5% (w/w):

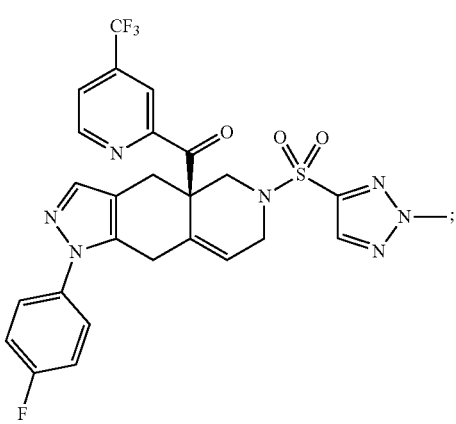

(X-4a)

a compound of Formula X-5a in an amount of less than 0.2% (w/w):

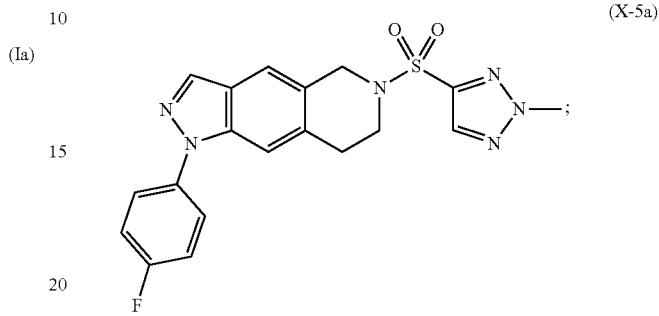

(X-5a)

and a compound of Formula X-6a in an amount of less than 0.1% (w/w):

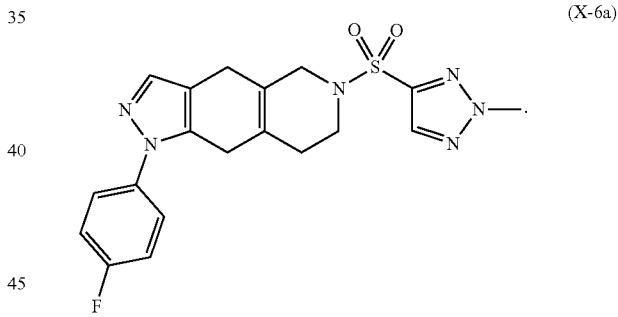

(X-6a)

In some embodiments, the impurity comprises: the compound of Formula X-4a in an amount of less than 0.1% (w/w); the compound of Formula X-5a in an amount of less than 0.15% (w/w); and the compound of Formula X-6a in an amount of less than 0.1% (w/w).

In some embodiments, the impurity further comprises one or more of: 2-methyl-2H-1,2,3-triazole-4-sulfonyl chloride in an amount of less than 4 ppm; methyl 2-methyl-2H-1,2,3-triazole-4-sulfonate in an amount of less than 4 ppm; ethyl 2-methyl-2H-1,2,3-triazole-4-sulfonate in an amount of less than 4 ppm; and isopropyl 2-methyl-2H-1,2,3-triazole-4-sulfonate in an amount of less than 4 ppm. In some embodiments, the impurity further comprises: 2-methyl-2H-1,2,3-triazole-4-sulfonyl chloride in an amount of less than 4 ppm; methyl 2-methyl-2H-1,2,3-triazole-4-sulfonate in an amount of less than 4 ppm; ethyl 2-methyl-2H-1,2,3-triazole-4-sulfonate in an amount of less than 4 ppm; and isopropyl 2-methyl-2H-1,2,3-triazole-4-sulfonate in an amount of less than 4 ppm.

In some embodiments, the impurity further comprises:
a compound of Formula X-Da in an amount of less than 0.40% (w/w)

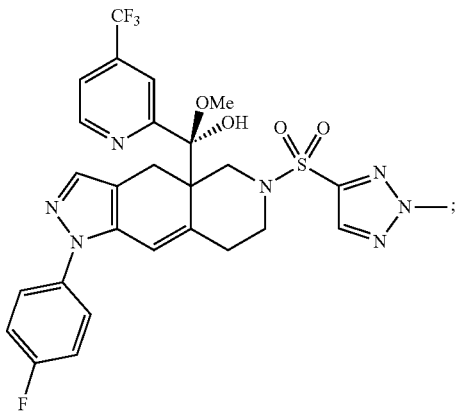

(X-Da)

and a compound of Formula X-Ea in an amount of less than 0.40% (w/w)

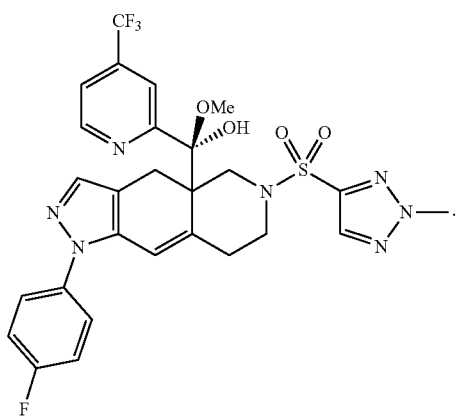

(X-Ea)

VII. Crystalline Form of Formula IIb

The present invention also provides crystalline forms of the compound of Formula IIb.

A. (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone Tris-methanesulfonic Acid In some embodiments, the present invention provides a crystalline form of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid:

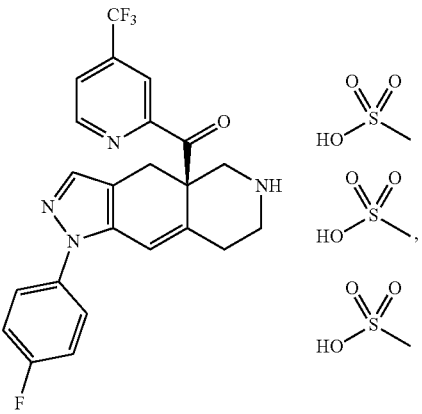

characterized by an X-ray powder diffraction (XRPD pattern having peaks at about 18.2°, 18.3°, and 19.7° 2-θ±0.2° 2-θ.

Figure 2:
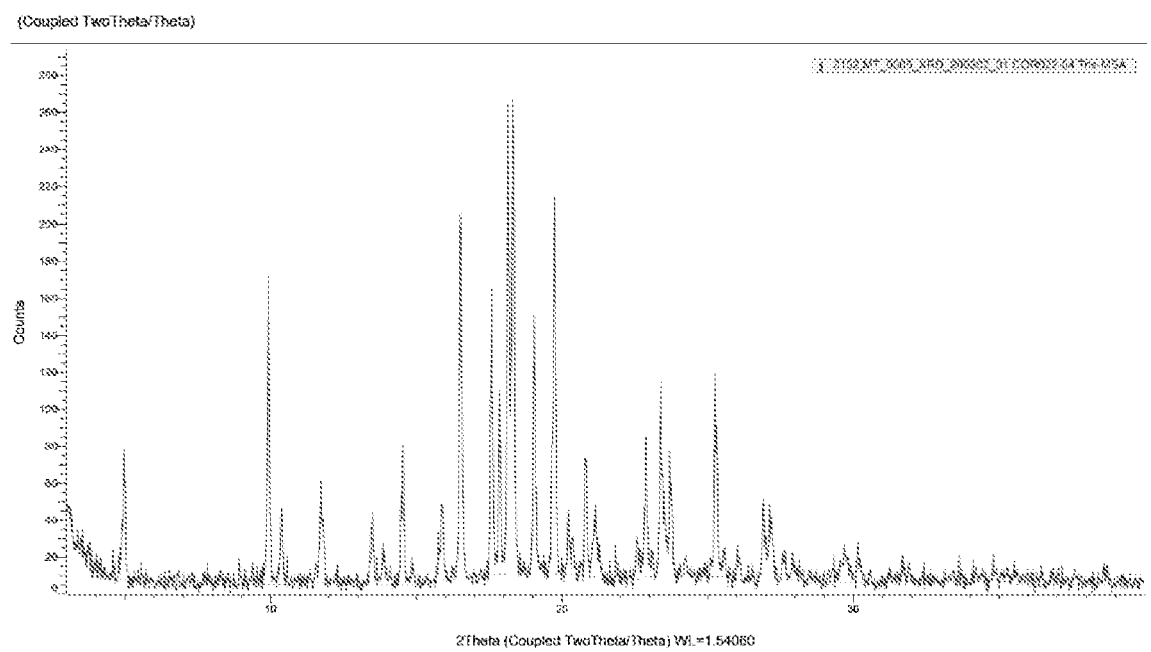
FIG. 2 shows the X-ray powder diffraction (XRPD) pattern of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid.

In some embodiments, the XRPD further comprises peaks at about 9.9°, 16.5°, and 17.6° 2-θ+0.2° 2-θ. In some embodiments, the XRPD further comprises peaks at about 5.0°, 14.5°, 17.9°, 19.0°, 20.8°, 22.9°, 23.4°, and 25.3° 2-θ±0.2° 2-θ. In some embodiments, the XRPD comprises peaks at about 5.0°, 9.9°, 14.5°, 16.5°, 17.6°, 17.9°, 18.2°, 18.3°, 19.0°, 19.7°, 20.8°, 22.9°, 23.4°, and 25.3° 2-θ±0.2° 2-θ. In some embodiments, crystalline form is characterized by the XRPD pattern substantially as set forth in FIG. 2.

Figure 3:
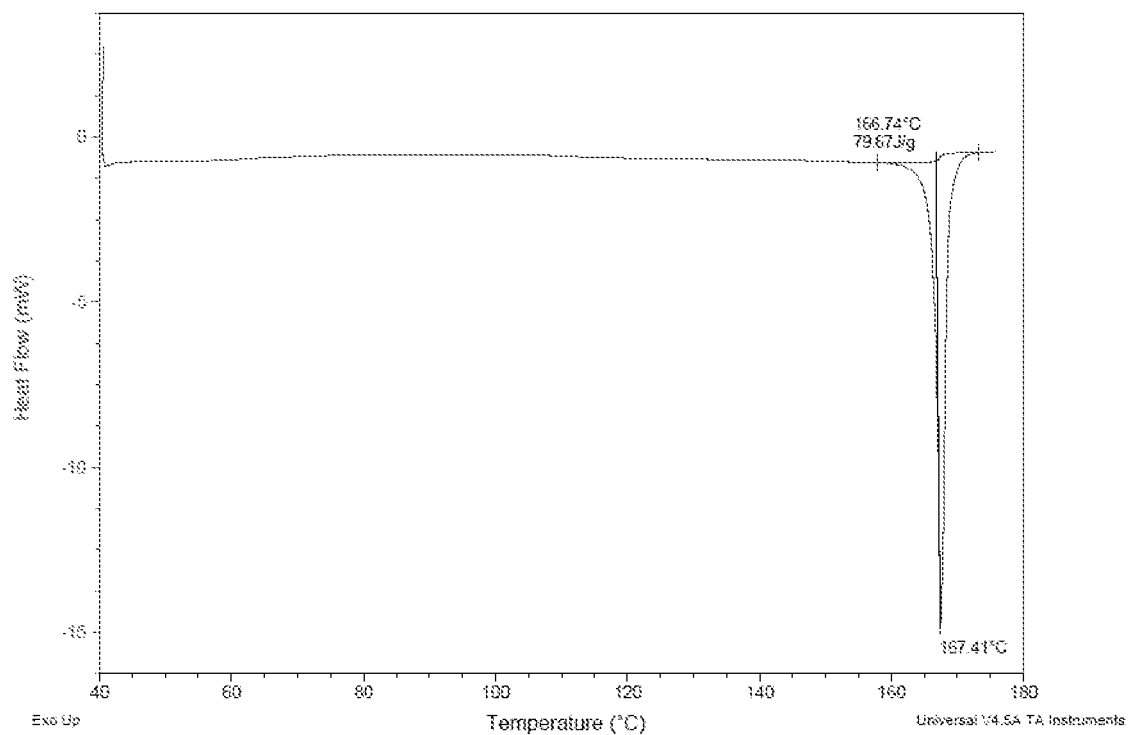
FIG. 3 shows the differential scanning calorimetry (DSC) thermogram of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid.
Figure 4:
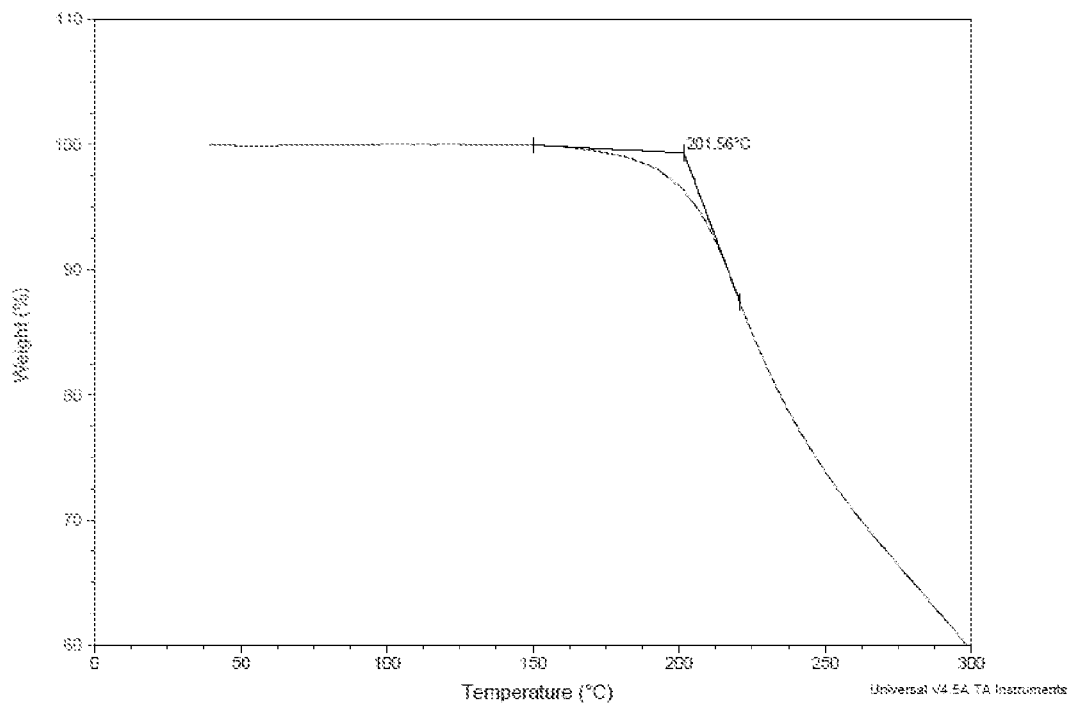
FIG. 4 shows the thermal gravimetric analysis of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid.

In some embodiments, the crystalline form is characterized by a differential scanning calorimetry (DSC) thermogram having an endotherm with an onset of about 167°. In some embodiments, the crystalline form is characterized by a DSC thermogram substantially as shown in FIG. 3.

B. (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone oxalic Acid In some embodiments, the present invention provides a crystalline form of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone oxalic acid:

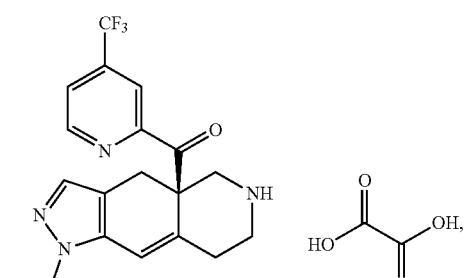

characterized by an X-ray powder diffraction (XRPD pattern having peaks at about 6.1, 8.4, 10.6 and 15.6° 2-θ±0.2° 2-θ.

Figure 5:
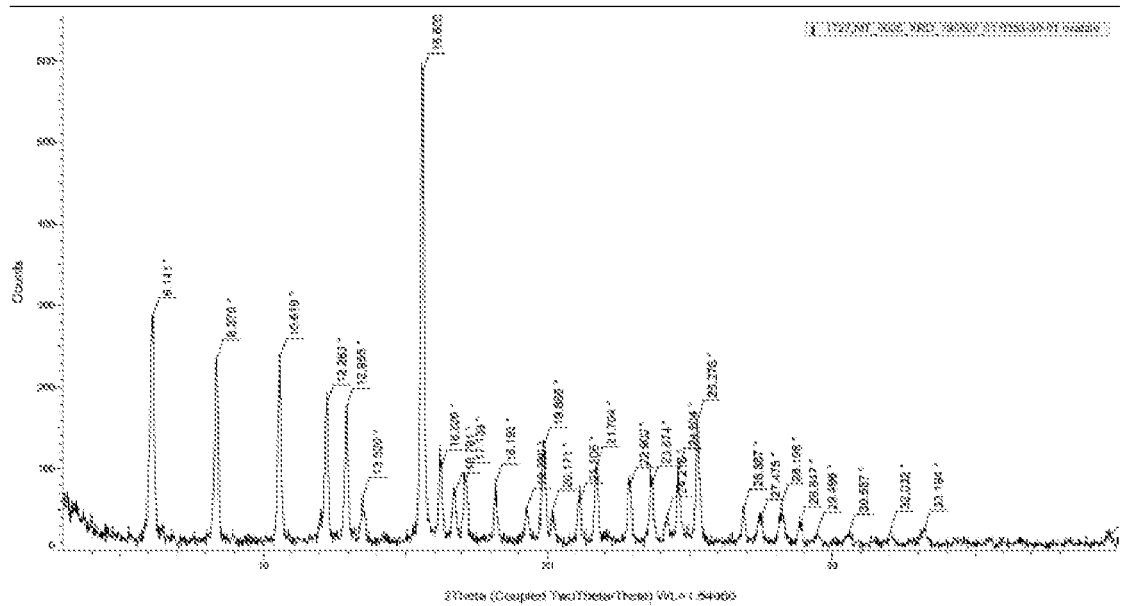
FIG. 5 shows the X-ray powder diffraction (XRPD) pattern of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-oxalic acid.

In some embodiments, the XRPD further comprises peaks at about 12.3, 13.0, and 25.3° 2-θ±0.2° 2-θ. In some embodiments, the XRPD further comprises peaks at about 16.2, 17.1, 18.2, 19.9, 21.7, 22.9, 23.7, and 24.6° 2-θ±0.2° 2-θ. In some embodiments, the XRPD comprises peaks at about 6.1, 8.4, 10.6, 12.3, 13.0, 15.6, 16.2, 17.1, 18.2, 19.9, 21.7, 22.9, 23.7, 24.6 and 25.3° 2-θ±0.2° 2-θ. In some embodiments, the crystalline form is characterized by an X-ray powder diffraction (XRPD pattern substantially as set forth in FIG. 5.

Figure 6:
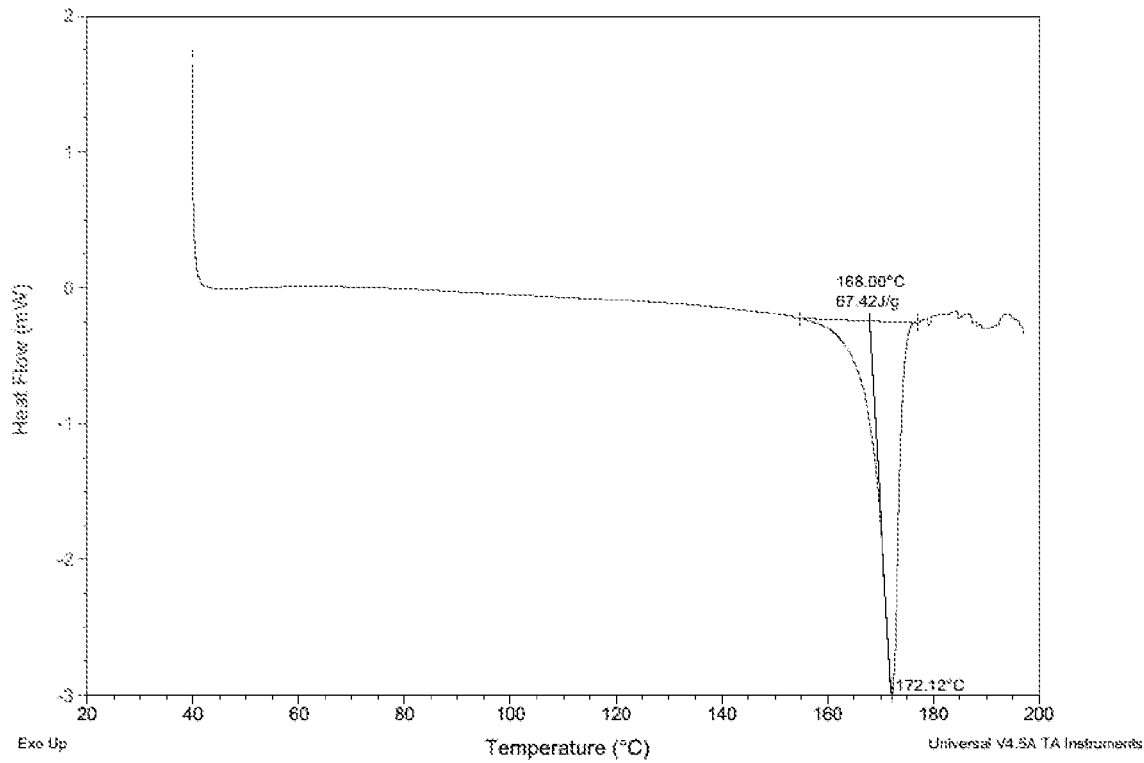
FIG. 6 shows the differential scanning calorimetry (DSC) thermogram of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-oxalic acid.
Figure 7:
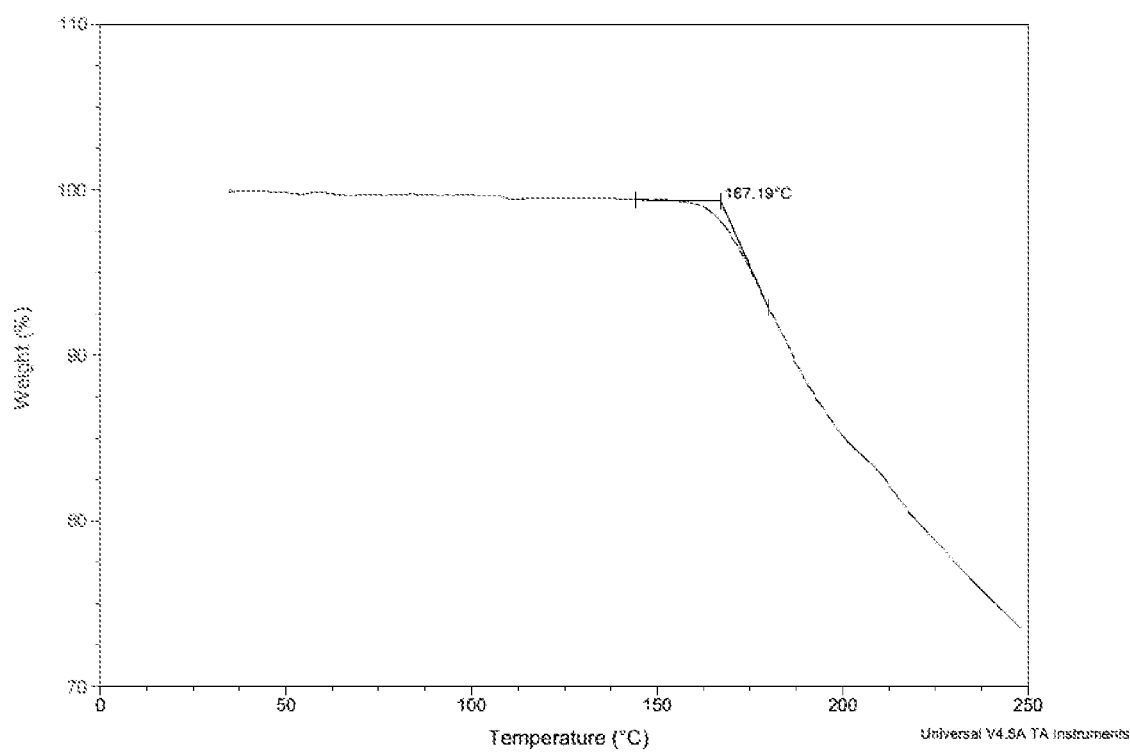
FIG. 7 shows the thermal gravimetric analysis of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-oxalic acid.

In some embodiments, the crystalline form is characterized by a differential scanning calorimetry (DSC) thermogram having an endotherm with an onset of about 168°. In some embodiments, the crystalline form is characterized by a DSC thermogram substantially as shown in FIG. 6.

C. (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone hydrochloric Acid In some embodiments, the present invention provides a crystalline form of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-hydrochloric acid:

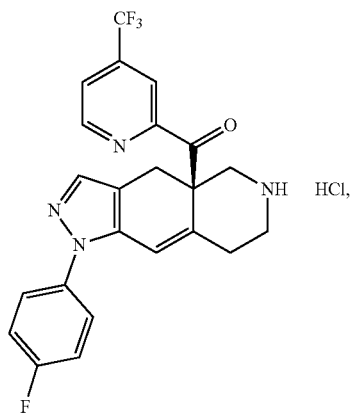

characterized by an X-ray powder diffraction (XRPD pattern having peaks at about 15.3, 22.0, 23.1, and 24.5° 2-θ+0.2° 2-θ.

Figure 8:
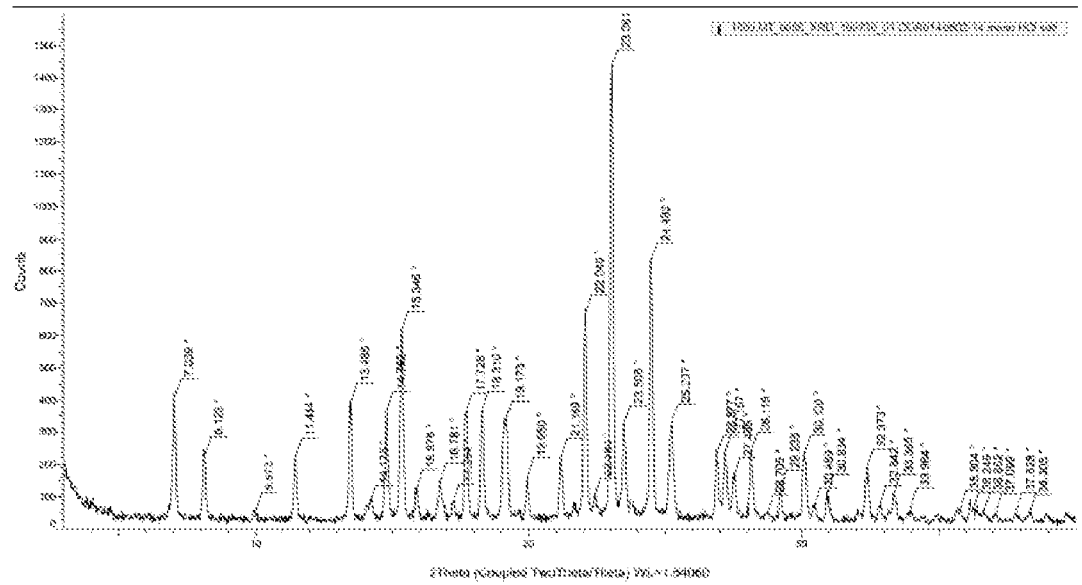
FIG. 8 shows the X-ray powder diffraction (XRPD) pattern of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-hydrochloric acid.

In some embodiments, the XRPD further comprises peaks at about 7.0, 13.5, 14.8, 17.7, 18.3, 19.2, 23.5, and 25.2° 2-θ±0.2° 2-θ. In some embodiments, the XRPD further comprises peaks at about 8.1, 11.5, 21.2, 26.9, 27.2, 28.1, 30.1, and 32.4° 2-θ±0.2° 2-θ. In some embodiments, the XRPD comprises peaks at about 7.0, 8.1, 11.5, 13.5, 14.8, 15.3, 17.7, 18.3, 19.2, 21.2, 22.0, 23.1, 23.5, 24.5, 25.2, 26.9, 27.2, 28.1, 30.1, and 32.4° 2-θ±0.2° 2-θ. In some embodiments, the crystalline form is characterized by an X-ray powder diffraction (XRPD pattern substantially as set forth in FIG. 8.

Figure 9:
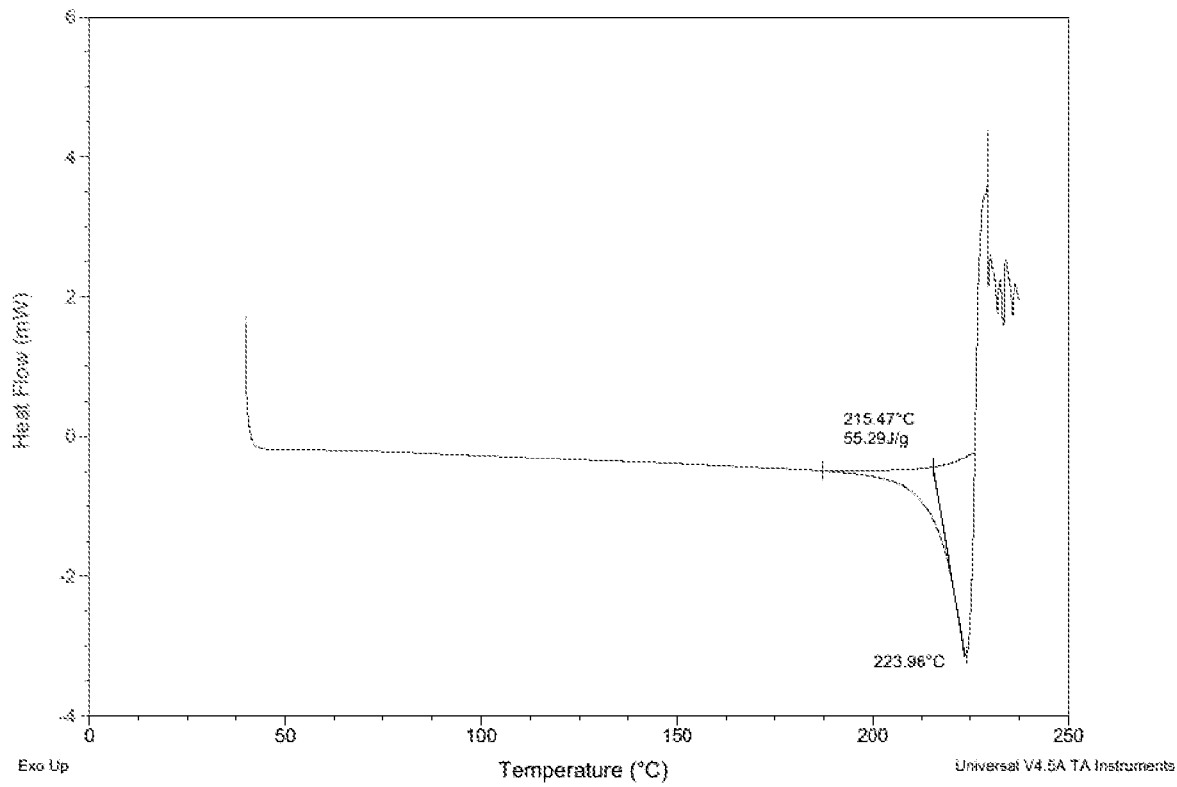
FIG. 9 shows the differential scanning calorimetry (DSC) thermogram of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-hydrochloric acid.
Figure 10:
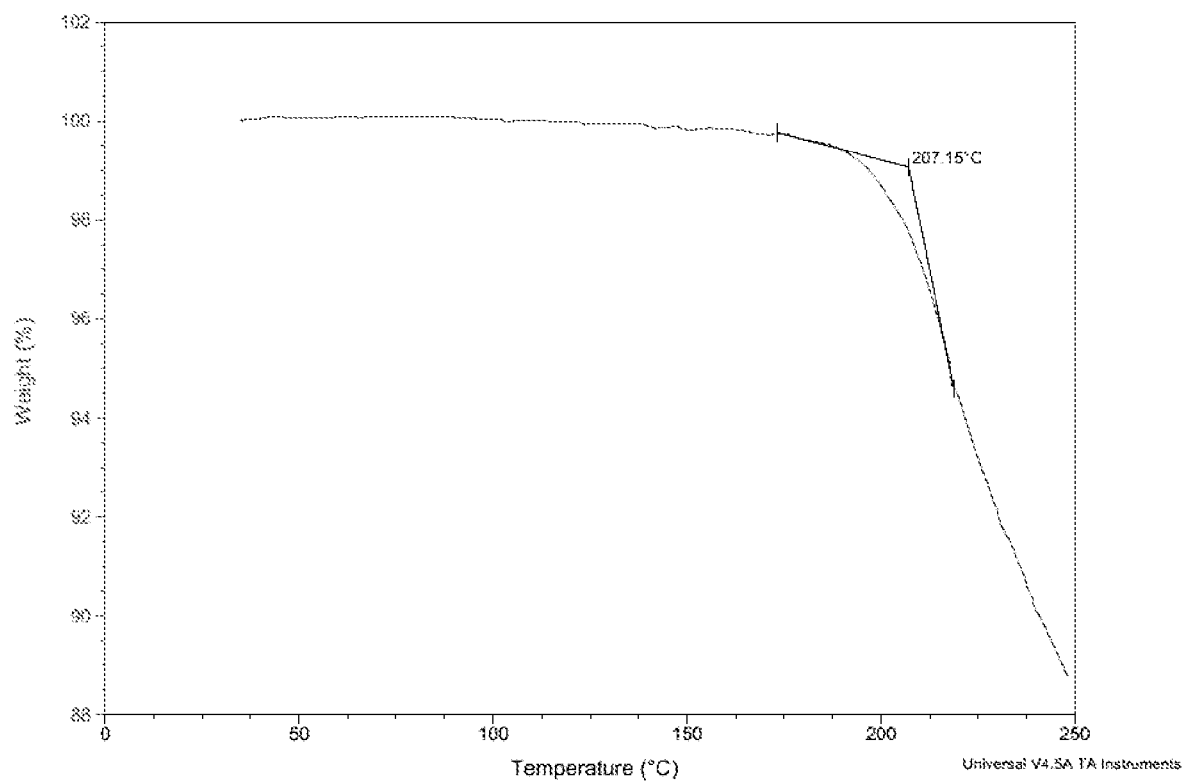
FIG. 10 shows the thermal gravimetric analysis of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-hydrochloric acid.

In some embodiments, the crystalline form is characterized by a differential scanning calorimetry (DSC) thermogram having an endotherm with an onset of about 215°. In some embodiments, the crystalline form is characterized by a DSC thermogram substantially as shown in FIG. 9.

VIII. Compositions

In some embodiments, the present invention provides a pharmaceutical composition comprising a low impurity composition of the present invention and a pharmaceutically acceptable excipient.

The low impurity compositions of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The low impurity compositions of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the low impurity compositions of the present invention can be administered transdermally. The compounds of formula I of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including one or more pharmaceutically acceptable carriers and/or excipients and a compound of formula I.

For preparing pharmaceutical compositions from the low impurity compositions of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, surfactants, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties and additional excipients as required in suitable proportions and compacted in the shape and size desired.

The powders, capsules and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other excepients, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers including, but not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of formula I mixed with a filler or binders such as lactose or starches, lubricants such as talc or magnesium stearate, and, optionally, stabilizers. In soft capsules, the compounds of formula I may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of formula I in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of formula I of the invention can be delivered by transdermally, by a topical route, formulated as applicator sticks, solutions, suspensions, emulsions, gels, creams, ointments, pastes, jellies, paints, powders, and aerosols.

The compounds of formula I and compositions of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the formulations of the compounds of formula I of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. For example, the dose can be 50 mg, or 100, 150, 200, 250, 300, 350, 400, 450, or 500 mg. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR and/or MR modulator and disease or condition treated.

Single or multiple administrations of the compound of formula I formulations can be administered depending on the dosage and frequency as required and tolerated by the patient. The formulations should provide a sufficient quantity of active agent to effectively treat the disease state. Thus, in one embodiment, the pharmaceutical formulations for oral administration of the compound of formula I is in a daily amount of between about 0.5 to about 30 mg per kilogram of body weight per day. In an alternative embodiment, dosages are from about 1 mg to about 20 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing formulations including the compound of formula I for parenteral administration are known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a pharmaceutical composition including a compound of formula I of the invention has been formulated in one or more acceptable carriers, it can be placed in an appropriate container and labeled for treatment of an indicated condition. For administration of the compounds of formula I, such labeling would include, e.g., instructions concerning the amount, frequency and method of administration.

In some embodiments, the compositions of the present invention are useful for parenteral administration, such as intravenous (IV) administration or administration into a body cavity or lumen of an organ. The formulations for administration will commonly comprise a solution of the compositions of the present invention dissolved in one or more pharmaceutically acceptable carriers. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, tonicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

IX. Methods & Use

In some embodiments, the present invention provides a method of treating a disorder or condition through modulating a glucocorticoid receptor, the method comprising administering to a subject in need of such treatment, a therapeutically effective amount of any one of the low impurity compositions of the present invention, or a pharmaceutical composition of the present invention, thereby treating the disorder or condition.

In some embodiments, the present invention provides a method of treating a disorder or condition through antagonizing a glucocorticoid receptor, the method comprising administering to a subject in need of such treatment, an effective amount of any one of the low impurity compositions of the present invention, or a pharmaceutical composition of the present invention.

In some embodiments, the disorder or condition is selected from the group consisting of amyotrophic lateral sclerosis (ALS), obesity, diabetes, cardiovascular disease, hypertension, Syndrome X, depression, anxiety, glaucoma, neurodegeneration, Alzheimer's disease, Parkinson's disease, Cushing's Syndrome, Cushing Disease, cancer, liver disease, osteoporosis, muscle frailty, a disorder caused by adrenal disease-related cortisol excess, addiction, psychosis, anorexia, cachexia, post-traumatic stress syndrome, post-surgical bone fracture, a GR-related metabolic disorders, major psychotic depression, mild cognitive impairment, dementia, hyperglycemia, a stress disorder, antipsychotic induced weight gain, delirium, cognitive impairment in depressed patients, postpartum psychosis, postpartum depression, and a neurological disorder in a premature infant.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in modulating a glucocorticoid receptor. In some embodiments, the second agent is an agent for treating amyotrophic lateral sclerosis (ALS), obesity, diabetes, cardiovascular disease, hypertension, Syndrome X, depression, anxiety, glaucoma, neurodegeneration, Alzheimer's disease, Parkinson's disease, Cushing's Syndrome, Cushing Disease, cancer, liver disease, osteoporosis, muscle frailty, a disorder caused by adrenal disease-related cortisol excess, addiction, psychosis, anorexia, cachexia, post-traumatic stress syndrome, post-surgical bone fracture, a GR-related metabolic disorders, major psychotic depression, mild cognitive impairment, dementia, hyperglycemia, a stress disorder, antipsychotic induced weight gain, delirium, cognitive impairment in depressed patients, postpartum psychosis, postpartum depression, and a neurological disorder in a premature infant. In some embodiments, the second agent is an agent for treating major psychotic depression, stress disorders or antipsychotic induced weight gain. In some embodiments, the second agent is an agent for treating nonalcoholic fatty liver disease and/or nonalcoholic steatohepatitis. In some embodiments, the second agent is an agent for treating an addiction disorder. In some embodiments, the second agent is an agent for treating cancer. In some embodiments, the second agent is an anti-cancer agent. In some embodiments, the second agent is a chemotherapeutic.

In some embodiments, any one of the low impurity compositions of the present invention, or a pharmaceutical composition of the present invention can be used for a method of treating a disorder or condition through modulating a glucocorticoid receptor.

In some embodiments, any one of the low impurity compositions of the present invention, or a pharmaceutical composition of the present invention can be used for a method of treating a disorder or condition through antagonizing a glucocorticoid receptor.

In some embodiments, any one of the low impurity compositions of the present invention, or a pharmaceutical composition of the present invention, can be used in the manufacture of a medicament for treating a disorder or condition through modulating a glucocorticoid receptor.

In some embodiments, any one of the low impurity compositions of the present invention, or a pharmaceutical composition of the present invention, can be used in the manufacture of a medicament for treating a disorder or condition through antagonizing a glucocorticoid receptor.

X. EXAMPLES

The following abbreviations are used in the methods below:

| | |
|---|---|
| ° C. | Degree Celsius |
| ACN | acetonitrile |
| aq | Aqueous |
| atm | Atmospheric pressure |
| Boc | t-butyloxycarbonyl |
| DIPEA | diisopropylethaylamine |
| eq or equiv | Equivalent |
| FA | Formic acid |
| g | Gram |
| HDPE | High density polyethylene |
| IPAC | isopropylacetate |
| Kg | kilogram |
| L | Liter |
| M | Molar |
| mbar | millibar |
| 2-MeTHF | 2-methyltetrahydrofuran |
| mins | minutes |
| mL | milliliter |
| MTBE | methyl t-butyl ether |

-continued

| | |
|---|---|
| nm | nanometers |
| NMR | Nuclear Magnetic Resonance |
| Parts | |
| ppm | Parts per million |
| r.t. | room temperature |
| THF | tetrahydrofuran |
| µm | micrometer |
| wt/wt | Weight by weight |

X-ray Powder Diffraction (XRPD). XRPD analyses were performed using a Panalytical Xpert Pro diffractometer equipped with a Cu X-ray tube and a Pixcel detector system. The isothermal samples were analysed in transmission mode and held between low density polyethylene films. The XRPD program used included the following parameters: (1) range 3-40° 2θ, (2) step size 0.013°, (3) counting time 99 sec, and (4) about 22 min run time. XRPD patterns were sorted using HighScore Plus 2.2c software.

Differential Scanning Calorimetry (DSC). DSC analyses were carried out on a Perkin Elmer Jade Differential Scanning Calorimeter. Accurately weighed samples were placed in crimped aluminium pans. Each sample was heated under nitrogen at a rate of 10° C./minute to a maximum of 300° C. Indium metal was used as the calibration standard. Temperatures were reported at the transition onset to the nearest 0.01 degree.

The reaction steps of the present invention can be performed for any suitable reaction time. For example, the reaction time can be for minutes, hours, or days. In some embodiments, the reaction time can be for several hours, such as at least eight hours. In some embodiments, the reaction time can be for several hours, such as at least overnight. In some embodiments, the reaction time can be for several days. In some embodiments, the reaction time can be for at least two hours. In some embodiments, the reaction time can be for at least eight hours. In some embodiments, the reaction time can be for at least several days. In some embodiments, the reaction time can be for about two hours, or for about 4 hours, or for about 6 hours, or for about 8 hours, or for about 10 hours, or for about 12 hours, or for about 14 hours, or for about 16 hours, or for about 18 hours, or for about 20 hours, or for about 22 hours, or for about 24 hours. In some embodiments, the reaction time can be for about 1 day, or for about two days, or for about three days, or for about four days, or for about five days, or for about six days, or for about a week, or for about more than a week.

The reaction steps of the present invention can be performed at any suitable reaction temperature. Representative temperatures include, but are not limited to, below room temperature, at room temperature, or above room temperature. Other temperatures useful in the methods of the present invention include from about −40° C. to about 65° C., or from about room temperature to about 40° C., or from about 40° C. to about 65° C., or from about 40° C. to about 60° C. In some embodiments, the reaction mixture can be at a temperature of about room temperature, or at a temperature of about 15° C., or at about 20° C., or at about 25° C. or at about 30° C., or at about 35° C., or at about 40° C., or at about 45° C., or at about 50° C., or at about 55° C., or at about 60° C., or at about 65° C.

Example 1. Preparation of Tert-butyl (R)-1-(4-fluorophenyl)-4a-(4-(trifluoromethyl)picolinoyl)-1,4,4a,5,7,8-hexahydro-6H-pyrazolo[3,4-g]isoquinoline-6-carboxylate

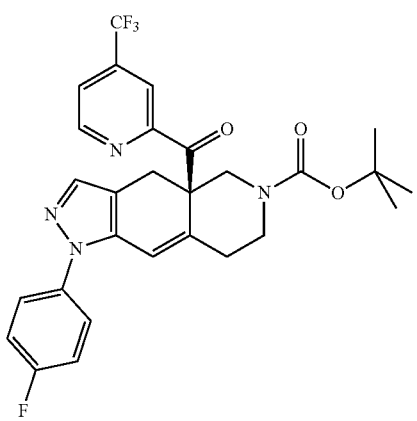 [SMILES: CC(C)(C)OC(=O)N1CCC2=Cc3c(cnn3-c3ccc(F)cc3)C[C@]2(C(=O)c2cc(C(F)(F)F)ccn2)C1]

0.7-0.8 parts 2-bromo-4-(trifluoromethyl)pyridine is added to 6.8 parts toluene. The solution is cooled under nitrogen to −5 to 5° C. 1.3-1.5 parts of the reagent, i-Propyl magnesium bromide (3.0M solution in 2-Me-THF), is added to the solution while maintaining a batch temperature at −5 to 5° C. The Grignard reaction occurs over ≥6 hours at −5 to 5° C. until reaction completion (HPLC, ≤15% 2-bromo-4-(trifluoromethyl)pyridine).

A solution of 1.0 part 6-(tert-butyl) 4a-methyl (R)-1-(4-fluorophenyl)-1,4,7,8-tetrahydro-6H-pyrazolo[3,4-g]isoquinoline-4a,6(5H)-dicarboxylate (Compound 9) in 7.0 parts toluene is added while maintaining the batch temperature at −5 to 5° C. The reaction mixture is allowed to warm to 15 to 25° C. and this temperature is maintained for at least 12 hours, continuing until the coupling reaction is complete (HPLC, ≤1.0% Compound 9 remains).

The reaction is quenched by the addition of 0.28 parts acetic acid in 10 parts water. The solution is stirred then allowed to settle. The aqueous phase is discarded and the organic phase washed with 12 parts aqueous hydrochloric acid. The aqueous phase is discarded and the organic phase is washed with 12 parts water. The aqueous phase is discarded. The product is dried through azeotropic distillation at ≤50 C (KF, ≤0.1% water; HPLC, ≤20 ppm 2-MeTHF). The product is isolated in toluene (5-8% w/w) and affords 1.1-1.3 parts (90-100% molar yield). The characterization data of the title compound matched that of Intermediate 29 of U.S. Pat. No. 8,859,774.

Example 2. Preparation Method I of (R)-(1-(4-fluorophenyl)-6-((1-methyl-1H-pyrazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone (Relacorilant)

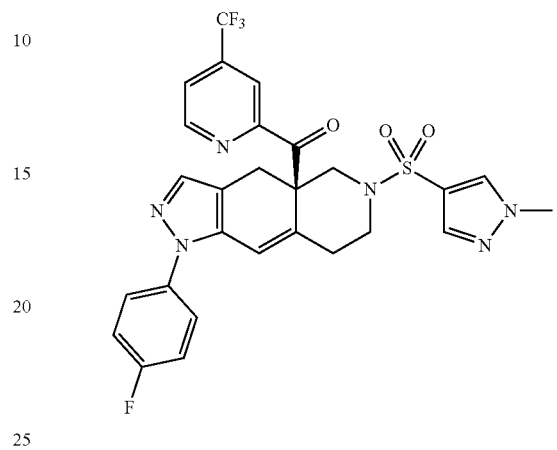

The target compound was prepared using the following steps.

Preparation of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone Tris-hydrobromic Acid

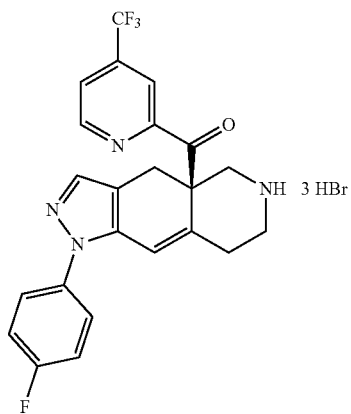 [SMILES: O=C(c1cc(C(F)(F)F)ccn1)[C@@]12CNCCC1=Cc1c(cnn1-c1ccc(F)cc1)C2 ; "3 HBr"]

The toluene solution of 1.0 part of the product from Example 1 is added to a vessel. 1.0-1.2 parts hydrogen bromide gas is added at a temperature of −5 to 5° C. until the reaction is complete (HPLC, ≤1.0% the product from Example 1 remains). The mixture is transferred to a filter dryer and washed with at least 2.6 parts toluene at a temperature of −5 to 5° C.

The solid is dried under vacuum/nitrogen at −5 to 10° C. for at least 24 hours and sampled every 12-24 hours (GC, ≤25% toluene remains). The tris-hydrobromic acid compound is isolated and affords 1.1-1.3 parts (85-100% molar yield).

Preparation of (R)-(1-(4-fluorophenyl)-6-((1-methyl-1H-pyrazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone 1.0 part the tris-hydrobromic acid intermediate from Step Two is added to 7.8 parts isopropyl acetate at −5 to 5° C. 0.3 parts pyrazolesulfonyl chloride and 1.2 parts triethylamine is added and stirring continued for a minimum of 3 hours the reaction is complete (HPLC, ≤2% of the tris-hydrobromic acid intermediate remains). The organic solution is washed with at least 8.8 parts water at 15-25° C. The organic phase is then washed with 3.7 parts HCl/water solution (adjusted to a pH of 4-5). The organic phase is then washed with 13 parts NaCl/water solution (adjusted to a pH of 5-6).

0.3 parts of silica gel is added the organic solution. The solution is filtered and rinsed with at least 1.2 parts isopropyl acetate. The mother liquor is concentrated under vacuum at ≤50° C. and a solvent exchange in acetone is performed (GC, ≤10% isopropyl acetate). The crude relacorilant is isolated in acetone (target 40% w/w) and affords 0.6-0.8 parts (70-90% molar yield) crude relacorilant. The characterization data of the crude relacorilant matched that of Example 18 of U.S. Pat. No. 8,859,774.

Example 3. Purification of (R)-(1-(4-fluorophenyl)-6-((1-methyl-1H-pyrazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone The product of Example 2 was purified by the following methods.

Preparative HPLC Purification

An HPLC column was pressure-packed with C18 using Isopropyl Alcohol. The chromatography resin was dedicated to relacorilant production, and the packed column was re-used for multiple cycles within each product lot. A use test was preformed to determine the collection time to collect the product fraction within the elution parameters given in Table 2

The packed column was equilibrated with 1-2 column volumes of Mobile Phase A. Crude relacorilant (1.0-1.5 kg) in solution was loaded onto the chromatography column at a rate of 3 L/min. The product was eluted from the column using a gradient of Mobile Phase B to Mobile Phase C over 100 minutes at a flow rate of 4.5 L/min. Fractionation was performed by separating the column eluant into multiple collection tanks in accordance with the established use test collection times. Following column fractionation, the column was washed with Buffer C for 10 minutes at a flow rate of 6.5 L/min to regenerate the packing material.

The column equilibration, loading, elution, fractionation and column washing was then repeated to yield additional fractions. Elution fractions in the collection tanks are sampled and tested for relacorilant purity and related substances. Elution fractions that meet the in-process acceptance criteria (HPLC: ≥98.0% purity, ≤0.6% Formula X-5, ≤0.20% individual impurities) are qualified as product fractions and pooled.

TABLE 1

Reverse Phase Chromatography Solution Compositions

| Solution | Component | Quantity |
| --- | --- | --- |
| Buffer A | Formic Acid | 1 mL per L |
|  | Purified Water | quantum sufficit to final volume |
| Mobile Phase A | Acetonitrile | 3% (v/v) |
|  | Buffer A | 97% (v/v) |
| Mobile Phase B | Acetonitrile | 48% (v/v) |
|  | Buffer A | 52% (v/v) |
| Mobile Phase C | Acetonitrile | 91% (v/v) |
|  | Buffer A | 9% (v/v) |

TABLE 2

Reverse Phase Chromatography Process Parameters

| Process Step | Parameter | Reverse Phase Purification Target Value/Range |
| --- | --- | --- |
| Column Packing | Packing Material | C18 |
|  | Column Packing Solvent | Isopropyl Alcohol |
|  | Packed Bed Volume | 50-60 L |
| Equilibration | Mobile Phase | Mobile Phase A |
|  | Equilibration time | 10 min |
|  | Flow Rate | 6.75 L/min |
| Product Loading | Product Load Qty | 1.0-1.5 kg |
|  | Load Flow Rate | 3 L/min |
| Elution | Mobile Phase | Mobile Phase B |
|  | Elution Gradient Time | 100 min |
| Column Regeneration/Storage | Elution Flow Rate | 4.5 L/min |
|  | Mobile Phase | Mobile Phase C |
|  | Regeneration Time | 10 min |
|  | Regeneration Flow Rate | 6.75 L/min |

MTBE/Heptane Purification

Following the preparative HPLC purification, the relacorilant fraction pool is further purified as described in the following process. The solution of relacorilant in ACN:FA: Water is saturated with sodium chloride and extracted with a total of ≥45 parts ethyl acetate. The ethyl acetate solution is washed with ≥30 parts NaCl/water solution. The organic phase is concentrated under vacuum at ≤50° C. (KF, ≤1%) to a concentration of 3 to 5 parts relacorilant in ethyl acetate. A solvent exchange is performed with MTBE concentrated under vacuum at ≤50° C. to ≥11 parts by volume of a relacorilant in MTBE solution (GC, ≤500 ethyl acetate). The relacorilant solution is filtered through a CUNO cartridge filter (HPLC, ≤0.30 Formula X-5, ≤0.20 Formula X-6, ≤0.15 Formula X-4, ≤0.10% unknown impurities).

The relacorilant in MTBE solution is slowly added to 10 parts heptane at 30 to 40° C. and the solution is cooled to −5 to 5° C. to precipitate the relacorilant. The relacorilant precipitate is collected and washed with >2 parts heptane. The wet cake is dried at ≤50° C. for >4 hr (GC, ≤15% MTBE, ≤15% heptane, ≤4 ppm methylbromide, ≤4 ppm 2-bromopropane, ≤4 ppm 1,4-dibromopentane). The purified relacorilant is isolated and affords 0.60-0.90 parts (60-90% molar yield) purified relacorilant.

Methanol Solvent Wash

The purified relacorilant was dissolved in 13.6 parts methanol. The methanol solution was concentrated under vacuum at ≤50° C. to ≥9 parts by volume of a solution of relacorilant in MTBE (GC, ≤300 ppm MTBE, ≤300 ppm heptane). The solution was slowly added through at 0.22 μm in-line filter into 15 parts water to precipitate the relacorilant. The relacorilant precipitate was collected by filtration and washed with at least 5 parts water (HPLC, ≤4 ppm 1-Methyl-1H-pyrazole-4-sulfonyl chloride, ≤4 ppm methyl 1-Methyl-1H-pyrazole-4-sulfonate, ≤4 ppm ethyl 1-Methyl-1H-pyrazole-4-sulfonate, ≤4 ppm isopropyl 1-Methyl-1H-pyrazole-4-sulfonate, ≤50 ppm formic acid). Relacorilant was then dried under vacuum (KF, ≤1.1%; GC, ≤4500 ppm isopropyl acetate, ≤4500 ppm acetone, ≤370 ppm acetonitrile, ≤4500 ppm ethyl acetate, ≤2700 ppm methanol, ≤5000 ppm heptane, ≤5000 ppm MTBE).

Example 4. Preparation Method II of (R)-(1-(4-fluorophenyl)-6-((1-methyl-1H-pyrazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone (Relacorilant)

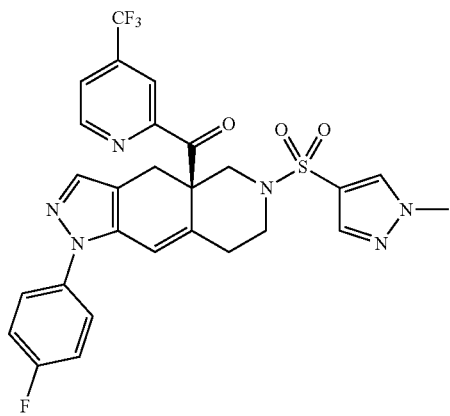 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

The target compound was prepared using the following steps.

Step 1. Preparation of Tert-butyl (R)-1-(4-fluorophenyl)-4a-(4-(trifluoromethyl)picolinoyl)-1,4,4a,5,7,8-hexahydro-6H-pyrazolo[3,4-g]isoquinoline-6-carboxylate

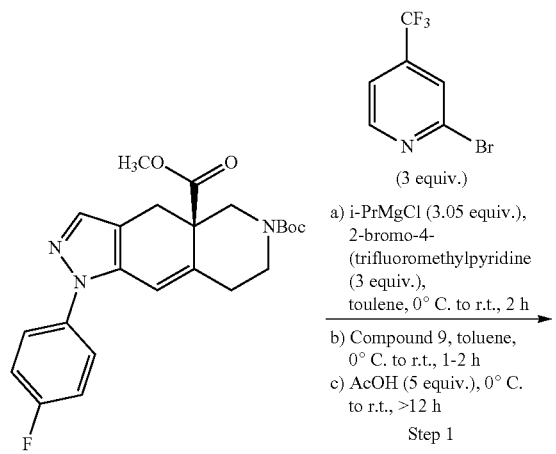

a) i-PrMgCl (3.05 equiv.), 2-bromo-4-(trifluoromethyl)pyridine (3 equiv.), toulene, 0° C. to r.t., 2 h
b) Compound 9, toluene, 0° C. to r.t., 1-2 h
c) AcOH (5 equiv.), 0° C. to r.t., >12 h Step 1

Compound 9

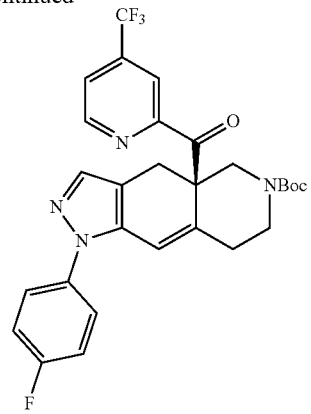

Step 1 relates to the addition of 2-Bromo-4-(trifluoromethyl)pyridine (3.0 equiv.) to 6-(tert-butyl) 4a-methyl (R)-1-(4-fluorophenyl)-1,4,7,8-tetrahydro-6H-pyrazolo[3,4-g]isoquinoline-4a,6(5H)-dicarboxylate (Compound 9; 1.0 equiv.) facilitated through halo-metal exchange using the Grignard reagent iPrMgCl (3.05 equiv.). During work-up the intermediate hemi-ketal is converted to the ketone and the Step 1 product is isolated as a solution in toluene and used directly in the next step.

1. Inert reactor with nitrogen via a vacuum purge.
2. Using residual vacuum, charge reactor with Toluene (40.0 Kg) via the solvent addition line.
3. Stir the contents of the reactor vigorously for at least 5 minutes.
4. Drain the contents of the reactor via the bottom outlet valve to suitable waste receiver.
5. Set up the reactor for distillation and place under full vacuum. Ensure the reactor is visually dry.
6. Charge 6-(tert-butyl) 4a-methyl (R)-1-(4-fluorophenyl)-1,4,7,8-tetrahydro-6H-pyrazolo[3,4-g]isoquinoline-4a,6(5H)-dicarboxylate (Compound 9; 7.2 Kg) to the reactor via the manway.
7. Inert the reactor with nitrogen.
8. Using residual vacuum, charge Toluene (31.2 Kg) to the reactor via the solvent addition line and start the stirrer.
9. Stir the contents of the reactor for at least 5 minutes at 25° C. to allow Compound 9 to dissolve.
10. Stop stirring and transfer the contents of the reactor into a tared clean plastic lined drum.
11. Using residual vacuum, charge Toluene (6.2 Kg) to the reactor via the solvent addition line.
12. Stir the contents of the reactor for at least 5 minutes.
13. Stop stirring and transfer the contents of the reactor into the plastic drum used in Step 10.
14. Using residual vacuum, charge Toluene (40.0 Kg) to the reactor via the solvent addition line.
15. Stir the content of the reactor for at least 2 minutes.
16. Stop stirring and drain the contents of the reactor via the bottom outlet valve into a drum for disposal.
17. Using residual vacuum, charge Toluene (100 Kg) to the reactor via the solvent addition line.
18. Pressure purge the reactor with nitrogen 3 times.
19. Charge 2-Bromo-4-(trifluoromethyl)pyridine (11.56 Kg) under vacuum via the reagent addition line.
20. Cool the contents of the reactor to 0° C.
21. Charge Isopropylmagnesium Chloride ca. 20% in THF (26.4 Kg) to the reactor via the reagent addition line over at least 20 minutes whilst maintaining a batch temperature below 5° C.

22. Age the contents of the reactor for at least 2 hours at 0° C.
23. Sample the reactor to determine conversion of 2-Bromo-4-(trifluoromethyl)pyridine to the Des-Bromo (89% conversion achieved as determined at 254 nm).
24. Charge the contents of the plastic lined drum from Steps 10 and 13 containing Compound 9 toluene solution to the reactor via the reagent addition line over at least 20 minutes, whilst maintaining a batch temperature below 5° C.
25. Warm the contents of the reactor to 20° C.
26. Age the contents of the reactor at 20° C. for at least 1 hour.
27. Sample the reactor to determine reaction conversion of Compound 9 to Step 1 product (100% conversion achieved at 210 nm).
28. Cool the contents of the reactor to 0° C.
29. Charge Acetic Acid (5.06 Kg) to the reactor via the solvent addition line over at least 20 minutes. Ensure that the batch temperature is maintained below 10° C. throughout the addition.
30. Warm the contents of the reactor to 20° C.
31. Sample the reactor to determine reaction profile and LCAP of Step 1 product (82.2% detected at 210 nm).
32. Age the contents of the reactor for a minimum of 12 hours at 22° C.
33. Charge Purified Water (132.2 Kg) to a visually clean drum and make up a 1M Hydrochloric Acid solution by charging Hydrochloric Acid 37% (14.2 Kg).
34. Using residual vacuum, charge half the contents of the drum of 1M Hydrochloric Acid (73.2 Kg) to the reactor via the solvent addition line.
35. Stir the contents of the reactor for at least 5 minutes, stop stirring, and allow the biphasic mixture to settle out.
36. Drain the lower aqueous layer into clean tared drums.
37. Using residual vacuum, charge the remainder of the 1M Hydrochloric Acid (73.2 Kg) to the reactor via the solvent addition line.
38. Stir the contents of the reactor for at least 5 minutes, stop stirring, and allow the biphasic mixture to settle out.
39. Drain the lower aqueous layer into clean tared drums.
40. Charge Sodium Hydrogen Carbonate (1.3 Kg) to a 75 L drum and then charge Purified Water (42.7 Kg) to the drum and mix until dissolved to generate a 3 wt % Sodium Hydrogen Carbonate solution.
41. Using residual vacuum, charge the contents of the drum containing 3 wt % Sodium Hydrogen Carbonate solution (44.0 Kg) to the reactor via the solvent addition line.
42. Stir the contents of the reactor for at least 5 minutes, stop stirring, and allow the biphasic mixture to settle out.
43. Drain the lower aqueous layer into clean tared drum.
44. Charge Purified Water (100 Kg) to a visually clean drum.
45. Using residual vacuum, charge Purified Water (72 Kg) from Step 44 to the reactor via the solvent addition line.
46. Stir the contents of the reactor for at least 15 minutes, stop stirring, and allow the biphasic mixture to settle out.
47. Drain the lower aqueous layer into clean tared drum.
48. Configure the reactor for distillation.
49. Keeping the contents of the reactor below 45° C., distil under reduced pressure to achieve approximately 72 L final volume.
50. Cool the contents of the reactor to 20° C.
51. Transfer the organic layer from the reactor into visually clean blue HDPE (High-Density Polyethylene) lined drum via a 10 μm cartridge filter.
52. Remove a sample from the drum to determine both the weight percent based on Step 1 product and reaction profile by HPLC (weight percent determined to be 13.99%).
53. Actual yield determined to be 99.54%.

The characterization data of the title compound matched that of Intermediate 29 of U.S. Pat. No. 8,859,774.

Step 2. Preparation of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic Acid

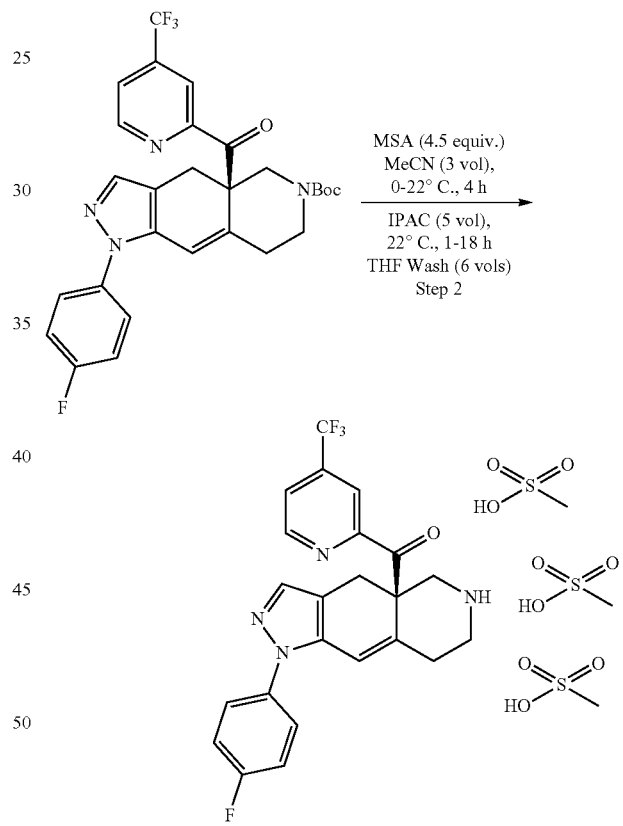

Step 2 relates to a Boc deprotection achieved using methane sulfonic acid (4.5 equiv.) and subsequent product isolation as the Tris MSA salt by means of crystallisation from the reaction mixture initiated using 0.25 mol % of Step 2 tris MSA salt seed.

1. Inert reactor with nitrogen via a vacuum purge.
2. Using residual vacuum, charge the solution of Step 1 Product (70 Kg, 8.90 Kg corrected) to the reactor via the solvent addition line, via an inline filter, and start the stirrer.
3. Inert the reactor via partial vacuum purge (−300 to −400 mbar)

4. Keeping the contents of the reactor below 40° C., distil under reduced pressure to achieve a final volume of approximately 18 L.
5. Using residual vacuum, charge Acetonitrile (71 Kg) to the reactor via the solvent addition line.
6. Keeping the contents of the reactor below 40° C., distil under reduced pressure to achieve a final volume of approximately 18 L.
7. Using residual vacuum, charge Acetonitrile (14 Kg) to the reactor via the solvent addition line.
8. Cool the contents of the reactor to 22° C.
9. Remove a sample from the reactor. Check the content of toluene by $^1$H NMR (Result: 1.135 wt/wt).
10. Cool the contents of the reactor to 0° C.
11. Charge Methanesulfonic Acid (7.1 Kg) to the reactor via the reagent addition line (over at least 15 minutes) using residual vacuum, whilst maintaining a batch temperature below 10° C.
12. Using residual vacuum, charge Acetonitrile (2 Kg) to the reactor via the reagent addition line.
13. Inert the reactor via partial vacuum purge (−300 to −400 mbar).
14. Slowly warm the contents of the reactor to 22° C., over at least 20 minutes.
15. Charge the reactor with Step 2 Product seed (30 g).
16. Age the contents of the reactor for at least 3 hours at 22° C.
17. Remove a sample from the reactor. Check the LCAP (liquid chromatography area percentage) of the Step 2 Product free base with respect to Step 1 Product (Result: >99%).
18. Charge Isopropyl acetate (39 Kg) to the reactor via the solvent addition line, over a minimum of 30 minutes, using a dosing pump.
19. Age the contents of the reactor for at least 1 hour at 22° C.
20. Remove a sample (approximately 30-50 mL) from the reactor. Filter the slurry and check the concentration of Step 2 Product free base in the liquors by HPLC (Result: 5.8 mg/ml).
21. Stop the stirrer, then discharge the contents of the reactor to a pressure filter and collect the liquors in a plastic lined drum.
22. Charge Tetrahydrofuran (24 Kg) to the reactor via the solvent addition line, using a dosing pump, and start the stirrer.
23. Stop the stirrer, then discharge the contents via the bottom outlet valve of the reactor to the pressure filter and collect the liquors in a plastic lined drum.
24. Charge Tetrahydrofuran (24 Kg) to the pressure filter via the spray ball and collect the liquors in a plastic lined drum.
25. Dewater the solid on the pressure filter under a stream of nitrogen.
26. Transfer the solid from the pressure filter on to visually clean trays and place in the tray dryer.
27. Place the dryer under vacuum and set the minimum nitrogen sweep.
28. Set the dryer to 40° C. and dry the solids to at least 18 hours.
29. Cool the dryer to 20° C. and return to atmospheric pressure.
30. Transfer the solid from the dryer into clean, tared, double bagged Anti-Static Polythene liners with two desiccant pouches between the liners and place the liners in a HDPE white keg.
31. Amount isolated, 9.6 Kg Step 2 tris MSA salt, 60.5 wt % of Step 2 free base, yield 79.1%.

TABLE 3

XRPD of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid

| Degrees 2-θ | Relative Intensity |
|---|---|
| 4.968° | 22.2% |
| 5.003° | 26.5% |
| 9.928° | 60.4% |
| 10.376° | 14.3% |
| 11.732° | 18.2% |
| 11.783° | 11.5% |
| 13.461° | 19.6% |
| 13.484° | 12.8% |
| 13.628° | 6.6% |
| 13.857° | 11.8% |
| 13.876° | 2.9% |
| 14.094° | 3.4% |
| 14.486° | 24.3% |
| 14.600° | 6.4% |
| 14.534° | 27.9% |
| 14.849° | 7.3% |
| 14.903° | 3.6% |
| 15.757° | 12.1% |
| 15.790° | 3.4% |
| 15.886° | 15.2% |
| 16.517° | 72.6% |
| 17.583° | 59.0% |
| 17.864° | 38.7% |
| 18.153° | 91.1% |
| 18.316° | 100.0% |
| 19.046° | 53.4% |
| 19.743° | 79.2% |
| 19.743° | 79.2% |
| 20.225° | 14.5% |
| 20.361° | 9.2% |
| 20.809° | 25.2% |
| 21.136° | 11.1% |
| 21.845° | 8.1% |
| 22.570° | 10.1% |
| 22.658° | 5.7% |
| 22.758° | 4.9% |
| 22.882° | 30.5% |
| 23.098° | 5.8% |
| 23.398° | 40.9% |
| 23.517° | 19.6% |
| 23.720° | 17.9% |
| 23.729° | 18.4% |
| 24.235° | 4.4% |
| 25.145° | 3.1% |
| 25.270° | 33.2% |
| 25.583° | 6.4% |
| 26.042° | 4.1% |
| 26.920° | 19.1% |
| 27.149° | 7.3% |
| 27.193° | 10.1% |
| 27.645° | 4.7% |
| 27.918° | 5.0% |
| 28.152° | 5.0% |
| 29.329° | 7.1% |
| 29.558° | 4.5% |
| 29.701° | 7.7% |
| 30.161° | 10.4% |
| 30.582° | 3.1% |
| 31.697° | 7.7% |
| 31.905° | 4.2% |

Step 3. Preparation of (R)-(1-(4-fluorophenyl)-6-((1-methyl-1H-pyrazol-4-yl)sulfonyl)-1,4,5,6,7,8-hexahydro-4aH-pyrazolo[3,4-g]isoquinolin-4a-yl)(4-(trifluoromethyl)pyridin-2-yl)methanone

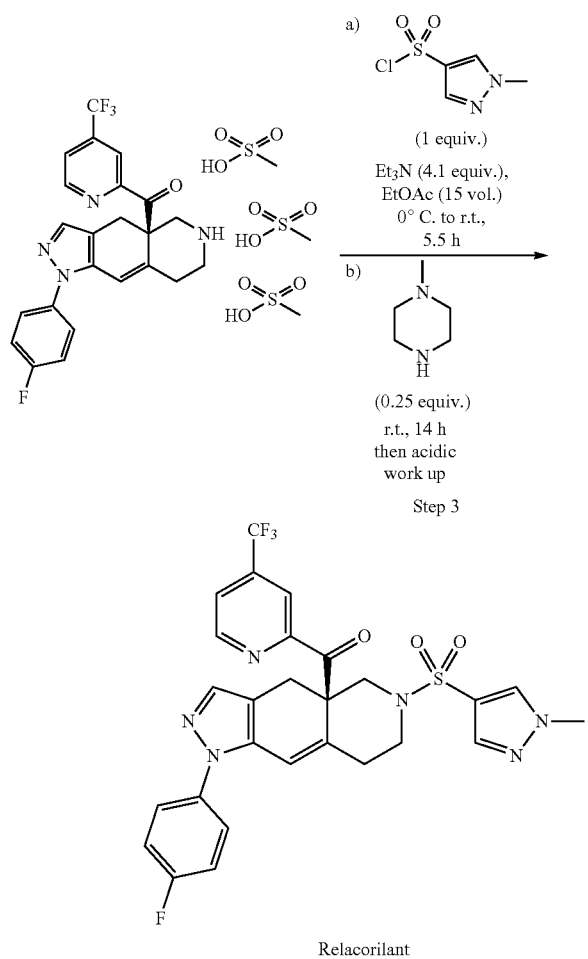

Relacorilant

The Step 2 Tris MSA salt in ethyl acetate, with triethylamine (4.1 eq.) is reacted with 1-Methyl-1H-pyrazole-4-sulfonyl chloride (1.0 eq.). Once reaction completion is achieved as determined by HPLC, excess sulfonyl chloride is removed by reaction with the scavenging agent (N-Methylpiperazine, 0.25 eq.). The reaction is then worked up by washing with 1M HCl followed by water. A solvent exchange into methanol is performed and relacorilant is precipitated as an amorphous solid by slow addition to water at ambient temperature.

1. Inert reactor with nitrogen.
2. Charge Step 2 product (Tris MSA salt) (0.779 Kg, 0.474 Kg corrected (free base) to the reactor.
3. Charge Ethyl Acetate (10.08 Kg) to the reactor using a dosing pump and agitate.
4. Inert the reactor via partial vacuum purge (−300 to −400 mbar).
5. Cool the contents of the reactor to −5° C.
6. Charge Triethylamine (0.443 Kg) using a dosing pump (over at least 5 minutes), whilst maintaining a batch temperature of 5° C.
7. Age the contents of the reactor at −5° C. for at least 5 minutes.
8. Charge 1-Methyl-1H-pyrazole-4-sulfonyl chloride (0.198 Kg) to a clean, tared HDPE drum and charge Ethyl Acetate (2.012 Kg) to the drum.
9. Ensure thorough mixing of the contents of the drum for complete dissolution.
10. Charge the contents of the drum to the reactor via the solvent addition line using a dosing pump (over at least 5 minutes), whilst maintaining a batch temperature below 5° C.
11. Charge Ethyl Acetate (1.0 Kg) to the reactor via the dosing pump setup from Step 10.
12. Warm the contents of the reactor to 20° C., over at least 15 minutes.
13. Age the contents of the reactor for at least 4 hours at 20° C.
14. Remove a sample from the reactor and analyse using HPLC to check the LCAP of relacorilant with respect to Step 2 (free base), result: 99.1% at 243 nm.
15. Charge N-Methylpiperazine (26.7 g) to the reactor using a dosing pump.
16. Age the contents of the reactor for at least 14 hours at 20° C.
17. Remove a sample from the reactor and analyse by HPLC to determine the consumption of 1-Methyl-1H-pyrazole-4-sulfonyl chloride, result: sulfonyl chloride not detected.
18. Charge Purified Water (7.0 Kg) to a visually clean 25 L black Anti-Static drum followed by concentrated hydrochloric acid (0.77 Kg) to generate a 1.0M HCl solution.
19. Charge (3.93 Kg) of the 1.0M HCl solution to the reactor via the solvent addition line.
20. Stir the contents of the reactor for at least 5 minutes, stop the stirrer and allow the biphasic mixture to settle out.
21. Drain the lower aqueous layer via the bottom outlet valve into a 200 L plastic lined drum.
22. Charge (3.88 Kg) of the 1.0M HCl solution to the reactor via the solvent addition line.
23. Stir the contents of the reactor for at least 5 minutes, stop the stirrer and allow the biphasic mixture to settle out.
24. Drain the lower aqueous layer via the bottom outlet valve into a 200 L plastic lined drum.
25. Charge Purified Water (3.92 Kg) via the solvent addition line using the dosing pump, and start the stirrer.
26. Stir the contents of the reactor for at least 5 minutes, stop stirring, and allow the biphasic mixture to settle out.
27. Drain the lower aqueous layer via the bottom outlet valve into a 200 L plastic lined drum.
28. Charge Purified Water (3.91 Kg) via the solvent addition line using the dosing pump, and start the stirrer.
29. Stir the contents of the reactor for at least 5 minutes, stop stirring, and allow the biphasic mixture to settle out.
30. Drain the lower aqueous layer via the bottom outlet valve into a 200 L plastic lined drum.
31. Charge Purified Water (3.92 Kg) via the solvent addition line using the dosing pump, and start the stirrer.
32. Stir the contents of the reactor for at least 5 minutes, stop stirring, and allow the biphasic mixture to settle out.

33. Drain the lower aqueous layer via the bottom outlet valve into a 200 L plastic lined drum.
34. Drain the contents of the reactor into a clean, tared 25 L drum (mass discharged, 12.31 Kg).
35. Remove a sample from the drum and analyse to determine assay yield of relacorilant (Result: 644.30 g, 103.1%).
36. Assemble an inline filter, connecting the outlet of a Whatman filter to Rotary Evaporator.
37. Using residual vacuum, transfer the contents of the 25 L drum through the Whatman filter to Rotary Evaporator.
38. Concentrate the relacorilant solution from Step 37, to achieve a final volume of approximately 1.5 L.
39. Charge Methanol (6.16 Kg) to the Rotary Evaporator.
40. Concentrate the relacorilant solution from Step 39, to achieve a final volume of approximately 3.0 L.
41. Remove a sample and analyse the residual Ethyl Acetate level by $^1$H NMR (Result: 1.87% wt/wt Ethyl Acetate).
42. Transfer the relacorilant solution from Step 40 into a clean, tared 5 L Schott Bottle.
43. Charge Methanol (4.0 Kg) to the reactor via the solvent addition line using a dosing pump, and agitate for at least 5 minutes.
44. Transfer the contents of the reactor into a clean, plastic lined drum labelled as waste.
45. Charge Purified Water (11.68 Kg) to the reactor via the solvent addition line using a dosing pump, and start the stirrer.
46. Under rapid agitation (>90 rpm) charge the contents of the 5 L Schott Bottle containing relacorilant solution to the reactor, over at least 30 minutes, using a dosing pump via the reagent addition line (N.B. Agitation of ~160 rpm was used during addition. After addition complete, agitation speed reduced to ~50 rpm).
47. Stir the contents of the reactor for at least 12 hours at 20° C.
48. Remove a sample from the reactor, filter and analyse by HPLC to check concentration of relacorilant in the liquors.
49. Stop the stirrer, discharge the contents of the reactor to a filter and collect the liquors in a tared plastic lined drum.
50. Charge Purified Water (2.34 Kg) to the reactor via the solvent addition line using a dosing pump.
51. Agitate the contents of the reactor for at least 5 minutes at 20° C.
52. Stop the stirrer, discharge the contents of the reactor to a filter and collect the liquors in a tared plastic lined drum.
53. Dewater the cake in the filter with nitrogen for at least 10 minutes.
54. Transfer the solid from the filter on to visually clean trays, place the trays in the dryer.
55. Turn on the dryer and set the temperature to 50° C.
56. Dry the solid in the dryer for a minimum of 15 hours under vacuum with a sweep of nitrogen.
57. Transfer the solid from the dryer into clean, tared, double-bagged Anti-Static Polythene liners with two desiccant pouches between the liners and place the liners in a HDPE keg.
58. Yield: 606 g, 97.0%.

The characterization data of the title compound matched that of Example 18 of U.S. Pat. No. 8,859,774.

Example 5. Purity Profile

The impurity profile of the compounds of Example 3 and Example 4 was determined.

TABLE 4

Impurities

| Impurity | Example 3 % (w/w) | Example 4 % (w/w) | Example 18 USPN 8,859,774 % (w/w) |
|---|---|---|---|
| Purity | 99.5 | 99.6 | 94.7 |
| Formula X-4 | ND | ND | 0.86 |
| Formula X-5 | 0.11 | 0.14 | 0.20 |
| Formula X-6 | <0.05 | ND | 0.16 |
| Formula X-D | 0.11 | 0.12 | ND |
| Formula X-E | 0.13 | 0.06 | ND |
| Formula X-F | 0.05 | ND | ND |
| Total Impurities | 0.5 | 0.4 | 5.3 |

ND = Not detected (LOD = 0.02%); LOQ = 0.05%

TABLE 5

Additional Impurities

| Impurity | Example 3 (ppm) | Example 4 (ppm) | Example 18 USPN 8,859,774 (ppm) |
|---|---|---|---|
| Methylbromide | <3 | ND | ND |
| 2-Bromopropane | <3 | ND | ND |
| 1,4-dibromopentane | <3 | ND | ND |
| 1-Methyl-1H-pyrazole-4-sulfonylchloride | ND | <4 | 2 |
| Methyl 1-methyl-1H-pyrazole-4-sulfonate | ND | <4 | 1.5 |
| Ethyl 1-methyl-1H-pyrazole-4-sulfonate | ND | <4 | ND |
| Isopropyl 1-methyl-1H-pyrazole-4-sulfonate | ND | <4 | ND |

ND = Not detected (LOD = 1 ppm); LOQ = 1.5-4 ppm

Example 6. Preparation of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone Oxalic Acid

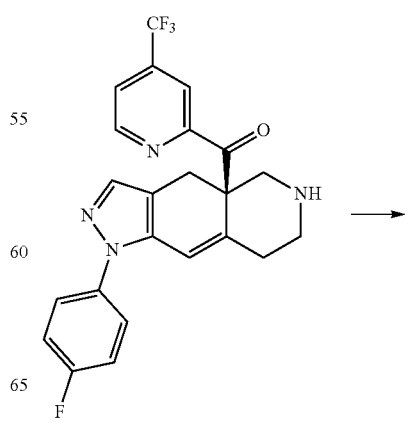

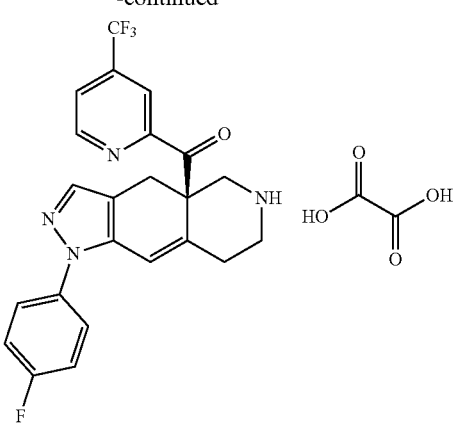

Approximately 180 mg of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone was dissolved in acetonitrile, forming a stock solution. Oxalic acid was separately dissolved in acetonitrile and added to the stock solution in equimolar amounts. The resulting oil crystallized. Crystals were then washed with 5 mL of acetonitrile using a Buchner funnel and flask. The crystals were then dried under nitrogen flow for 3 hour using a Buchner funnel and flask.

TABLE 6

XRPD of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone oxalic acid

| Degrees 2-θ | Relative Intensity |
| --- | --- |
| 10.619° | 39.3% |
| 12.263° | 29.2% |
| 12.955° | 28.4% |
| 13.520° | 9.3% |
| 15.600° | 100.0% |
| 16.226° | 14.3% |
| 16.791° | 9.6% |
| 17.139° | 12.0% |
| 18.193° | 12.0% |
| 19.280° | 6.8% |
| 19.866° | 20.2% |
| 20.171° | 6.8% |
| 21.106° | 8.3% |
| 21.704° | 16.0% |
| 22.902° | 11.2% |
| 23.674° | 11.3% |
| 24.216° | 4.9% |
| 24.604° | 15.0% |
| 25.276° | 26.2% |
| 26.867° | 6.9% |
| 27.475° | 4.6% |
| 28.196° | 8.1% |
| 28.847° | 3.8% |
| 29.496° | 2.9% |
| 30.587° | 2.5% |
| 32.032° | 2.9% |
| 33.194° | 3.0% |
| 39.677° | 1.3% |
| 6.141 | 47.8% |
| 8.376° | 39.1% |

Example 7. Preparation of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-hydrochloric Acid

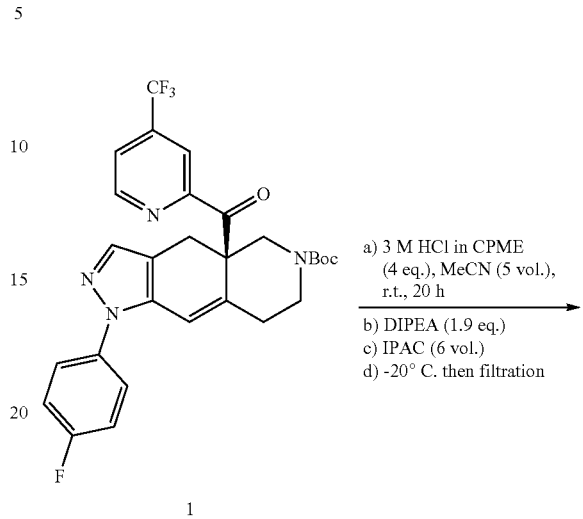

1
(16 g)

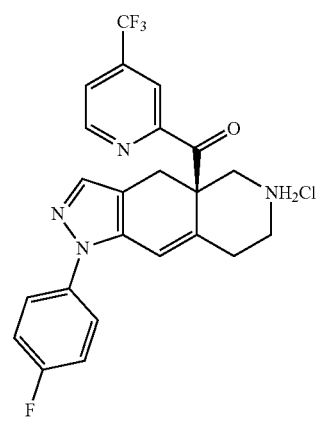

2·HCl (9.46 g)
72% isolated
99.6 LCAP
93.3 wt% of free base
(13% loss in liquors)

The procedure for Boc deprotection and crystallisation from Scheme 5 is described below.

1. A vessel was charged with 1 (16.0 g, 95.1 wt %, 28.05 mmol, 1.0 eq.) and MeCN (80 mL, 5 vol.) and cooled to 0° C.
2. HCl (3 M in CPME, 36.8 mL, 112.2 mmol, 4.0 eq.) was added over 2 min maintaining an internal temperature below 10° C.
3. The reaction mixture was warmed to room temperature and aged for 20 h. Reaction conversion was 98% as determined by HPLC LCAP (FFCAM method).
4. DIPEA (2.0 mL, 11.7 mmol, 0.4 eq.) was added at room temperature over 30 seconds.
5. The reaction mixture was seeded with 2·HCl (ca. 5 mg) and aged for 20 min at room temperature.
6. DIPEA (7.1 mL, 44.4 mmol, 1.5 eq.) was added over 45 min at room temperature using a syringe pump and aged for an additional 30 min. Liquor loss of 2 was 19.9 mg/mL as determine by HPLC.

7. IPAC (96 mL, 6 vol.) antisolvent was added over 1 h and the slurry was aged at room temperature for 16 h. Liquor loss of 2 were 8.2 mg/mL as determined by HPLC.

8. The slurry was cooled to −20° C. and aged for 2 h. Liquor loss of 2 was 7.8 mg/mL as determined by HPLC.

9. The slurry was filtered under N2, deliquored with MeCN (16 mL, 1 vol.), dried under vacuum at 40° C. for 16 h to give 2·HCl in 72% isolated yield (9.57 g, 99.6 LCAP purity, 93.3 wt % with respect to 2) as a white crystalline solid. Mother liquors contained 13% assay yield of 2.

TABLE 7

XRPD of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone hydrochloric acid

| Degrees 2-θ | Relative Intensity |
|---|---|
| 11.484° | 14.1% |
| 13.485° | 26.3% |
| 14.175° | 3.0% |
| 14.792° | 24.1% |
| 15.346° | 41.9% |
| 15.878° | 6.5% |
| 16.781° | 7.8% |
| 17.264° | 3.0% |
| 17.728° | 23.3% |
| 18.310° | 23.8% |
| 19.173° | 21.7% |
| 19.950° | 9.0% |
| 21.169° | 13.1% |
| 22.049° | 44.8% |
| 22.380° | 3.7% |
| 23.061° | 100.0% |
| 23.508° | 20.0% |
| 24.492° | 56.9% |
| 25.237° | 21.0% |
| 26.877° | 14.1% |
| 27.187° | 14.9% |
| 27.488° | 9.1% |
| 28.118° | 14.9% |
| 28.705° | 1.4% |
| 29.235° | 7.0% |
| 30.100° | 14.6% |
| 30.459° | 2.8% |
| 30.934° | 6.0% |
| 32.373° | 11.4% |
| 32.842° | 3.2% |
| 33.365° | 5.7% |
| 33.964° | 2.9% |
| 35.804° | 2.6% |
| 36.249° | 2.1% |
| 36.662° | 2.1% |
| 37.099° | 1.8% |
| 37.828° | 2.0% |
| 38.305° | 1.6% |
| 7.039° | 27.4% |
| 8.126° | 14.0% |
| 9.973° | 2.1% |

Example 8. Preparation of [(4aR)-1-(4-Fluorophenyl)-1,4,5,6,7,8-hexahydro-6-[(2-methyl-2H-1,2,3-triazol-4-yl)sulfonyl]-4aH-pyrazolo[3,4-g]isoquinolin-4a-yl][4-(trifluoromethyl)-2-pyridinyl]methanone

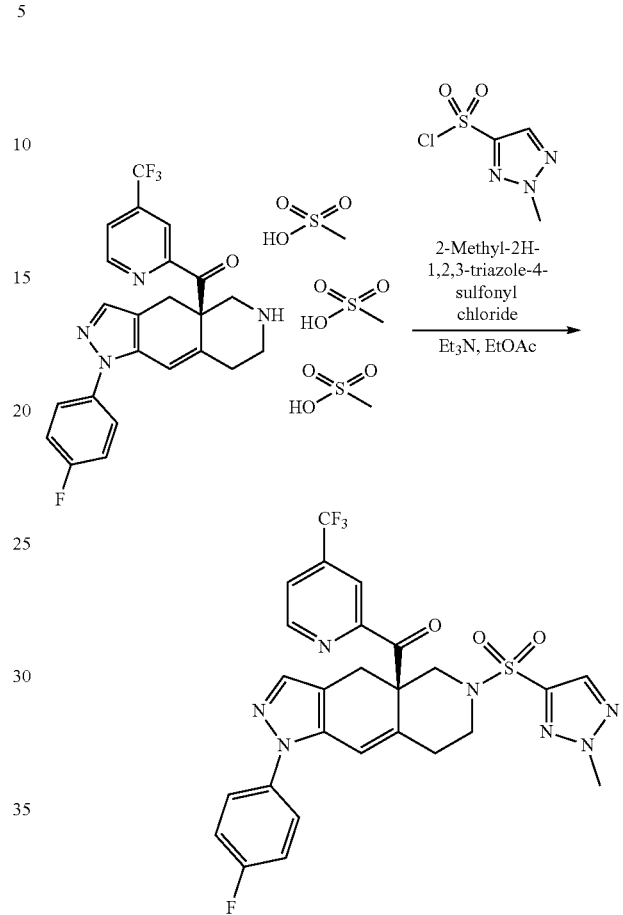

The target compound was prepared using the following steps.

The Step 2 Tris MSA salt is suspended in ethyl acetate and cooled to 0° C., then charged with triethylamine (4.1 eq.) to form a solution followed by addition of 2-Methyl-2H-1,2,3-triazole-4-sulfonyl chloride (1.0 eq.). Once reaction completion is achieved as determined by HPLC, excess sulfonyl chloride is removed by reaction with the scavenging agent (N-Methylpiperazine, 0.25 eq.). The reaction is then worked up by washing with 1M aqueous hydrochloric acid followed by 3% (w/w) Sodium Hydrogen Carbonate solution in water. A solvent exchange into ethanol is performed and the title compound is precipitated from a mixture of ethanol, acetone and water as an amorphous solid. The title compound is isolated by filtration, washed with water, and dried under vacuum at elevated temperature.

1. A vessel was rinsed with Ethyl Acetate and dried under vacuum.
2. Step 2 Tris MSA salt [12.81 kg (7.81 kg corrected)] and Ethyl Acetate (161.6 kg) were charged to the vessel and the contents cooled to 0° C.
3. Triethylamine (7.32 kg) was charged to the vessel over 10 minutes, maintaining the batch temperature<5° C. and the line rinsed with ethyl acetate.
4. The contents were aged at <5° C. for >1 hour.

5. 2-Methyl-2H-1,2,3-triazole-4-sulfonyl chloride ethyl acetate stream [47.0 kg (3.20 kg corrected)] was charged to the vessel, maintaining the batch temperature.
6. The contents were warmed to 20° C. over 25 minutes and aged at this temperature for 2 hours.
7. The conversion was analysed by HPLC.
8. N-methylpiperazine (0.44 kg) was charged to the vessel over 5 minutes.
1. The batch was aged at 20° C. for 16 hours.
9. 1.0M HCl solution (129.3 kg) was charged to the vessel, the biphasic mixture allowed to settle, and the aqueous layer drained. This step was repeated again.
10. 1.0M HCl solution (64.6 kg) was charged to the vessel, the biphasic mixture allowed to settle, and the aqueous layer drained.
11. 3 wt % sodium hydrogen carbonate solution (65.3 kg) was charged to the vessel, the biphasic mixture allowed to settle, and the aqueous layer drained.
12. Purified Water (64.0 kg) was charged to the vessel, the biphasic mixture allowed to settle, and the aqueous layer drained. This step was repeated again.
13. The solution of the title compound was discharged into 2 drums.
14. The title compound solution was charged into the second vessel through an in-line filter and concentrated from approximately 190 L to 38 L under reduced pressure, maintaining a batch temperature below 45° C.
15. Ethanol (151.3 kg) was charged to the vessel and the stream was concentrated from approximately 230 L to 38 L under reduced pressure, maintaining a batch temperature below 45° C.
16. The title compound solution was transferred into a clean plastic lined drum.
17. Purified Water (230.6 kg) was charged to the vessel via an in-line filter.
18. The title compound solution was charged to the vessel over 30 minutes. The slurry was aged for 30 minutes to ensure that gumming did not occur.
19. The slurry was filtered, washing the filter cake with Purified Water (37.9 Kg).
20. The wet cake was dewatered under a stream of nitrogen.
21. The wet cake was dried in a vacuum oven at 40° C.

The title compound was isolated as an off-white solid. Total yield: 9.810 kg (94.6% yield). The characterization data of the title compound matched that of Example 11CE of U.S. Pat. No. 8,859,774.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A method of preparing a compound of Formula J:

(J)

[Chemical structure of Formula J]

or a pharmaceutically acceptable salt thereof, comprising:
(a) forming a first reaction mixture comprising a compound of Formula IIb:

(IIb)

[Chemical structure of Formula IIb with $[HX]_n$]

and
a sulfonyl chloride:

[Chemical structure of sulfonyl chloride with $X^1$ and N-methyl pyrazole]

to prepare the compound of Formula J in a yield of at least 60% and a purity of at least 98%,
wherein
$X^1$ is —CH= or —N=;
HX is an acid solvate of HBr, or

[Chemical structure HO-S(=O)(=O)-$R^1$], wherein R¹ is $C_{1-6}$ alkyl; and subscript n is from 1 to 4.

2. The method of claim 1, preparing the compound of Formula I:

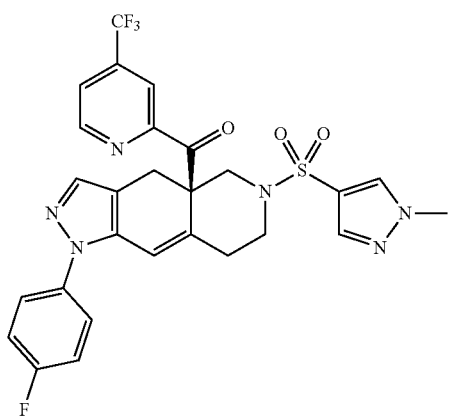

(I)

or a pharmaceutically acceptable salt thereof, comprising:

(a) forming the first reaction mixture comprising the compound of Formula IIb:

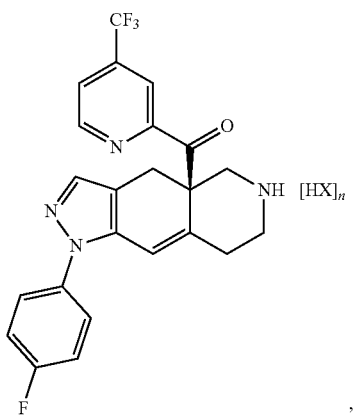

(IIb)

and 1-methyl-1H-pyrazole-4-sulfonyl chloride:

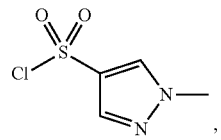

to prepare the compound of Formula I in a yield of at least 60% and a purity of at least 98%, wherein HX is the acid solvate; and subscript n is from 1 to 4.

3. The method of claim 1, wherein HX is HBr.

4. The method of claim 3, for preparing the compound of Formula I:

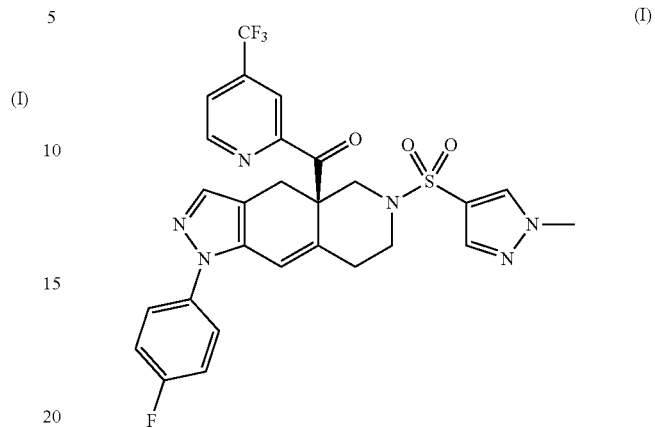

(I)

or a pharmaceutically acceptable salt thereof, comprising:

(a) forming the first reaction mixture comprising a compound of Formula IIb-1:

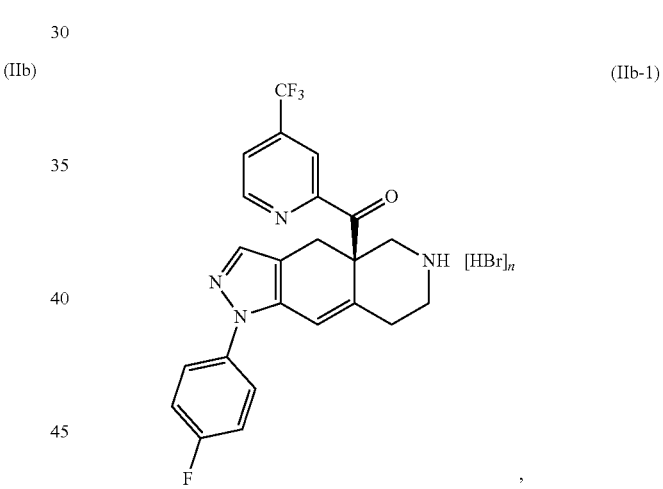

(IIb-1)

and 1-methyl-1H-pyrazole-4-sulfonyl chloride:

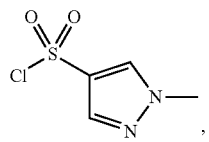

to prepare the compound of Formula I in a yield of at least 60% and a purity of at least 98%, wherein the compound of Formula I contains less than 1% (w/w) of a compound of Formula X-5:

(X-5)

and wherein subscript n is from 1 to 4.

5. The method of claim 4, wherein the first reaction mixture further comprises a non-nucleophilic amine base.

6. The method of claim 5, wherein the non-nucleophilic amine base comprises trimethyl amine, triethylamine, N,N-diisopropyl ethylamine (DIPEA), N,N-dimethyl isopropylamine (DIMPA), 1-ethylpiperidine, N-methylmorpholine, N-methylpyrrolidine, pyridine, N,N-dimethylaniline, N,N-diethylaniline, 2,6-lutidine, 2,4,6-collidine, 4-dimethyl aminopyridine (DMAP), quinuclidine, 4-pyrrolidinopyridine, 1,4-diazabicyclo[2.2.2]octane (DABCO), or mixtures thereof.

7. The method of claim 5, wherein the non-nucleophilic amine base comprises triethyl amine.

8. The method of claim 4, wherein the sulfonyl chloride is present in a molar ratio of 1.2 to 2.3 to the compound of Formula IIb-1.

9. The method of claim 4, further comprising after step (a):
(a1) mixing the first reaction mixture with water having a pH of between 4 and 5 to form a first organic phase and a first aqueous phase;
(a2) mixing the first organic phase with water and sodium chloride wherein the water has a pH of between 5 and 6; and
(a3) mixing the first organic phase and silica gel.

10. The method of claim 4, wherein the compound of Formula IIb-1 is prepared by the step of:
(b) forming a second reaction mixture comprising a compound of Formula IIa:

(IIa)

and gaseous HBr, to form the compound of Formula IIb-1 having the structure:

3 HBr

11. The method of claim 4, wherein the compound of Formula I is prepared by the steps of:
(b) forming the second reaction mixture comprising a compound of Formula IIa:

(IIa)

and gaseous HBr, to form the compound of Formula IIb-1 having the structure:

3 HBr and (a) forming the first reaction mixture comprising the compound of Formula IIb-1:

triethylamine, and 1-methyl-1H-pyrazole-4-sulfonyl chloride:

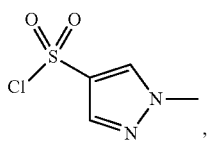

wherein the sulfonyl chloride is present in a molar ratio of about 1.2 to the compound of Formula IIb-1;

(a1) mixing the first reaction mixture with water having a pH of between 4 and 5 to form a first organic phase and a first aqueous phase;

(a2) mixing the first organic phase with water and sodium chloride wherein the water has a pH of between 5 and 6; and (a3) mixing the first organic phase and silica gel to prepare the compound of Formula I in a yield of at least 60% and a purity of at least 98%, wherein the compound of Formula I contains less than 1% (w/w) of the compound of Formula X-5:

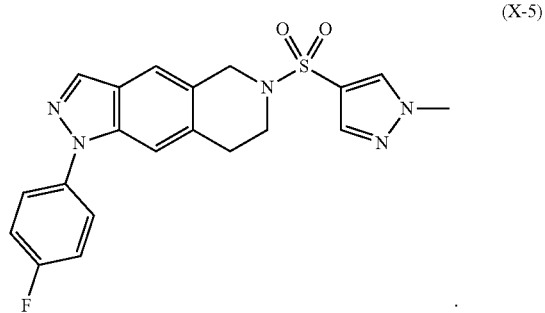 [SMILES: Cn1cc(S(=O)(=O)N2CCc3cc4c(cnn4-c4ccc(F)cc4)cc3C2)cn1]

(X-5)

12. The method of claim 10, wherein the compound of Formula IIa is prepared by:

(c) forming a third reaction mixture comprising a Grignard reagent, a compound of Formula III:

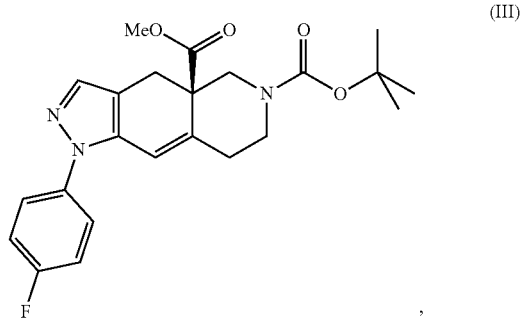 [SMILES: COC(=O)[C@]12Cc3cnn(-c4ccc(F)cc4)c3C=C1CCN(C(=O)OC(C)(C)C)C2]

(III)

and
2-bromo-4-(trifluoromethyl)pyridine:

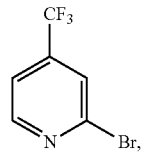

wherein the pyridine is present in a molar ratio of 1.0 to 1.5 to the compound of Formula III, and wherein the Grignard reagent is present in a molar ratio of 1.5 to 1.7 to the compound of Formula III, to prepare the compound of Formula IIa.

13. The method of claim 12, wherein the Grignard reagent comprises iPrMgCl or iPrMgBr.

14. The method of claim 12, wherein the Grignard reagent comprises iPrMgBr.

15. The method of claim 12, wherein the third reaction mixture further comprises a third solvent comprising tetrahydrofuran, 2-methyltetrahydrofuran, toluene or xylene.

16. The method of claim 15, wherein the third solvent comprises 2-methyltetrahydrofuran and toluene.

17. The method of claim 12, further comprising the steps of:

(c1) adding an acid and water to the third reaction mixture to form a workup mixture; and (c2) distilling the workup mixture to form an intermediate mixture comprising the compound of Formula IIa, 2-methyltetrahydrofuran in an amount of less than 100 ppm, and water in an amount of less than 0.5% (w/w).

18. The method of claim 17, wherein the acid comprises formic acid, acetic acid, propanoic acid, butyric acid, hexanoic acid, octanoic acid, trifluoroacetic acid, or mixtures thereof.

19. The method of claim 17, wherein the acid comprises acetic acid.

20. The method of claim 19, wherein the method of preparing the compound of Formula I comprises:

(c) forming the third reaction mixture comprising iPrMgBr, 2-methyltetrahydrofuran, toluene, the compound of Formula III:

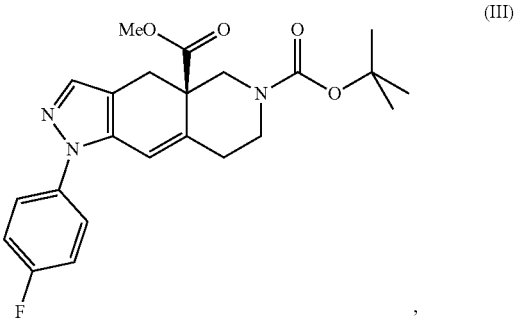 [SMILES: COC(=O)[C@]12Cc3cnn(-c4ccc(F)cc4)c3C=C1CCN(C(=O)OC(C)(C)C)C2]

(III)

and
2-bromo-4-(trifluoromethyl)pyridine:

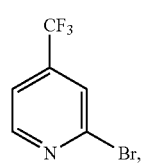

wherein the pyridine is present in the molar ratio of about 1.4 to the compound of Formula III, and wherein the Grignard reagent is present in the molar ratio of about 1.65 to the compound of Formula III, to prepare the compound of Formula IIa:

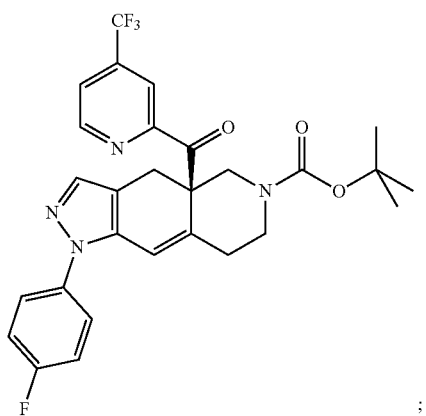
(IIa)

(c1) adding acetic acid and water to the third reaction mixture to form the workup mixture;
(c2) distilling the workup mixture to form an intermediate mixture comprising the compound of Formula IIa, 2-methyltetrahydrofuran in an amount of less than 100 ppm, and water in an amount of less than 0.5% (w/w);
(b) forming the second reaction mixture comprising the intermediate mixture and gaseous HBr, to form the compound of Formula IIb-1 having the structure:

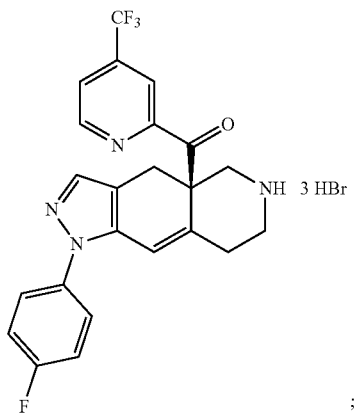 [SMILES: O=C(c1cc(C(F)(F)F)ccn1)[C@@]12CNCCC1=Cc1c(cnn1-c1ccc(F)cc1)C2 ; "3 HBr"]

and
(a) forming the first reaction mixture comprising the compound of Formula IIb-1, triethylamine, and 1-methyl-1H-pyrazole-4-sulfonyl chloride:

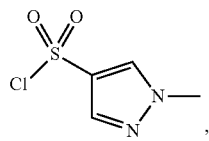
, wherein the sulfonyl chloride is present in the molar ratio of about 1.2 to the compound of Formula IIb-1, to prepare the compound of Formula I in the yield of at least 60% and the purity of at least 98%, wherein the compound of Formula I contains less than 1% (w/w) of the compound of Formula X-5:

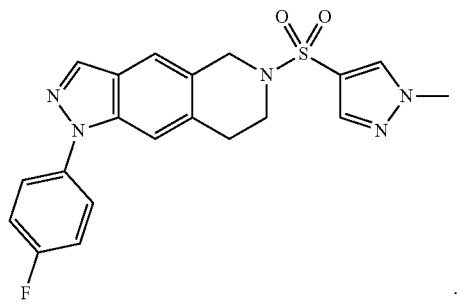
(X-5)

21. The method of claim 20, wherein the method further comprises following step (a):
(a1) mixing the first reaction mixture with water having the pH of between 4 and 5 to form the first organic phase and the first aqueous phase;
(a2) mixing the first organic phase with water and sodium chloride wherein the water has the pH of between 5 and 6; and
(a3) mixing the first organic phase and silica gel.

22. A method of purifying a compound of Formula I:

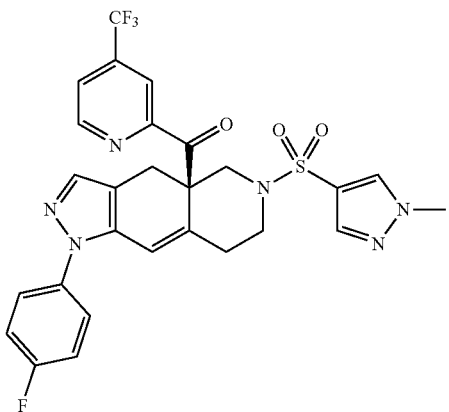
(I)

or a pharmaceutically acceptable salt thereof, comprising:
(a) eluting the compound of Formula I through a High Pressure Liquid Chromatography C18 column using
(i) a first mobile mixture comprising water in an amount of at least 95% (v/v), formic acid in an amount of 0.05 to 0.2% (v/v), and acetonitrile in an amount of 1 to 5% (v/v),
(ii) a second mobile mixture comprising water in an amount of 45 to 55% (v/v), formic acid in an amount of 0.01 to 0.1% (v/v), and acetonitrile in an amount of 45 to 55% (v/v), and
(iii) a third mobile phase comprising water in an amount of 5 to 15% (v/v), formic acid in an amount of 0.005 to 0.02% (v/v), and acetonitrile in an amount of at least 85% (v/v),
to form an eluted mixture comprising the compound of Formula I having a purity of at least 98% and the compound of Formula X-5 in an amount of less than 0.75% (w/w):

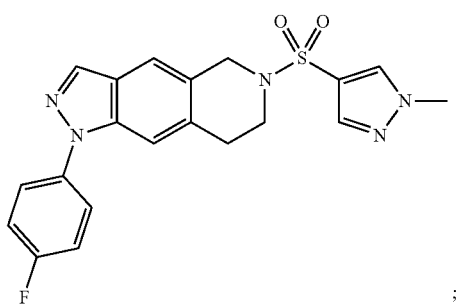

(X-5)

(a1) extracting the compound of Formula I from the eluted mixture into ethyl acetate to form an extracted mixture;
(a2) mixing the extracted mixture with methyl t-butyl ether (MTBE) under vacuum to form an MTBE mixture comprising less than 5% (v/v) ethyl acetate;
(d) filtering the MTBE mixture through a filter to form a filtered MTBE mixture comprising:
the compound of Formula I,
the compound of Formula X-5 in an amount of less than 0.5% (w/w),
a compound of Formula X-4 in an amount of less than 0.3% (w/w):

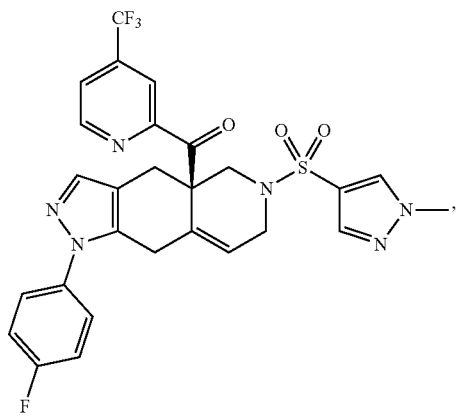

(X-4)

and
a compound of Formula X-6 in an amount of less than 0.25% (w/w):

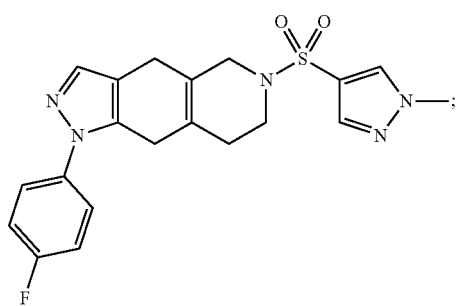

(X-6)

(e) adding the filtered MTBE mixture to heptane to form a precipitated compound of Formula I, wherein the precipitated compound of Formula I comprises 1,4-dibromopentane in an amount of less than 20 ppm;
(f) dissolving the precipitated compound of Formula I in methanol to form a methanol mixture; and
(g) adding the methanol mixture to water to precipitate the purified compound of Formula I, wherein the purified compound of Formula I has a purity of at least 99%, and comprises
the compound of Formula X-5 in an amount of less than 0.5% (w/w),
1,4-dibromopentane in an amount of less than 6 ppm,
methyl-1-methyl-1H-pyrazole-4-sulfonate in an amount of less than 6 ppm:

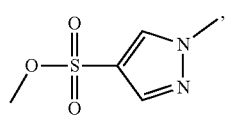

and
1-methyl-1H-pyrazole-4-sulfonyl chloride in an amount of less than 6 ppm:

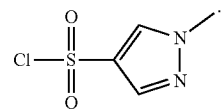

23. The method of claim 22, wherein the purified compound of Formula I has a purity of at least 99%, and further comprises
methyl bromide in an amount of less than 20 ppm, and
2-bromopropane in an amount of less than 20 ppm.

24. The method of claim 22, wherein the purified compound of Formula I has a purity of at least 99%, and comprises
methyl bromide in an amount of less than 8 ppm,
2-bromopropane in an amount of less than 8 ppm, and
1,4-dibromopentane in an amount of less than 6 ppm.

25. The method of claim 22, wherein the purified compound of Formula I has a purity of at least 99%, and comprises
the compound of Formula X-4 in an amount of less than 0.1% (w/w),
the compound of Formula X-5 in an amount of less than 0.2% (w/w),
the compound of Formula X-6 in an amount of less than 0.2% (w/w),
1,4-dibromopentane in an amount of less than 4 ppm,
1-methyl-1H-pyrazole-4-sulfonyl chloride in an amount of less than 4 ppm, and
methyl 1-methyl-1H-pyrazole-4-sulfonate in an amount of less than 4 ppm.

26. The method of claim 22, wherein the purified compound of Formula I has a purity of at least 99%, and further comprises
ethyl 1-methyl-1H-pyrazole-4-sulfonate in an amount of less than 6 ppm:

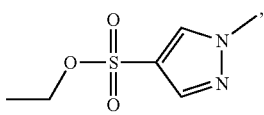

and isopropyl 1-methyl-1H-pyrazole-4-sulfonate in an amount of less than 6 ppm:

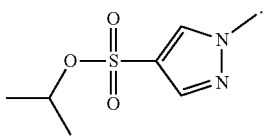

27. The method of claim 22, wherein the purified compound of Formula I has a purity of at least 99%, and comprises the compound of Formula X-4 in an amount of less than 0.1% (w/w), the compound of Formula X-5 in an amount of less than 0.2% (w/w), the compound of Formula X-6 in an amount of less than 0.2% (w/w), methyl bromide in an amount of less than 4 ppm, 2-bromopropane in an amount of less than 4 ppm, 1,4-dibromopentane in an amount of less than 4 ppm, 1-methyl-1H-pyrazole-4-sulfonyl chloride in an amount of less than 4 ppm, methyl 1-methyl-1H-pyrazole-4-sulfonate in an amount of less than 4 ppm, ethyl 1-methyl-1H-pyrazole-4-sulfonate in an amount of less than 4 ppm, and isopropyl 1-methyl-1H-pyrazole-4-sulfonate in an amount of less than 4 ppm.

28. The method of claim 22, wherein the compound of Formula I is prepared by the method of claim 5.

29. The method of claim 1, wherein

HX is

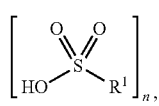

wherein $R^1$ is $C_{1-6}$ alkyl; and subscript n is 1 to 4.

30. The method of claim 29, for preparing the compound of Formula J:

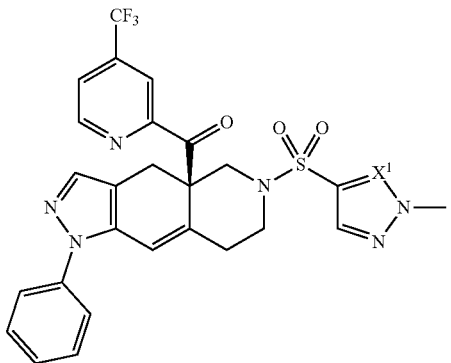

or a pharmaceutically acceptable salt thereof, comprises:

(a) forming a fourth reaction mixture comprising a compound of Formula IIb-2:

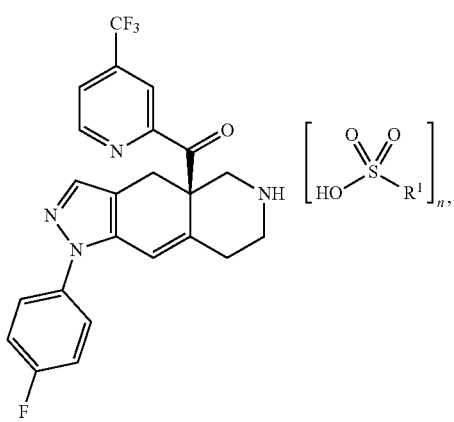

and the sulfonyl chloride:

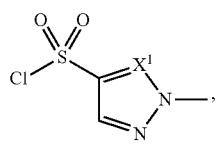

to prepare the compound of Formula J in a yield of at least 75% and a purity of at least 98%, wherein $X^1$ is —CH= or —N=;

$R^1$ is $C_{1-6}$ alkyl; and subscript n is 1 to 4.

31. A method of preparing a compound of Formula I:

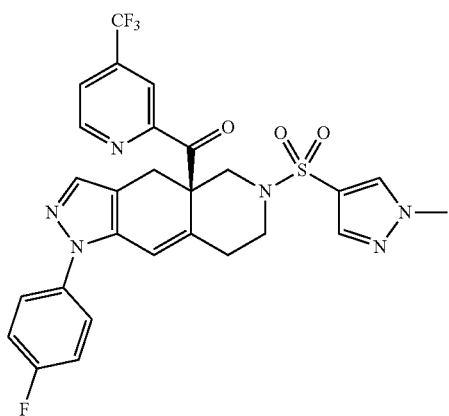

(I)

or a pharmaceutically acceptable salt thereof, comprising:
(c) forming a sixth reaction mixture comprising tetrahydrofuran, toluene, iPrMgCl, a compound of Formula III:

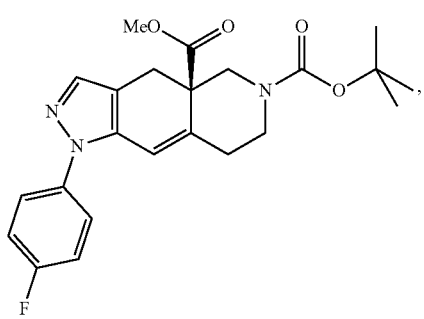

(III)

and
2-bromo-4-(trifluoromethyl)pyridine:

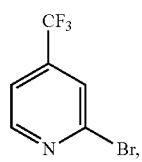

wherein the pyridine is present in a molar ratio of about 3.0 to the compound of Formula III, and wherein the Grignard reagent is present in a molar ratio of about 3.05 to the compound of Formula III;

(c1) adding acetic acid and water to the sixth reaction mixture to form a workup mixture;
(c2) distilling the workup mixture to form an intermediate mixture comprising a compound of Formula IIa:

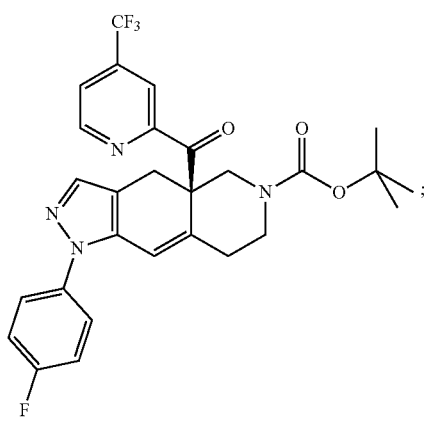

(IIa)

(b) forming a fifth reaction mixture comprising the intermediate mixture,
acetonitrile, and methanesulfonic acid, to form a compound of Formula IIb-2:

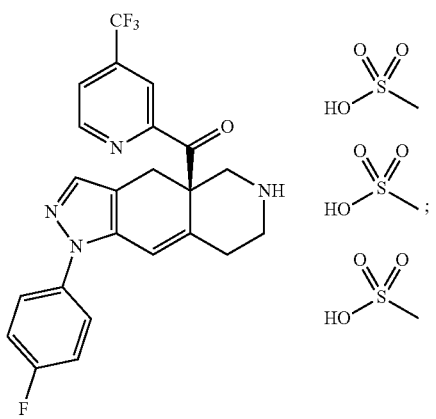

(IIb-2)

(a) forming a fourth reaction mixture comprising the compound of Formula IIb-2, triethylamine, ethyl acetate, and 1-methyl-1H-pyrazole-4-sulfonyl chloride:

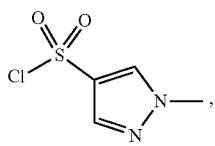

wherein the sulfonyl chloride is present in a ratio of about 1.0 to the compound of Formula IIb-2;
(a1) adding methanol to the fourth reaction mixture; and
(a2) adding water to the reaction mixture to precipitate the compound of Formula I in a yield of at least 75% and a purity of at least 98%.

32. A method of preparing a compound of Formula Ia:

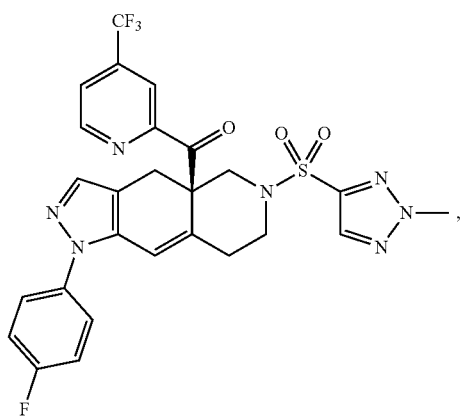

or a pharmaceutically acceptable salt thereof, comprising:
(c) forming a sixth reaction mixture comprising tetrahydrofuran, toluene, iPrMgCl, a compound of Formula III:

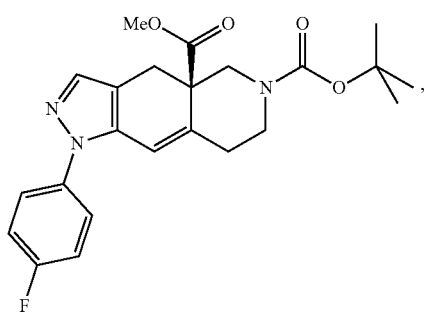

and
2-bromo-4-(trifluoromethyl)pyridine:

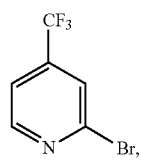

wherein the pyridine is present in a molar ratio of about 3.0 to the compound of Formula III, and wherein the Grignard reagent is present in a molar ratio of about 3.05 to the compound of Formula III;

(c1) adding acetic acid and water to the sixth reaction mixture to form a workup mixture;
(c2) distilling the workup mixture to form an intermediate mixture comprising a compound of Formula IIa:

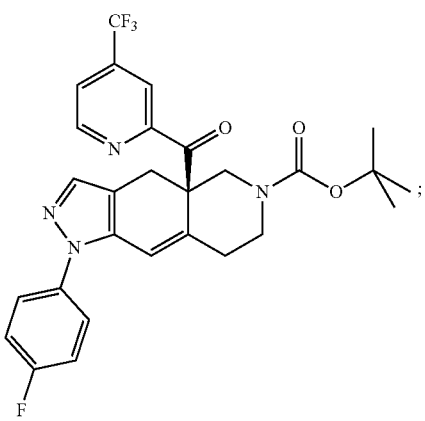

(b) forming a fifth reaction mixture comprising the intermediate mixture, acetonitrile, and methanesulfonic acid, to form a compound of Formula IIb-2:

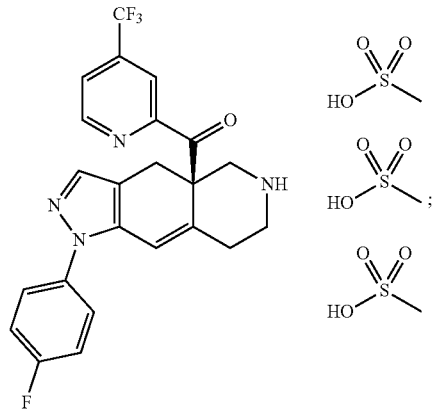

(a) forming a fourth reaction mixture comprising the compound of Formula IIb-2, triethylamine, ethyl acetate, and 2-methyl-2H-1,2,3-triazole-4-sulfonyl chloride:

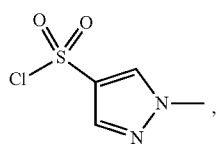

wherein the sulfonyl chloride is present in a ratio of about 1.0 to the compound of Formula IIb-2;
(a1) adding methanol to the fourth reaction mixture; and
(a2) adding water to the reaction mixture to precipitate the compound of Formula Ia in a yield of at least 75% and a purity of at least 98%.

33. A composition comprising:

a compound of Formula I in an amount of at least 99% (w/w):

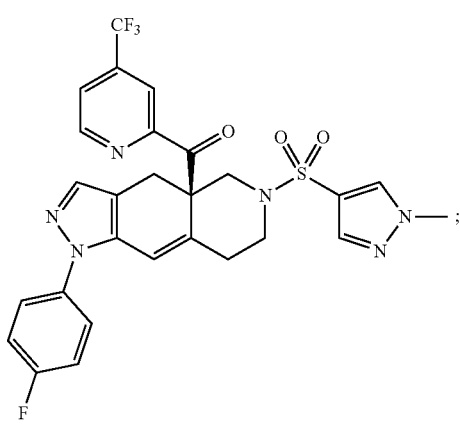
(I)

and one or more impurity in an amount of from 0.01 to 1% (w/w).

34. The composition of claim 33, wherein the impurity further comprises:

a compound of Formula X-D in an amount of less than 0.40% (w/w)

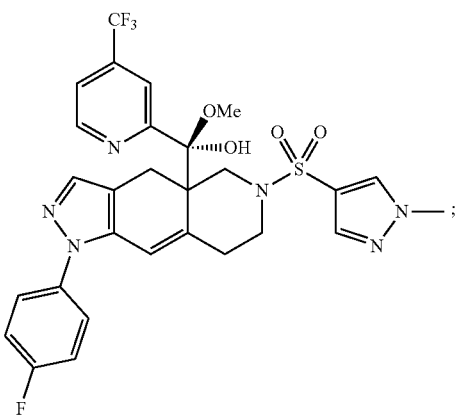
(X-D)

and a compound of Formula X-E in an amount of less than 0.40% (w/w)

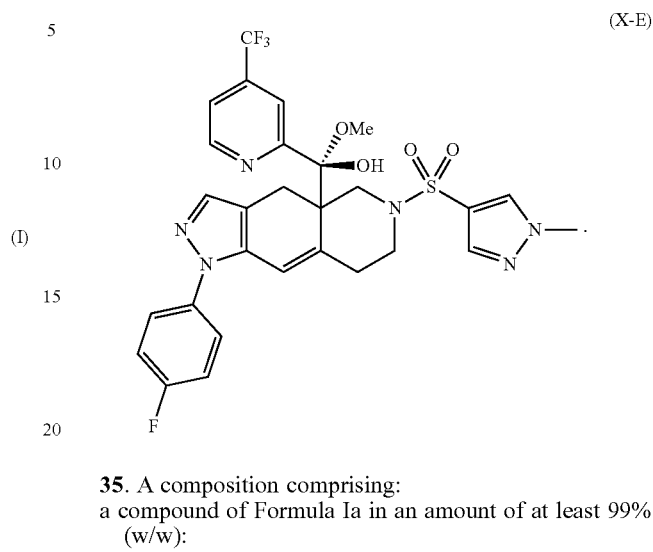
(X-E)

35. A composition comprising:

a compound of Formula Ia in an amount of at least 99% (w/w):

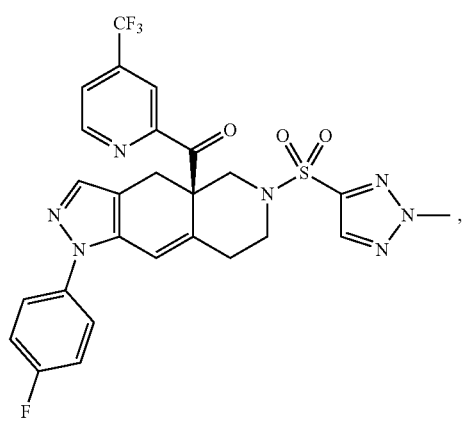
(Ia)

and one or more impurity in an amount of from 0.01 to 1% (w/w).

36. A crystalline form of (R)-(1-(4-fluorophenyl)-1,4,5,6,7,8-hexahydro-4aH-pyrazolo[3,4-g]isoquinolin-4a-yl)(4-(trifluoromethyl)pyridin-2-yl)methanone tris-methanesulfonic acid:

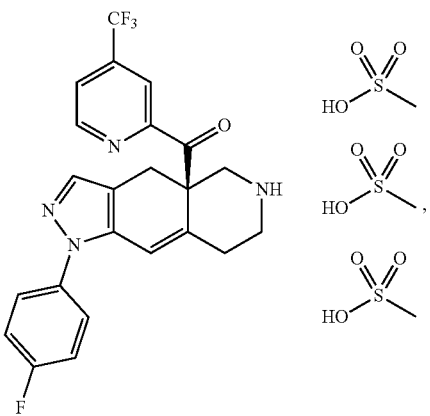

characterized by an X-ray powder diffraction (XRPD pattern having peaks at about 5.0°, 9.9°, 14.5°, 16.5°, 17.6°, 17.9°, 18.2°, 18.3°, 19.0°, 19.7°, 20.8°, 22.9°, 23.4°, and 25.3°, 2-θ±0.2° 2-θ.

37. A pharmaceutical composition comprising a composition of claim 33, and one or more pharmaceutically acceptable excipients.

38. A method of treating a disorder or condition through modulating a glucocorticoid receptor, comprising administering to a subject in need of such treatment, a therapeutically effective amount of a composition of claim 33, thereby treating the disorder or condition.

39. A method of treating a disorder or condition through antagonizing a glucocorticoid receptor, comprising administering to a subject in need of such treatment, a therapeutically effective amount of a composition of claim 33, thereby treating the disorder or condition.

40. A method of treating fatty liver disease, comprising administering to a subject in need thereof, a therapeutically effective amount of a composition of claim 33, thereby treating fatty liver disease.

41. A method of treating antipsychotic induced weight gain, comprising administering to a subject in need thereof, a therapeutically effective amount of the crystalline form of claim 33, thereby treating antipsychotic induced weight gain.

* * * * *